US006852845B1

(12) United States Patent
Rothberg et al.

(10) Patent No.: US 6,852,845 B1
(45) Date of Patent: Feb. 8, 2005

(54) METHOD OF IDENTIFYING TOXIC AGENTS USING NSAID-INDUCED DIFFERENTIAL GENE EXPRESSION IN LIVER

(75) Inventors: Bonnie Gould Rothberg, Guilford, CT (US); Vincent A. DiPippo, East Haven, CT (US); Tenmore M. Ramesh, New Milford, CT (US); Robert W. Gerwein, Brandford, CT (US)

(73) Assignee: Curagen Corporation, New Haven, CT (US)

( * ) Notice: Subject to any disclaimer, the term of this patent is extended or adjusted under 35 U.S.C. 154(b) by 280 days.

(21) Appl. No.: 09/717,321

(22) Filed: Nov. 20, 2000

Related U.S. Application Data

(60) Provisional application No. 60/166,923, filed on Nov. 22, 1999, and provisional application No. 60/183,531, filed on Feb. 18, 2000.

(51) Int. Cl.[7] .................... C12N 15/11; C12N 15/63; C12N 15/85
(52) U.S. Cl. .................. 536/23.1; 435/320.1; 435/325
(58) Field of Search ................ 536/23.1; 435/320.1, 435/326, 6, 325; 514/44

(56) References Cited

U.S. PATENT DOCUMENTS 5,871,697 A    2/1999    Rothberg et al.

FOREIGN PATENT DOCUMENTS

| WO | WO 99/27090 A1 | 6/1999 |
| WO | WO 99/39200 A1 | 8/1999 |
| WO | WO 00/63435 A2 | 10/2000 |

OTHER PUBLICATIONS

Verma et al (1997) Nature 389:239–242.*
Palù (1999) J. Biotechnol. 68: 1–13.*
Luo et al (2000) Nature Biotechnology 18:33–37.*
Fox, ASM News, Feb. 2000, 66 (2): 1–3.*
Adams, et al., 2000 "The genome sequence of Drosophila melanogaster." Science 287:2185–2195. GenBank Accession No.: Q9VIA2.
Ayte, et al., 1990 "Rat mitochondrial and cytosolic 3–hydroxy–3–methylglutaryl–CoA synthases are encoded by two different genes." Proc. Natl. Acad. Sci. U.S. A. 87, 3874–3878. GenBank Accession No.: M33648.
Cui, et al., 1983 Cloning and expression of a novel phosphatidylethanolamine N–methyltransferase. A specific biochemical and cytological marker for a unique membrane fraction in rat liver. J. Biol. CHem. 268 (22), 16655–16663. GenBank Accession No.: L14441.
Donaldson, et al., 1993 "Expression of rat liver ketohexokinase in yeast results in fructose Intolerance." Biochem. J. 291, 179–186. GenBank Accession No.: M86235.

Dziuda, D. (1990). "Specialized PC software package for creation of computer systems supporting partial diagnostics based on numerical results of medical examinations." Med Inform (Lond) 15(4): 319–26.
Furuta, et al., 1986 "Complete nucleotide sequence of cDNA and deduced amino acid sequence of rat liver catalase." Proc. Natl. Acad. Sci. U.S.A. 83, 313–317. GenBank Accession No.: M11670.
Heikkinen, S., 2000 "Mouse hexokinase II gene: structure, cDNA, promoter analysis, and expression pattern." Mamm. Genome 11 (2): 91–96. GenBank Accession No.: AJ238540.
Ishidoh, et al., 1991 "Molecular cloning of cDNA for rat cathepsin C. Cathepsin C. cysteine proteinase with an extremely long propeptide." J. Biol. Chem. 266 (25), 16312–16317. GenBank Accession No.: D90404.
Lacson, et al., 1994 "Dideoxy sequencing and structural analysis of the rat insulin–like growth factor binding protein–1 gene." Biochim. Biophys. Acta 1218 (1), 95–98. GenBank Accession No.: L22979.
Lafreniere, et al., 1996 "Isolation and characterization of GT335, a novel human gene conserved in Escherichia coli and mapping to 21q22.3." Genomics 38 (3): 264–272. GenBank Accession No.: U53003.
Lee, et al., 1998 "Rat Genome Project: Generation of a Rat EST (REST) Catalog & Rat Gene Index." Direct Submission. GenBank Accession No.: AI169175.
Lee, et al., 1998 "Rat Genome Project: Generation of a Rat EST (REST) Catalog & Rat Gene Index." Direct Submission. GenBank Accession No.: AA851963.
Matos P., 2000 "Small GTPase Rac1: Structure, Localization, and Expression of the Human Gene." Biochem. Biohphys. Res. Commun. 277 (3): 741–751. GenBank Accession No.: AJ132695.
Meier, E. 1990 Direct Submission. GenBank Accession No.: X52713.
Meier, E., 1990 "Activity of rat Mx proteins against a rhabdovirus." J. Virol. 64 (12): 6263–6269. GenBank Accession No.: P18590.
Nagamine, et al., "Isolation of cDNA for a novel human protein KNP–I that is homologous to the E. coli SCRP–27A protein from the autoimmune polyglandular disease type I (APECED) region of chromosome 21q22.3." Biochem. Biophys. Res. Commun. 225 (2), 608–616. GenBank Accession No.: P30042.

(List continued on next page.)

Primary Examiner—Terry McKelvey
Assistant Examiner—Nancy T. Vogel
(74) Attorney, Agent, or Firm—Mintz, Levin, Cohn Ferris, Glovsky & Popeo, P.C.; Ivor R. Elrifi, Esq.; Naomi S. Biswas, Esq.

(57) ABSTRACT

The invention provides methods of identifying toxic agents, e.g., hepatotoxic agents, using differential gene expression. Also provided are methods of predicting the risk level and or injury type of NSAIDs. Also disclosed are novel nucleic acid sequences whose expression is differentially regulated by NSAIDs.

14 Claims, No Drawings

OTHER PUBLICATIONS

Ohtsuka K., 1999 "Mammalian HSP40/DNAJ homologs: Cloning of novel cDNAs and propoasl RT for the classification and nomenclature." Direct Submision. GenBank Accession No.: Q9UBS4.

Shimkets, R. A., D. G. Lowe, et al. (1999). "Gene expression analysis by transcript profiliing coupled to a gene database query." *Nat. Biotechnol.* 17 (8): 798–803.

Soares, MB, 2000 Direct Submission. GenBank Accession No.: AW435096.

Sowden, et al. 1997 "Rat betaine–homocysteine methyltransferase (BHMT) mRNA." Direct Submission. GenBank Accession No.: AF038870.

Watabe, et al., 1994 "Molecular cloning and functions of rat liver hydroxysteroid sulfotransferases catalysing covalent binding of carcinogenic polycyclic arylmethanois to DNA." *Chem. Biol. Interact.* 92 (1–3), 87–105, GenBank Accession No.: D14989.

Wilson R., 1994 "RT 2.2 Mb of contiguous nucleotide sequence from chromosome III of C.RT elegans." *Nature* 368:32–38. GenBank Accession No.: Q19527.

Zimmermann, R. 1999 Direct Submission. GenBank Accession No.: AJ250137.

Bhattacharjee, A. et al. (1998). *Toxicology and Applied Pharmacology 150*: 186–195.

Bonaldo, M. et al. (1996). *Genome Research 6*: 791–806.

International Search Report, Aug. 27, 2001.

* cited by examiner

METHOD OF IDENTIFYING TOXIC AGENTS USING NSAID-INDUCED DIFFERENTIAL GENE EXPRESSION IN LIVER

RELATED APPLICATIONS

This application claims priority to U.S. Pat. No. 60/166,923, filed Nov. 22, 1999, and U.S. Pat. No. 60/183,531, filed Feb. 18, 2000, the disclosures of which are hereby incorporated by reference herein.

FIELD OF THE INVENTION

The invention relates generally to nucleic acids and polypeptides, and more particularly to the identification of differentially expressed nucleic acids and proteins in liver.

BACKGROUND OF THE INVENTION

Liver is the primary organ for biotransformation of chemical compounds and their detoxification. Liver injury produced by chemicals has been recognized for over 100 years, and hepatic damage is one of the most common toxicities among drugs at pre-clinical and clinical stages of drug development. Over 30% of new chemical entities (NCE) are generally terminated due to adverse liver effects in humans. During a period of 30 years, hepatotoxicity has been the major cause of drug withdrawal for safety reasons at the marketing stage, accounting for 18% overall drug withdrawal. Many of the drugs that are withdrawn from market due to hepatotoxicity produce lethality in a small percentage of patient population and are classified as type II lesion (or idiosyncratic, sporadic) toxicity.

Non-steroidal anti-inflammatory drugs (NSAIDs) are a group of unrelated chemical compounds that have been used to successfully treat rheumatic and musculospastic disease. Unfortunately, unwanted hepatotoxic side effects have lead to the premature market withdrawal of several NSAIDs, including Cincophen, Benoxaprofen, Piroxicam, Suprofen, and Bromfenac. The pervasiveness of idiosyncratic reactions of many NSAIDs has lead the Food and Drug Administrations Arthritis Advisory Board to conclude that NSAIDs as a group should be considered to induce hepatotoxicity.

It is estimated that annual NSAIDS consumption in the U.S exceeds 10,000 tons. Due to this large consumption of NSAIDS for a wide variety of pain and inflammatory conditions, it has become an important class of drugs responsible for liver injury, despite the overall extremely low incidence of producing hepato-toxicity. Liver injury resulting from NSAIDs can have several forms, including acute toxicity resulting from hepatocellular (parenchymal) damage (e.g. necrosis) and arrested bile flow (cholestasis). The general mechanism that is thought to mediate NSAIDS toxicity is idisyncratic reaction (Type II) to the drug (both immunologic and metabolic), which is dose independent, and presumably results from interindividual variation in drug metabolism. Currently no clear mechanism of drug-induced idiosyncratic toxicity is available. Accordingly, there remains a great need to elucidate the molecular basis of idiosyncratic hepatoxicity, such as NSAID-induced toxicity, including the identification of genes and proteins differentially expressed in response to administration of such drugs.

SUMMARY OF THE INVENTION

In accordance with the present invention, there are provided methods of screening and identifying test agents which induce hepatotoxicity, e.g. idiosyncratic hepatotoxicity. The methods of the invention are based in part on the discovery that certain nucleic acids are differentially expressed in liver tissue of animals treated with NSAIDs. These differentially expressed nucleic acids include novel sequences that, while previously described, have not heretofore been identified as responsive to drugs, such as NSAIDs, which induce idiosyncratic hepatoxicity.

In various aspects, the invention includes a method of screening a test agent for toxicity, e.g., idiosyncratic hepatotoxicity. For example, in one aspect, the invention provides a method of identifying a hepatotoxic agent by providing a test cell population comprising a cell capable of expressing one or more nucleic acids sequences responsive to drugs, e.g. NSAIDs, which induce idiosyncratic hepatotoxicity, contacting the test cell population with the test agent and comparing the expression of the nucleic acids sequences in the test cell population to the expression of the nucleic acids sequences in a reference cell population. An alteration in expression of the nucleic acids sequences in the test cell population compared to the expression of the gene in the reference cell population indicates that the test agent is hepatotoxic. In one aspect, expression in the test cell population is compared to the expression of a reference cell population exposed to a NSAID that is classified as low risk, very low risk, or overdose risk of hepatoxicity, thereby to predict whether the test agent has low, very low, or overdose risk of hepatoxicity. In another aspect, the test cell population is compared to the expression of a reference cell population exposed to a NSAID which induces a known type of hepatic injury, e.g. hepatocellular damage, cholestasis, or elevated transaminase level, thereby to predict whether the test agent is likely to induce a given type of hepatoxic injury.

In a further aspect, the invention provides a method of assessing the hepatotoxicity, e.g. idiosyncratic hepatotoxicity, of a test agent in a subject. The method includes providing from the subject a cell population comprising a cell capable of expressing one or more NSAID-responsive genes, and comparing the expression of the nucleic acids sequences to the expression of the nucleic acids sequences in a reference cell population that includes cells from a subject whose exposure status to a hepatotoxic agent is known. An alteration in expression of the in the test cell population compared to the expression of the nucleic acids sequences in the reference cell population indicates the hepatotoxicity of the test agent in the subject.

Also provided are novel nucleic acids, as well as their encoded polypeptides, whose expression is responsive to the effects of NSAID.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

DETAILED DESCRIPTION OF THE INVENTION

The invention is based in part on the discovery of nucleic acid sequences which are differentially expressed in rodent liver cells upon administration of NSAIDS. The discovery includes groups of nucleic acid sequences whose expression is correlated with hepatotoxicity risk associated with, and injury type induced by, NSAID administration.

The differentially expressed nucleic acid sequences were identified by examining 29 different NSAIDS that have varying degrees of hepatotoxicity. These 29 drugs, shown in Table 1, below, were first categorized as low dose (1–75 mg/kg) and high dose (above 75 mg/kg) drugs, then classified as non-toxic, toxic, and those withdrawn from market (within each dose). Each of the 29 NSAIDS was administered orally to groups (3 animals per group) of 12 week old male Sprague Dawley rats for 72 hours (3 days) at the dosages specified in Table 1 (e.g. Naproxen: 54 mg/kg/day PO in QD×3 days in $H_2O$). Vehicle controls (water, ethanol, canola oil) were also included (3 animals per group). The animals were sacrificed 24 hours after the final dose, liver tissue was removed on necroscopy, and total RNA was recovered from the dissected tissue. Complementary DNA (cDNA) was prepared and samples were processed through GENECALLING™ differential expression analysis, as described in U.S. Pat. No. 5,871,697 and in Shimkets et al., *Nature Biotechnology* 17: 798–803 (1999), the disclosures of which are hereby incorporated by reference herein.

TABLE 1

NSAIDS and Dosages Administered

| Compound | Dose | Vehicle |
| --- | --- | --- |
| Acetaminophen | 133 mg/kg/day p.o. in QD × 3 days. | 10% Ethanol Vehicle |
| Acetylsalicylic Acid | 200 mg/kg/day p.o. in QD × 3 days. | Canola Oil Vehicle |
| Benoxaprofen | 16 mg/kg/day p.o. in QD × 3 days. | H2O Vehicle |
| Bromfenac | 7.5 mg/kg/day p.o. in QD × 3 days. | H2O Vehicle |
| Celecoxib | 89 mg/kg/day p.o. in QD × 3 days. | Canola Oil Vehicle |
| Diclofenac | 38 mg/kg/day p.o. in QD × 3 days. | H2O Vehicle |
| Etodolac | 30 mg/kg/day p.o. in QD × 3 days. | 10% Ethanol Vehicle |
| Felbinac | 33 mg/kg/day p.o. in QD × 3 days. | Canola Oil Vehicle |
| Fenoprofen | 154 mg/kg/day p.o. in QD × 3 days. | Canola Oil Vehicle |
| Flurbiprofen | 10 mg/kg/day p.o. in QD × 3 days. | Canola Oil Vehicle |
| Ibuprofen | 211 mg/kg/day p.o. in QD × 3 days. | H2O Vehicle |
| Indomethacin | 4 mg/kg/day p.o. in QD × 3 days. | Canola Oil Vehicle |
| Ketoprofen | 10 mg/kg/day p.o. in QD × 3 days. | Canola Oil Vehicle |
| Ketorolac | 1.5 mg/kg/day p.o. in QD × 3 days. | 10% Ethanol Vehicle |
| Meclofenamate | 20 mg/kg/day p.o. in QD × 3 days. | H2O Vehicle |
| Mefenamic Acid | 79 mg/kg/day p.o. in QD × 3 days. | Canola Oil Vehicle |
| Nabumetone | 143 mg/kg/day p.o. in QD × 3 days. | Canola Oil Vehicle |
| Naproxen | 54 mg/kg/day p.o. in QD × 3 days. | 10% Ethanol Vehicle |
| Olsalazine | 222 mg/kg/day p.o. in QD × 3 days. | H2O Vehicle |
| Oxaprozin | 100 mg/kg/day p.o. in QD × 3 days. | Canola Oil Vehicle |
| Phenacetin | 100 mg/kg/day p.o. in QD × 3 days | Canola Oil Vehicle |
| Phenylbutazone | 100 mg/kg/day p o. in QD × 3 days. | Canola Oil Vehicle |
| Piroxicam | 20 mg/kg/day p.o. in QD × 3 days. | Canola Oil Vehicle |
| Sulindac | 77 mg/kg/day p.o. in QD × 3 days. | Canola Oil Vehicle |
| Sulphusalazine | 338 mg/kg/day p.o. in QD × 3 days. | Canola Oil Vehicle |
| Suprofen | 20 mg/kg/day p.o. in QD × 3 days. | Canola Oil Vehicle |
| Tenoxicam | 10 mg/kg/day p.o. in QD × 3 days. | Canola Oil Vehicle |
| Tolmentin | 100 mg/kg/day p.o. in QD × 3 days. | H2O Vehicle |
| Zomepirac | 19 mg/kg/day p.o. in QD × 3 days. | Canola Oil Vehicle |

3635 gene fragments were initially found to be differentially expressed in rat liver tissue (analysis of variance, $p<0.01$) in response to these compounds. The compounds were then classifed according to hepatotoxicity risk, as indicated in Table 2.

TABLE 2

Hepatotoxicity Risk of NSAIDs

| Compound | Risk |
| --- | --- |
| Acetaminophen | Overdose Risk |
| Acetylsalicylic Acid | Overdose Risk |
| Benoxaprofen | Low Risk |
| Bromfenac | Low Risk |
| Celecoxib | Unknown |
| Diclofenac | Low Risk |
| Etodolac | Very Low Risk |
| Felbinac | Unknown |
| Fenoprofen | Very Low Risk |
| Flurbiprofen | Very Low Risk |
| Ibuprofen | Very Low Risk |
| Indomethacin | Very Low Risk |
| Ketoprofen | Very Low Risk |
| Ketorolac | Unknown |
| Meclofenamate | Very Low Risk |
| Mefenamic Acid | Very Low Risk |
| Nabumetone | Very Low Risk |
| Naproxen | Very Low Risk |
| Olsalazine | Unknown |
| Oxaprozin | Very Low Risk |
| Phenacetin | Overdose Risk |
| Phenylbutazone | Low Risk |
| Piroxicam | Very Low Risk |
| Sulindac | Low Risk |
| Sulphasalazine | Unknown |
| Suprofen | Very Low Risk |
| Tenoxicam | Very Low Risk |
| Tolmentin | Very Low Risk |
| Zomepirac | Very Low Risk |

In order to discriminate among these groups, the above compound set was divided into a training set (consisting of three compounds per group), and a test set (consisting of the remainder. This was done to minimize the reliance on the assumptions required for parametric analyses. Compounds with unknown risk were not used in this analysis. The training set employed is shown in Table 3.

TABLE 3

Training Set of NSAIDs by Risk Classification

| Control | Low Risk | Very Low Risk | Overdose Risk |
| --- | --- | --- | --- |
| Sterile water | Benoxaprofen | Flurbiprofen | Acetaminophen |
| 10% Ethanol | Phenylbutazone | Oxaprozin | Acetylsalicylic Acid |
| Canola oil | Sulindac | Tenoxicam | Phenacetin |

The 3635 differentially expressed nucleic acid fragments were then analyzed using a stepwise multivariate analysis of variance as follows:

1. Calculate 3635 T2 (yi1) (Hoettelling's trace, one of the test statistics used for this analysis) values, one for each differentially expressed fragment. The fragment with the largest individual T2 value is selected as the first discriminatory set (yi1).

2. Calculate 3634 T2 (yi 1,yi2) values, one for each combination of two fragments. The fragment pair with the largest individual T2 value are selected as the second discriminatory set.

3. Calculate 3626 T2 (yi1,yi2,yi3, . . . yi,10), one for each combination often fragments.

The fragment set with the largest T2 value is selected as the final discriminatory set.

This stepwise procedure is used whenever the number of dependent variables (gene fragments) exceeds the number of independent variables (samples). In addition to fragment addition, fragment elimination occurs whenever an added fragment no longer contributes significant discriminatory power to the existing set. This eliminates bias as to the order fragments enter the model (Ahrens and Läuter, *Mehrdimensionale Varianzanalyse*, Akademie-Verlag, Berlin (1974); Dziuda, *Medical Inform.* 15(4): 319 (1990)).

This analysis protocol identified ten fragments that significantly ($p=6.02\times10^{-28}$) discriminated among the drugs in the test set. Two fragments on this list were not required to maintain the discriminatory ability and were subsequently removed ($p=3.96\times10^{-26}$). Differential expression of these gene fragments were successfully confirmed using an unlabeled oligonucleotide competition assay (Shimkets et al., *Nature Biotechnology* 17: 198–803 (1999)). The 8 fragments (RISKMARKER 1–8) represent both novel and known rat genes for which the sequence identity to genes in public databases is either high (>90%), moderate (70–90%), or low (<70%).

The identity of these 8 hepatoxicity risk discriminatory nucleic acid sequences(with GenBank accession numbers) are further described below. Where appropriate, the cloned sequence from isolation is provided; this sequence was then extended using either Genbank rat ESTs or from internally (Curagen Corporation) sequenced rat fragments. The extended contig sequence is provided as "consensus." Finally, the best BlastN and BlastX results are also provided. In some instances the cloned sequence is identical to a known rat gene, in those instances the name of the gene and a database accession number and the sequence listed in the database is provided:

RISKMARKER 1

RISKMARKER 1 is a novel 1265 bp gene fragment, which has 67% sequence identity to human rac1 genomic fragment [AJ132695], probable 3' UTR. The nucleic acid was initially identified in a cloned fragment having the following sequence:

```
  1 caattgaaaa aagtttgttc tagtggtcga aaggcccaac actgtgttct tgccagtgag    (SEQ ID NO: 1)

61 ttaggttgta cagaacggcg ttagcactag cgcttgacag aacctcacag acccaaaggt 121 acc
```

The cloned sequence was assembled into a contig resulting in the following consensus sequence:

```
   1 TTTTTTTTTTTTTTTTTCAAGTTCCAAAGACATTTTTTTTTTTTTTTATGATTCAAGGATTTATTAAGTCATACATGC  (SEQ ID NO: 2)

81 AAAACATACTGCTAACTGCATTAGCAAAAGATCAATGTAAAAACACTCCACAATTCTGCAACTGTCAATTGAAAAAGTT

161 TGTTCTAGTGGTCGAAAGGCCCAACACTGTGTTCTTGCCAGTGAGTTAGGTTGTACAGAACGGCGTTAGCACTAGCGCTT

241 GACAGAACCTCACAGACCCAAAGGTACCGGAAGCATGTGTCCGCGTGGGTGAGGTCTAGAGGGGCGGCATCAATCACAT

321 GACAGTGTTGGTACTCTGGCAAGACAGTGATGTTTCAGAATATCTAAAATAGTTTAAAAACTGTAAAGCCGCAGCACGTG

401 ATTTCTACACCCAGTTACTAGAAAACGAAGGGAAGCACTAGTCAGCTGAGTAAAGGAAGGTGAAAACAGGAACGCACTTC

481 TACTATCTACCAAAAAAATCTCCGAATGCATTATCAGAAAGATCTTATAGTACAGGTCAGACATATTGCTCGTTAAGAAG

561 GGGGTCCTAAAGAAAAGCACTTGCTAAGTTAGCAACTGTGAGGATGGCCAGTTTAAATATGGACTCAACGCCCCATCTGG

641 GGAGGGACAGCAGGGGAAGGGGGGCTCAAGAGAGACACTGATAAGATCGGCCATTTGTCATCTACTGTTTGACAGAAAT

721 TAACCGTTAAAAAGCTTTACCCGTGACACTTTTATTCAGTTGAATTACTCCATGTACAATGTAGTGTAAATTAATCTCTA

801 CTTCATATTAGTCAAAATACTGTCTGTCTCCTTTGATGACGTCGTGTTTCACACACTCCACCCAGCACACCCACGACTAG

881 GAACAGAATACTTCGTTAGAGGCAACACAGGAGCCAGAGTTCTGTTCAAAGCCTGCAGAAGCCGGTCAGCTGGTATTTTA

961 GAGAACTCACTATGAAATCAAAGAGCAGAGCTGTTACACCCATCGTGACGTACAGTACAAAGTTACGTAATGAGCATGGG

1041 CTGATAAGTTACAGGTGCGTTACATGGCAGCGTGTCATTAAGGAGGCTGTGCTGTGTCACACGGTCTGGGAGCTACGGGA

1121 GGGTCTGCACCCCTGAGCCCAGAAGCTGCAGTCTTCTTAAGGACAAAGTCTCTCAACAGCTTAGTGCTTACGTGTTCTCA

1201 GCACAACGCAACTTAGTTCACAAGGTATTTTGGCAATTCTTAATCTGAGCAAGAATAGGGGATTTT
```

Blast-N Results:
>gb: GENBANK-ID: HSA132695|acc:AJ132695 *Homo sapiens* rac1 gene—*Homo sapiens*, 28567 bp.

Top Previous Match Next Match
Length=28,567
Minus Strand HSPs:

```
Score = 1328 (199.3 bits), Expect = 2.8e-90, Sum P(2) = 2.8e-90
Identities = 694/1022 (67%), Positives = 694/1022 (67%), Strand = Minus/Plus Query:  1261 CCCCTATTCTTGCTCAGATTAAGAATTGCCAAAATACCTTGTGAACTAAGTTGC---GTT 1205
             ||||  ||||||| |||||||||||  ||||||||||||| |||||| |||    |||
Sbjct: 26871 CCCCCATTCTTGTTCAGATTAAGAGTTGCCAAAATACCTTCTGAACTACACTGCATTGTT 26930

Query:  1204 GTGCTGAGAACACGTAAGCACTAAGCTGTTG-AGAGACTTT-GTCCTTAAGAAGACTGCA 1147
             |||| ||||||||  | ||||| ||||   | |    ||| ||  | || ||||| | |
Sbjct: 26931 GTGCCGAGAACACCGA-GCACTGAACT-TTGCAAAGACCTTCGTCTTTGAGAAGACGGTA 26988

Query:  1146 GCTTCTGGGCTCAGG-GGTGCAGACCCTCCCGTAGCTCCCAGACCGTGTGACACAGCACA 1088
             ||||||||   |||| ||||||||  ||| | |  ||||  |   || | || |  ||||
Sbjct: 26989 GCTTCTGCAGTTAGGAGGTGCAGACACTTGC-T--CTCCTATGTAGT-T---CTCAG-AT- 27040

Query:  1087 GCCTCCTTAATGACACGCTGCC--ATGTAACGCA-CCTGT-AACTTATCAGCCCAT--GC 1034
             || |     |   |||  || ||   ||  ||| || |||| |  ||| |     ||
Sbjct: 27041 GCGTAAAGCAGAACAGCCTCCCGAATGAAGCGTTGCCATTGAACTCACCAGTGAGTTAGC 27100

Query:  1033 T-CA--T-TACGTAACTTTGTACTGTAC-GTCACGATGG-GTGTAACAGCTCTGCTCTTT 980
             ||  |||    | |||||| || |||| ||| | |  ||||
Sbjct: 27101 AGCACGTGTTCCCGACATAACATTGTACTGT-A--ATGGAGTG-AGCGTAGCAGCTCAGC 27156

Query:   979 GATTTCATAGTGAGT-TCTCTAAAATACCAGCTGACCGGCTTCTG-CAGGCTTT-GAACA 923
             |||   | | |||| || | |    ||| || |  ||||| |  G|||| |   |
Sbjct: 27157 TCTTTGG-A-TCAGTCTTTGTGATTTCATAGC-GA--GTTTTCTGACCAGCTTTTGCGGA 27211

Query:   922 GAACTCTGG-CTC--CTG-TGTTGCCTCTAACGAAGTATTCTGTTCCTAGTCGTGGGTGT 867
             ||  | ||  |    ||| ||||| || |||| ||||| |||||  ||| ||||||||||
Sbjct: 27212 GATTT-TGAACAGAACTGCTATTTCCTCTAATGAAGAATTCTGTT--TAGCTGTGGGTGT 2768

Query:   866 GCTGGGTGGAGTGTGTGAAACACGACGTCATCAAAGGAGACAGACAGTATTTTGACTAA- 808
             ||  |||||| ||||||       ||  ||||||||| ||||||||||||||||| ||
Sbjct: 27269 GCCGGGTGGGGTGTGT-----GA-----TCAAAGGACAAAGACAGTATTTTGACAAAA 27318

Query:   807 TATGAAGTAGAGATTAATT-TACACT--ACATTGTACATGGAGTAAT-TCAACTGAATAA 752
             || ||||| ||||||| |  ||||   |  |||| |   | ||||||  || |||| |||
Sbjct: 27319 TACGAAGTGGAGATTTACACTACATTGTACAAGG-A-ATGAA--AGTGTCACGGGTA-AA 27373

Query:   751 AAGTGTCACGGGTAAAGCTTTTT-AACGGTTAATTTCTG-TCAAACAGTAGATGACAA-A 695
             ||   | | | | | |  |||||||||| ||||||||||||  || |||| ||| || |
Sbjct: 27374 AACTCTAAAAGGTTAATTTCTGTCAAATGC-AGTAGATGATGAAAGAAAGGTTGGTATTA 27432

Query:   694 TG-GCCGATCTTATCAGTGTCTCTCTTGAGCCCCCCTTCCCCCTGCTGTCCCTCCCCAGA 636
              |  ||| |||   ||||| ||||  |     |||||| | |||||||||| |
Sbjct: 27433 TCAGGAAATGTTTTCTTAAGCT-T-TTCCTTTCTC-TTACACCTGCCATGCCTCCCCAAA 27489

Query:   635 TGGGGCGTTGAGTCCATATTTAAACTGGCCATCCTCACAGTTGCTAACTTAGCAAGTGCT 576
             | |||| |||| | |  |||||||||||| ||| |   ||| |||||||||| |||||||
Sbjct: 27490 TTGGGCATTTAATTCATCTTTAAACTGGTTGTTCTGTTAGTCGCTAACTTAGTAAGTGCT 27549

Query:   575 TTTCTT-TAGGACCCCCTTCTTAACGAGCAATATGTCTGACCTGTACTATAAGATCTTTC 517
             ||||||  ||| |||| |||| |  |||||||||||  |  |||| |||||  |||||||
Sbjct: 27550 TTTCTTATAGAACCCC-TTCTGACTGAGCAATATGCCTC-CTTGTATTATAAAATCTTTC 27607

Query:   516 TGATAATGCATTCGGAGATTTTTTTGGTAGATAGTAGAAGTGCGTTCC-TGTTTTCACCT 458
             |||||||||||| |||| |||||||| ||||  |  |||| ||||| ||| ||||   |
Sbjct: 27608 TGATAATGCATTAGAAGGTTTTTTTGTCGATTAGTAAAAGTGCTTTCCATGTTTACTTTAT 27667

Query:   457 TCCTT--TACTCAG--CTGAC-T-AGTGCTTCCCTTCGTTT--TCTAGTAA-C-TGGGT- 409
             T|    T| T |G  |T   |T |GT TT|    T   T  T T|  || | TG GT
Sbjct: 27668 TCAGAGCTAATAAGTGCTTTCCTTAGTT-TTCTAGTAACTAGGTGTAAAAATCATGTGTT 27726

Query:   408 GTAGAAATCACGTGCTGCGGCT-TTACAG-T--TT-TTAAACTATTTTAGATATTCTGAA 354
             G |G   T  GT T     T TT |G T TT TT||||T|T    ||  TT|T ||
Sbjct: 27727 GCAGCTTTATAGTTTTTAAAATATTTTAGATAATTCTTAAACTATG--A-ACCTTCTTAA 27783

Query:   353 ACATCACTGTCTTGCCAGAGTACCAACACTGTCATGTGATTGATGCCGCCCCTCTAGAC 294
                ||T|||TGT|TTG|||G| T|||  ||||TGT||  TG|    |T | G ||| T|T ||
Sbjct: 27764 -CATCACTGTCTTGCCAGATTACCGACACTGTCACTTGACCAATACTGACCC-TCTTTAC 27841

Query:   293 CTCACCCACGCGGACACATGCTTCCGGTA--C-CTTTGGGTCTGTGAGGTTC     245  (SEQ ID NO: 15)
             |T|   |||||G|GG||||| G| T|| GT|  |  |TTTG T T TG| GTT|
Sbjct: 27842 CTCGCCCACGCGGACACACGCCTCCTGTAGTCGCTTTGCCTAT-TGATGTTC         27892  (SEQ ID NO: 16)
```

-continued

```
Score = 930 (139.5 bits), Expect = 2.8e-90, Sum P(2) = 2.8e-90
Identities = 270/354 (76%), Positives = 270/354 (76%), Strand = Minus/Plus Query:    357 TGAAACATCACTGTCT-TGCCAGAGTACCAACACTGTCATGTGATTGATGCCGCCCCTC  299
              ||  | || || |  ||  ||    |||||  ||| |  ||  |||| |
Sbjct: 27795 TGCCAGATTACCGACACTGTCACTTGACCAATACTGACCC-TCTTT-ACCTCGCCCACGC 27852

Query:    298 TAGAC-CTCACCCAC-GCGGACACAT-GCTTCC-G--GTACCTTTGGGTCTGTGAGGTTC  245
              ||| | ||  | |   |  |       |  ||||||||||||||||
Sbjct: 27853 G-GACACCGCCTCCT GT|GTCGCTTTGCCTATTGATGTTCCTTTGGGTCTGTGAGGTTC 27911

Query:    244 TGTCAA--GCGCTAGTGCTAACGCCGTTCTGTACAACCTAACTCACTGGCAAGAACACAG  187
              TGT AA  G G|TAGTG|T A|G  GTT|TGTA|AA|  TAA|T|A|TGG|  AGAA A|AG
Sbjct: 27912 TGTAAACTGTGCTAGTGCTGACGATGTTCTGTACAACTTAACTCACTGGCGAGAATACAG 27971

Query:    186 TGTTGGGCCTTTCGACCACTAGAACAAACTTTTTTCAATTGACAGTTGCAGAATTGTGGA  127
              GT GG || TT|   ||A|TA AA|A A TTTTTT AATTGA|AGTTG|AGAATTGTGGA
Sbjct: 27972 CGTGGGACCCTTCAGCCACTACAACAGAATTTTTTAAATTGACAGTTGCAGAATTGTGGA 28033

Query:    126 GTGTTTTTACATTGATCTTTTGCTAATGCAGTTAGCAGTATGTTTTGCATGTATGACTTA   67
              GTGTTTTTA|ATTGAT|TTTTG|TAATG|A TTAG|A TATGTTTTG|ATGTATGA|TTA
Sbjct: 28032 GTGTTTTTACATTGATCTTTTGCTAATGCAATTAGCATTATGTTTTGCATGTATGACTTA 28091

Query:     66 ATAAATCCTTGAATCATAAAAAAAAAAAAAAAAATGTCTTTGGAACTTGAAAAAAAA     10  (SEQ ID NO: 17)
              ATAAAT||TTGAAT|ATA  A     AA A     TGT TTTG A|TTGA AA AA
Sbjct: 28092 ATAAATCCTTGAATCATACGACTGGTAATACTGGTGTTTTTGAGACTTGATGAACAA   28148  (SEQ ID NO: 18)
```

RISKMARKER2

RISKMARKER2 is a 650 bp rat expressed sequence tag (EST) [AW435096]. The nucleic acid sequence was initially identified in a cloned fragment having the following sequence:

Blast-N Results:
>gb:GENBANK-ID:AW435096|acc:AW435096 UI-R-BJ0p-afy-e-10-0-UI.s1 UI-R-BJ0p *Rattus norvegicus* cDNA clone UI-R-BJ0p-afy-e-10-0-UI 3', mRNA sequence— *Rattus norvegicus*, 484 bp (RNA).
Length=484

```
  1 TTTTTTTTTTTTTTTTTGGCAGAATTCTGATGTTTACTGGGACCCATAGTAGTCAAGGTGACAGCAAGGGTAGGGAGGA   (SEQ ID NO: 3)

81 AACTCAGCAGAGGCGGATCCCAGGTCTGGAGGGAAGCTGACAGCAGCCCAGTAAGCTGTGCCAGAAGGCTGTAACAGTAG

161 CGGAGCCAGTGACAGCGCCAGGCTGGGCTGGGTTCTCTCTGTGGGTGTGCACGGCAAAGCTGCGGCCTGTGGGCCCTGGG

241 GGGCCTGTCAGCTCCACATCCACCACATGCATGTCGGTGAGGCTAAGGTCAGCCACAAGCACCCCAATGACACGATCAAA

321 GCCTAGACTGGGAGCGGCCAGGGCAGCGGCTGCCATGGTGTTGGAGTTTCGGGGGGCCAAGGGGCAGAGCCCACGCACAG

401 GGCCCTCATAGAGCACTGTGCGGGGCCCACTACTATGTGCGGCAGCCAGGGGTCNCTCCAGCCGGAAGCCATCAGGATGT

481 GTGG
```

The cloned sequence was assembled into a contig resulting in the following consensus sequence:

```
  1 TTTTTTTTTTTTTTTTTGGCAGAATTCTGATGTTTACTGGGACCCATAGTAGTCAAGGTGACAGCAAGGGTAGGGAGGA   (SEQ ID NO: 4)

81 AACTCAGCAGAGGCGGATCCCAGGTCTGGAGGGAAGCTGACAGCAGCCCAGTAAGCTGTGCCAGAAGGCTGTAACAGTAG

161 CGGAGCCAGTGACAGCGCCAGGCTGGGCTGGGTTCTCTCTGTGGGTGTGCACGGCAAAGCTGCGGCCTGTGGGCCCTGGG

241 GGGCCTGTCAGCTCCACATCCACCACATGCATGTCGGTGAGGCTAAGGTCAGCCACAAGCACCCCAATGACACGATCAAA

321 GCCTAGACTGGGAGCGGCCAGGGCAGCGGCTGCCATGGTGTTGGAGTTTCGGGGGGCCAAGGGGCAGAGCCCACGCACAG

401 GGCCCTCATAGAGCACTGTGCGGGGCCCACTACTATGTGCGGCAGCCAGGGGTCNCTCCAGCCGGAAGCCATCAGGATGT

481 GTGGCCATGGTGACTCGAAGGCTCTGGAGGCCTCCGGCTGCATCCAATCTGCTGATGTCTTCACAACCCCACAGGGCCCC

561 TCGGGCCACAAACACCGTGTGGCCCCAGTGGTTTGAAGCCTCCAGGAGCTGCCGCTCTGTGGTCTGGTCAGCGAGAGCTG

641 AGGGGGATCC
```

Plus Strand HSPs:

```
Query:   1 TTTTTTTTTTTTTTTTTGGCAGAATTCTGATGTTTACTGGGACCCATAGTAGTCAAGGTG   60
           ||||||||||||||||||||||||||||||||||||||||||||||||||||||||||||
Sbjct:   1 TTTTTTTTTTTTTTTTTGGCAGAATTCTGATGTTTACTGGGACCCATAGTAGTCAAGGTG   60

Query:  61 ACAGCAAGGGTAGGGGAGGAAACTCAGCAGAGGCGGATCCCAGGTCTGGAGGGAAGCTGA  120
           ||||||||||||||||||||||||||||||||||||||||||||||||||||||||||||
Sbjct:  61 ACAGCAAGGGTAGGGGAGGAAACTCAGCAGAGGCGGATCCCAGGTCTGGAGGGAAGCTGA  120

Query: 121 CAGCAGCCCAGTAAGCTGTGCCAGAAGGCTGTAACAGTAGCGGAGCCAGTGACAGCGCCA  180
           ||||||||||||||||||||||||||||||||||||||||||||||||||||||||||||
Sbjct: 121 CAGCAGCCCAGTAAGCTGTGCCAGAAGGCTGTAACAGTAGCGGAGCCAGTGACAGCGCCA  180

Query: 181 GGCTGGGCTGGGTTCTCTCTGTGGGTGTGCACGGCAAAGCTGCGGCCTGTGGGCCCTGGG  240
           ||||||||||||||||||||||||||||||||||||||||||||||||||||||||||||
Sbjct: 181 GGCTGGGCTGGGTTCTCTCTGTGGGTGTGCACGGCAAAGCTGCGGCCTGTGGGCCCTGGG  240

Query: 241 GGGCCTGTCAGCTCCACATCCACCACATGCATGTCGGTGAGGCTAAGGTCAGCCACAAGC  300
           ||||||||||||||||||||||||||||||||||||||||||||||||||||||||||||
Sbjct: 241 GGGCCTGTCAGCTCCACATCCACCACATGCATGTCGGTGAGGCTAAGGTCAGCCACAAGC  300

Query: 301 ACCCCAATGACACGATCAAAGCCTAGACTGGGAGCGGCCAGGGCAGCGGCTGCCATGGTG  360
           ||||||||||||||||||||||||||||||||||||||||||||||||||||||||||||
Sbjct: 301 ACCCCAATGACACGATCAAAGCCTAGACTGGGAGCGGCCAGGGCAGCGGCTGCCATGGTG  360

Query: 361 TTGGAGTTTCGGGGGGCCAAGGGGCAGAGCCCACGCACAGGGCCCTCATAGAGCACTGTG  420
           ||||||||||||||||||||||||||||||||||||||||||||||||||||||||||||
Sbjct: 361 TTGGAGTTTCGGGGGGCCAAGGGGCAGAGCCCACGCACAGGGCCCTCATAGAGCACTGTG  420

Query: 421 CGGGGCCCACTACTATGTGCGGCAGCCAGGGGTCCCTCCAGCCGGAAGCCATCAGGATGT  480
           |||||||||||||||||||||||||||||||||||| |||||||||||||||||||||||
Sbjct: 421 CGGGGCCCACTACTATGTGCGGCAGCCAGGGGTCNCTCCAGCCGGAAGCCATCAGGATGT  480

Query: 421 GTGG                                                         484 (SEQ ID NO: 19)
           ||||
Sbjct: 421 GTGG                                                         484 (SEQ ID NO: 3)
```

Blast-X Results:
>ptnr:SPTREMBL-ACC:Q19527 F17C8.3 PROTEIN— *Caenorhabditis elegans*, 973 aa.

Top Previous Match Next Match
Length=973
Minus Strand HSPs:

```
Score = 351 (123.6 bits), Expect = 6.3e-30, P = 6.3e-30
Identities = 78/161 (48%), Positives = 96/161 (59%), Frame = -1

Query: 650 GSPSALADQTTERQLLEASNHWGHTVFVARGALWGCEDISRLDAAGGLQSLRVTMATHPD    471
           GSP+  A+Q    +L + S   G +  + GALWG  DI ++   G L+  L VTM HP
Sbjct: 530 GSPTCFANQELLEKLKLSLSHGKKLLIPAGALWGANDIQKMADVGSLKGLTVTMIKHPT    589

Query: 470 GFRLEGPLAAAHSSGP---RTVLYEGPVRGLCPLAPRNSNTMAAAALAAPSLGFDRVI     306
           F+L  PL  +          TVLYEG VRGLCPLAP N NTMA  ALAA +LGFD V
Sbjct: 590 SFKLGSPLFEINEKAKLEETNETVLYEGSSVRGLCPLAPNNVNTMAGGALAASNLGFDEVK  649

Query: 305 GVLVADLSLTDMHVVDVELTGPPGPTGRSFAVHTHRENPAQPGAVT                168 (SEQ ID NO: 20)
           L++D +TD HVV+V + G  G     F V T R NPA+PGAVT
Sbjct: 650 AKLISDPKMTDWHVVEVRVEGDDG-----FEVITRRNNPAKPGAVT                690 (SEQ ID NO: 21)
```

RISKMARER3

RISKMARKER3 is a 1019 nucleotide sequence encoding superoxide dismutase copper chaperone [AF255305]:

```
  1 ggtctctgga ccctaccggt tgtgtggccc aagcgggtga ctgcagccag gatggcttcg    (SEQ ID NO: 22)

61 aagtcggggg acggtggaac tatgtgtgcg ttggagttta cagtacagat gagttgtcag 121 agctgcgtgg acgctgtgca caagaccctg aaaggggcgg cgggtgtcca gaatgtggaa 181 gttcagttgg agaaccagat ggtgttggtg cagaccactt tgcccagcca ggaggtgcaa 241 gcgctcctgg aaagcacagg gaggcaggct gtactcaagg gcatgggcag cagccaacta
```

```
                                                          -continued
301 aagaatctgg gagcagcagt ggccattatg gagggcagtg gcaccgtaca gggggtggtc 361 cgcttcctac agctgtcctc tgagctctgc ctgattgagg gaaccatcga cggcctggag 421 cctgggctgc atgggcttca tgtccatcag tatgggacc ttaccaagga ctgcagcagc 481 tgtggggacc attttaaccc tgatggagca tctcatgggg gtcctcagga cactgatcgg 541 caccggggag atctgggcaa tgttcacgct gaagctagtg gccgagctac cttccggata 601 gaggataaac agctgaaggt gtgggatgtg attggccgca gtctggttgt tgatgaggga 661 gaagatgacc tgggccgggg aggccatccc ttatccaagg tcacagggaa ttctgggaag 721 aggttggcct gtggcatcat tgcacgctct gctggccttt tccagaatcc caagcagatc 781 tgctcctgtg atgggctcac tatctgggag gagcgaggcc ggcccattgc tggccaaggc 841 cgaaaggact cagcccaacc ccctgctcac ctctgaacag agcctcctgt caggttattc 901 agtcctccta gctgaacatc ttcctgcaga gggagcctca agcccttgct tgtataggcc 961 taaagggcag ataggcattg ttgtatcctg agcaaattaa attgttactc tcatatggc
```

RISKMARKER4

RISKMARKER4 is a 878 nucleotide sequence encoding alpha-2 microglubulin [U31287]:

```
  1 ggcacgagca gagagattgt cccaacagag aggcaattct attccctacc aacatgaagc   (SEQ ID NO: 23)

61 tgttgctgct gctgctgtgt ctgggcctga cactggtctg tggccatgca gaagaagcta 121 gttccacaag agggaacctc gatgtggcta agctcaatgg ggattggttt tctattgtcg 181 tggcctctaa caaaagagaa agatagaag agaatggcag catgagagtt tttatgcagc 241 acatcgatgt cttggagaat tccttaggct tcaagttccg tattaaggaa aatggagagt 301 gcagggaact atatttggtt gcctacaaaa cgccagagga tggcgaatat tttgttgagt 361 atgacggagg gaatacattt actatactta agacagacta tgacagatat gtcatgtttc 421 atctcattaa tttcaagaac ggggaaacct tccagctgat ggtgctctac ggcagaacaa 481 aggatctgag ttcagacatc aaggaaaagt ttgcaaaact atgtgaggcg catggaatca 541 ctagggacaa tatcattgat ctaaccaaga ctgatcgctg tctccaggcc cgaggatgaa 601 gaaaggcctg agcctccagt gctgagtgga gacttctcac caggactcta gcatcaccat 661 ttcctgtcca tggagcatcc tgagacaaat tctgcgatct gatttccatc ctctgtcaca 721 gaaaagtgca atcctggtct ctccagcatc ttccctaggt tacccaggac aacacatcga 781 gaattaaaag ctttcttaaa tttctcttgg ccccacccat gatcattccg cacaaatatc 841 ttgctcttgc agttcaataa atgattaccc ttgcactt
```

RISKMARKER5

RISKMARKER5 is a 2443 bp rat mRNA for Mx3 protein [X52713]. The nucleic acid was initially identified in a cloned fragment (having 100% sequence identity to the rat mRNA) having the following sequence:

```
  1 CCATGGATGAAATCTTCCAGCATCTGAATGCCTACCGCCAGGAGGCTCACAACTGCATCTCCAGCCACATTCCATTGATC   (SEQ ID NO: 5)

81 ATCCAGTATTTCATCTTGAAGATGTTTGCTGAGAAGCTGCAGAAGGGCATGCTCCAGCTCCTGCAGGACAAGGATTCCTG

161 CAGCTGGCTCCTGAAGGAAAAGAGTGACACCAGTGAGAAGAGGAGATTCCTGAAGGAGCGGTTGGCAAGGCTGGCCCAAG

241 CTCAGCGCAGGCTAGC
```

Blast-N Results:
>gb:GENBANK-ID:RNMX3|acc:X52713 Rat mRNA for
Mx3 protein—*Rattus norvegicus*, 2443 bp.
Top Previous Match Next Match
   Length=2443
Plus Strand MSPs:

Score = 1280 (192.1 bits), Expect = 9.5e-52, P = 9.5e-52
Identities = 256/256 (100%), Positives = 256/256 (100%), Strand = Plus/Plus

```
Query:     1 CCATGGATGAAATCTTCCAGCATCTGAATGCCTACCGCCAGGAGGCTCACAACTGCATCT   60   (SEQ ID NO: 24)
             ||||||||||||||||||||||||||||||||||||||||||||||||||||||||||||
Sbjct:  1710 CCATGGATGAAATCTTCCAGCATCTGAATGCCTACCGCCAGGAGGCTCACAACTGCATCT 1769

Query:    61 CCAGCCACATTCCATTGATCATCCAGTATTTCATCTTGAAGATGTTTGCTGAGAAGCTGC  120
             ||||||||||||||||||||||||||||||||||||||||||||||||||||||||||||
Sbjct:  1770 CCAGCCACATTCCATTGATCATCCAGTATTTCATCTTGAAGATGTTTGCTGAGAAGCTGC 1829

Query:   121 AGAAGGGCATGCTCCAGCTCCTGCAGGACAAGGATTCCTGCAGCTGGCTCCTGAAGGAAA  180
             ||||||||||||||||||||||||||||||||||||||||||||||||||||||||||||
Sbjct:  1830 AGAAGGGCATGCTCCAGCTCCTGCAGGACAAGGATTCCTGCAGCTGGCTCCTGAAGGAAA 1889

Query:   181 AGAGTGACACCAGTGAGAAGAGGAGATTCCTGAAGGAGCGGTTGGCAAGGCTGGCCCAAG  240
             ||||||||||||||||||||||||||||||||||||||||||||||||||||||||||||
Sbjct:  1890 AGAGTGACACCAGTGAGAAGAGGAGATTCCTGAAGGAGCGGTTGGCAAGGCTGGCCCAAG 1949

Query:   241 CTCAGCGCAGGCTAGC                                             256   (SEQ ID NO: 5)
             ||||||||||||||||
Sbjct:  1950 CTCAGCGCAGGCTAGC                                            1965
```

Blast-X Results:
>ptnr:SWISSPROT-ACC:P18590 INTERFERON-
INDUCED GTP-BINDING PROTEIN MX3— *Rattus norvegicus* (Rat), 659 aa.
Top Previous Match Next Match
   Length=659
Plus Strand HSPs:

Score = 429 (151.0 bits), Expect = 5.3e-39, P = 5.3e-39
Identities = 84/84 (100%), Positives = 84/84 (100%), Strand = +3

```
Query:     3 MDEIFQHLNAYRQEAHNCISSHIPLIIQYFILKMFAEKLQKGMLQLLQDKDSCSWLLKEK  182
             MDEIFQHLNAYRQEAHNCISSHIPLIIQYFILKMFAEKLQKGMLQLLQDKDSCSWLLKEK
Sbjct:   571 MDEIFQHLNAYRQEAHNCISSHIPLIIQYFILKMFAEKLQKGMLQLLQDKDSCSWLLKEK  630

Query:   183 SDTSEKRRFLKERLARLAQAQRRL                                      254 (SEQ ID NO: 25)
             SDTSEKRRFLKERLARLAQAQRRL
Sbjct:   631 SDTSEKRRFLKERLARLAQAQRRL                                      654 (SEQ ID NO: 26)
```

RISKMARKER6
RISKMARKER6 is 369 bp novel gene fragment, which has 98% amino acid identity (90% nucleic acid sequence identity) to Human ERj3 protein [AJ250137]. The nucleic acid sequence was initially identified in a cloned fragment having the following sequence:

```
  1 TCTAGAAAGTCACCTTGGAAGAAGTGTACGCAGGGAACTTTGTGGAAGTAGTTAGAAACAAGCCCGTAGCCAGGCAGGCT    (SEQ ID NO: 6)

81 CCTGGCAAACGGAAATGCAACTGTCGGCAGGAGATGCGAACCACACAGCTGGGACCAGGGCGCTTCCAAATGACCCAGGA

161 AGTGGTTTGTGACGAGTGCCCTAATGTCAAACTAGTGAATGAAGAACGAACACTAGAAGTGGAAATAGAGCCTGGGGTGA

241 GAGATGGCATGGAGTACCCCTTTATTGGAGAAGGTGAGCCTCATGTGGATGGGGAACCCGGAGACTTACGGTTCCGAATC

321 AAAGTTGTCAAGCACCGGATATTTGAGAGGAGAGGGGATGACCTGTACA
```

Blast-N Results: >gb:GENBANK-ID:HSA250137|acc:AJ250137 *Homo sapiens* mRNA for ERj3 protein (ERj3 gene)—*Homo sapiens*, 1159 bp.
Top Previous Match Next Match
   Length , 1159
Plus Strand HSPs:

Score = 1524 (228.7 bits), Expect = 5.6e-63, P = 5.6e-63
Identities = 334/369 (90%), Positives = 334/369 (90%), Strand = Plus/Plus Query:   1 TCTAGAAAGTCACCTTGGAAGAAGTGTACGCAGGGAACTTTGTGGAAGTAGTTAGAAACA  60
           TCTAGAA GTCAC TTGGAAGAAGT TA GCAGG AA TTTGTGGAAGTAGTTAGAAACA
Sbjct: 431 TCTAGAA-GTCACTTTGGAAGAAGTATATGCAGGAAATTTTGTGGAAGTAGTTAGAAACA 489

Query:  61 AGCCCGTAGCCAGGCAGGCTCCTGGCAAACGGAAATGCAACTGTCGGCAGGAGATGCGAA 120
            A CC GT GC AGGCAGGCTCCTGGCAAACGGAA TGCAA TGTCGGCA GAGATGCG A
Sbjct: 490 AACCTGTGGCAAGGCAGGCTCCTGGCAAACGGAAGTGCAATTGTCGGCAAGAGATGCGGA 549

Query: 121 CCACACAGCTGGGACCAGGGCGCTTCCAAATGACCCAGGAAGTGGTTTGTGACGAGTGCC 180
           CCAC CAGCTGGG CC GGGCGCTTCCAAATGACCCAGGA GTGGT TG GACGA TGCC
Sbjct: 550 CCACCCAGCTGGGCCCTGGGCGCTTCCAAATGACCCAGGAGGTGGTCTGCGACGAATGCC 609

Query: 181 CTAATGTCAAACTAGTGAATGAAGAACGAACACTAGAAGTGGAAATAGAGCCTGGGGTGA 240
           CTAATGTCAAACTAGTGAATGAAGAACGAAC CT GAAGT GAAATAGAGCCTGGGGTGA
Sbjct: 610 CTAATGTCAAACTAGTGAATGAAGAACGAACACTAGAAGTGGAAATAGAGCCTGGGGTGA 669

Query: 241 GAGATGGCATGGAGTACCCCTTTATTGGAGAAGGTGAGCCTCATGTGGATGGGGAACCCG 300
           GAGA GGCATGGAGTACCCCTTTATTGGAGAAGGTGAGCCTCA GTGGATGGGGA CC G
Sbjct: 670 GAGATGGCATGGAGTACCCCTTTATTGGAGAAGGTGAGCCTCATGTGGATGGGGAACCCG 729

Query: 301 GAGACTTACGGTTCCGAATCAAAGTTGTCAAGCACCGGATATTTGAGAGGAGAGGGGATG 360
           GAGA TTACGGTTCCGAATCAAAGTTGTCAAGCACC  ATATTTGA AGGAGAGG GATG
Sbjct: 730 GAGACTTACGGTTCCGAATCAAAGTTGTCAAGCACCGGATATTTGAGAGGAGAGGGGATG 789

Query: 361 ACCTGTACA                                                    369 (SEQ ID NO: 6)
           A  TGTACA
Sbjct: 790 ATTTGTACA                                                    798 (SEQ ID NO: 27)

Blast-X Results:
>ptnr:SPTREMBL-ACC:Q9UBS4 ERJ3 PROTEIN PRECURSOR—*Homo sapiens* (Human), 358 aa.
Top Previous Match Next Match
   Length=358
Plus Strand HSPs:

Score = (224.2 bits), Expect = 2.1e-61, P = 2.1e-61
Identities = 119/121 (98%), Positives = 120/121 (99%), Frame = +3

Query:   6 KVTLEEVYAGNFVEVVRNKPVARQAPGKRKCNCRQEMRTTQLGPGRFQMTQEVVCDECPN 185
           +VTLEEVYAGNFVEVVRNKPVARQAPGKRKCNCRQEMRTTQLGPGRFQMTQEVVCDECPN
Sbjct: 139 EVTLEEVYAGNFVEVVRNKPVARQAPGKRKCNCRQEMRTTQLGPGRFQMTQEVVCDECPN 198

Query: 186 VKLVNEERTLEVEIEPGVRDGMEYPFIGEGEPHVDGEPGDLRFRIKVVKHRIFERRGDDL 365
           VKLVNEERTLEVEIEPGVRDGMEYPFIGEGEPHVDGEPGDLRFRIKVVKH IFERRGDDL
Sbjct: 139 VKLVNEERTLEVEIEPGVRDGMEYPFIGEGEPHVDGEPGDLRFRIKVVKHPIFERRGDDL 258

Query: 366 Y                                                            368 (SEQ ID NO: 28)
           Y
Sbjct: 259 Y                                                            259 (SEQ ID NO: 29)

RISKMARKER7

RISKMARKER7 is a 594 bp novel gene fragment, which has 65% sequence identity to *Mus musculus* hexokinase II [AJ238540], probable 3'UTR. The nucleic acid sequence was initially identified in a cloned fragment having the following sequence:

```
  1 GGGCCCCACTAAAACATACACAAAAGAATAAAAATGTTCATTTTAAACTTAAACTGCTTCCTGGTTTTACAAGGCATAAA   (SEQ ID NO: 7)

81 TATATAGCATCTCCAACAGCTACCTGTAGATTCTGTTAGTGCAAAACCTTAGAAACCCTCCTGGAGCTCAAAGGCATCCG

161 GACTAGT
```

The cloned sequence was assembled into a contig resulting in the following consensus sequence:

```
  1 TTTTTTTTTTTTTTTTAAAAAAGATTATAAAATTGAATTTATTGAGTTTCACACAAGATGCACTTATAAAATTAGTACT   (SEQ ID NO: 8)

81 GAATGCCATTATGACAGAAGTGAGCATCATCCACACTCCCAAGAGCATCTGCAAAGGAAATCAATCTTCAGAGAATAGCA

161 CAGAAACAGAAAATCCAAGCGAACAAAAAGATACATCTAGGCCGTGTTCTTGTTCTGACCAGGGCCGCATTTGGCAAAGC

241 TTTCTCTGCACCTCCCCTGGTTGCCAAGGATACTTTCTTTTGTTAAAAAAAAAAGTTTAGAAGTGGGGCCCCACTAAAAC

321 ATACACAAAAGAATAAAAATGTTCATTTTAAACTTAAACTGCTTCCTGGTTTTACAAGGCATAAATATATAGCATCTCCA

401 ACAGCTACCTGTAGATTCTGTTAGTGCAAAACCTTAGAAACCCTCCTGGAGCTCAAAGGCATCCGGACTAGTTTTGTACT

481 TAAACAGGATACGGGTAAACCACTTAAAATTTGCCATCTCTGCCCAAAGTGTTTGCATGAGAACTGAGTTTCAGAAGACA

561 GCATAGGAAAGAGTCAGAAACGGTCAACTTTTTT
```

Blast-N Results:
>gb:GENBANK-ID:MMU238540|acc:AJ238540 *Mus musculus* mRNA for hexokinase II—*Mus musculus*, 5474 bp.
Top Previous Match Next Match
Length=5474
Minus Strand HSPs:

```
Score = 251 (37.7 bits), Expect = 0.045, P = 0.044
Identities = 121/184 (65%), Positives = 121/184 (65%), Strand = Minus/Plus Query:  184 GTTCGCTTGGATTTT-CTG-TTTCTGTGCTATTCTCTGAAGATT-GATTTCCTTTGCAGA  128
                G TC CT   G T  T CTG TTT TGTG T TTC   TGAA  TT GA T C T T CA A
Sbjct: 5287 GCTCTCTCTGCTAATGCTGCTTTGTGTGATCTTCAGTGAACCTTTGACT-CATCT-CATA  5344

Query:  127 TGCTCTTGGGAGTGTGGATGATGCTCACTTCTGTCATAATGG-CATTC-AGTACTAATTT   70
                T C CT GG A T  G  T  TG  C   TT TGTCAT ATG   CA T   AG ACTA TT
Sbjct: 5345 TCC-CTGGGCACTCGGTCTAGTGAGCGTTT-TGTCATCATGTACAGTAGAGAACTAGTTG  5402

Query:   69 TATAAGTGCATCTTGTGTGAAACTCA-ATAAATTCAATTTTATAATCTTTTTTAAAAAAA   11
                 AT A   CAT T  TGT AA CT    AT AAT  AATTTTA   T TTTTTT AAAAAA
Sbjct: 5403 AATTAAC-CATGTGATGTTAA-CTATTATTAATA-AATTTTAACTTTTTTTTTCAAAAAA  5459

Query:   10 AAAAAAAAAA                                                      1    (SEQ ID NO: 30)
            AAAAAAAAAA
Sbjct: 5460 AAAAAAAAAA                                                   5469   (SEQ ID NO: 31)

Score = 250 (37.5 bits), Expect = 0.051, P = 0.049
Identities = 122/184 (66%), Positives = 122/184 (66%), Strand = Minus/Plus Query:  184 GTTCGCTTGGATTTT-CTG-TTTCTGTGCTATTCTCTGAAGATT-GATTTCCTTTGCAGA  128
                G TC CT   G T  T CTG TTT TGTG T TTC   TGAA  TT GA T C T T CA A
Sbjct: 5287 GCTCTCTCTGCTAATGCTGCTTTGTGTGATCTTCAGTGAACCTTTGACT-CATCT-CATA  5344

Query:  127 TGCTCTTGGGAGTGTGGATGATGCTCACTTCTGTCATAATGG-CATTC-AGTACTAATTT   70
                T C CT GG A T  G  T  TG  C   TT TGTCAT ATG   CA T   AG ACTA TT
Sbjct: 5345 TCC-CTGGGCACTCGGTCTAGTGAGCGTTT-TGTCATCATGTACAGTAGAGAACTAGTTG  5402
```

```
-continued
Query:    69 TATAAGTGCATCTTGTGTGAAACTCA-ATAAATTCAATTTTATAATCTTTTTT-AAAAAA  12
             AT A    CAT T  TGT AA CT    AT AAT  AATTTTA   T TTTTTT AAAAAA
Sbjct:  5403 AATTAAC-CATGTGATGTTAA-CTATTATTAATA-AATTTTAACTTTTTTTTCAAAAAA  5459

Query:    11 AAAAAAAAAA                                                     1  (SEQ ID NO: 30)
             AAAAAAAAAA
Sbjct:  5460 AAAAAAAAAA                                                  5469  (SEQ ID NO: 32)
```

Blast-X Results:
>ptnr:SPTREMBL-ACC:Q9VIA2 MST84DB PROTEIN—
*Drosophila melanogaster* (Fruit fly), 70 aa.
 Top Previous Match Next Match
 Length=70
Plus Strand HSPs:

```
Score = 66 (23.2 bits), Expect = 2.2, P = 0.88
Identities = 15/48 (31%), Positives = 25/48 (52%), Frame = +3

Query:   66 YKISTECHYDRSEHHPHSQEHLQRKS------IFRE*HRNRKSKRTKR  191 (SEQ ID NO:33)
            YK+ ++ H  R +H P S++    RK          I ++   RNRK  R ++
Sbjct:    3 YKVHSKVHKARMDHSPRSKDRKDRKGRKAHSKIHKDYSRNRKDHRVRK   50 (SEQ ID NO:34)
```

RISKMARKER8

RISKMARKER8 is a 797 bp novel gene fragment, which has 94% amino acid identity (79% nucleic acid sequence identity) to human GT335 mRNA (ES1 Protein Homolog) [U53003]. The nucleic acid was initially identified in a cloned fragment having the following sequence:

```
  1 CCTAGGACTGCACAACGTGAGTCCTTGAACCAGGCTCTGGAAAAGGTGCCCAGACCACCCAATGGGACACACAGTGAGG  (SEQ ID NO:9)
 81 CCAGCCCCCAGTGAAATTCCTGCTGCTACCTGGGGCCCTTGGTGAGACTCTGGCTTCCGGCTGGTAGAAGCCAAGGTTGG
161 ACGCATAGTTGCAAAGCTCCTCCTTCAGGCACAAAGTGTCTATGCTTCTAATAGAACAGCAGCTCCCGTGTCCTGGCTGA
241 CAGCACCTTCTTCACCATGG
```

The cloned sequence was assembled into a contig resulting in the following consensus sequence:

```
  1 TTTTTTTTTTTTTTTTTTTTGAGTTTCCACTGTGGAAAAGAGTTTATTGTATGGCTGCAGGGATCTACTACAGAATCC  (SEQ ID NO:10)
 81 CCCTGGCTGCAGTTAGCTGTGCTTACTCTGGACATATCTCCGAAGACTTGGAGCCTAAATGGTTTTCTTCTTTTAGAGCT
161 TTAGTACCCGATCCATCAGACCTAGGACTGCACAACGTGAGTCCTTGAACCAGGCTCTGGAAAAGGTGCCCAGACCACCC
241 AATGGGACACACAGTGAGGCCAGCCCCCAGTGAAATTCCTGCTGCTACCTGGGGCCCTTGGTGAGACTCTGGCTTCCGG
321 CTGGTAGAAGCCAAGGTTGGACGCATAGTTGCAAAGCTCCTCCTTCAGGCACAAAGTGTCTATGCTTCTAATAGAACAGC
401 AGCTCCCGTGTCCTGGCTGACCGGAGCACACAGGCTGAGCGTGCCACAGCGACGACGGAGGCCAAGCGTGGTGCTGGTGG
481 TGTTACTTTCCCGTGAGTTCCAGCACCTTCTTCACCATGGCCCCAATCCCGTCGTGGATGTGGTGGAGTTCGGTCTCACA
561 CATGAAGGCCGGGTGGTGACCACCTTGTTTTCTGGTCGACGTGAGCTTCGGTCACACCCTTCACACAGTGCTTGGCAC
641 CCAGGGCTTTGACGGCTTCCGCGGTTCCAGCATATGGCCACTTGCCCCCCTCCTCTTGCTCATGGCCCACGGTGACCTCC
721 ACACCTTTGATCACTTTGGCTGCGAGGACAGGAGCGATGCAGCATAGGCCAATGGGCTTCTTGGCTCCGTGGAATTC
```

Blast-N Results:
>gb:GENBANK-ID:HSU53003|acc:U53003 Human GT335 mRNA, complete cds—*Homo sapiens*, 1652 bp.
Top Previous Match Next Match
   Length=1652
Minus Strand HSPs:

Score = 1141 (171.2 bits), Expect = 7.9e-46, p = 7.9e-46
Identities = 307/385 (79%), Positives = 307/385 (79%), Strand = Minus/Plus

```
Query: 797 GAATTCCACGGAGCCAAGAAGCCCATTGGCCTATGCTGCATCGCTCCTGTCCTCGCAGCC 738 (SEQ ID NO:35)
           GA TTCCAC    GCC  GAAGCCCAT GGC T TGCTGCAT GC CCTGTCCTCGC GCC
Sbjct: 577 GAGTTCCACCAGGCCGGGAAGCCCATCGGCTTGTGCTGCATTGCACCTGTCCTCGCGGCC 636 (SEQ ID NO:36)

Query: 737 AAAGTGATCAAAGGTGTGGAGGTCACCGTGGGCCATGAGCAAGAGGAGGGGGCAAGTGG  678
           AA GTG TCA AGG GT GAGGT AC GTGGGCCA GAGCA GAGGA GG GGCAAGTGG
Sbjct: 637 AAGGTGCTCAGAGGCGTCGAGGTGACTGTGGGCCACGAGCAGGAGGAAGGTGGCAAGTGG  696

Query: 677 CCATATGCTGGAACCGCGGAAGCCGTCAAAGCCCTGGGTGCCAAGCACTGTGTGAAGGGT  618
           CC TATGC GG ACCGC GA GCC TCAA GCCCTGGGTGCCAAGCACTG GTGAAGG
Sbjct: 697 CCTTATGCCGGGACCGCAGAGGCCATCAAGGCCCTGGGTGCCAAGCACTGCGTGAAGGAA  756

Query: 617 GTGACCGAAGCTCACGTCGACCAGAAAAACAAGGTGGTCACCACCCCGGCCTTCATGTGT  558
           GTG    CGAAGCTCACGT GACCAGAAAAACAAGGTGGTCAC ACCCC GCCTTCATGTG
Sbjct: 757 GTGGTCGAAGCTCACGTGGACCAGAAAAACAAGGTGGTCACGACCCCAGCCTTCATGTGC  816

Query: 557 GAGACCGAACTCCACCACATCCACGACGGGATTGGGGCCATGGTGAAGAAGGTGCTGGAA  498
           GAGAC G ACTCCAC ACATCCA GA GGGAT GG GCCATGGTGA GAAGGTGCTGGAA
Sbjct: 817 GAGACGGCACTCCACTACATCCATGATGGGATCGGAGCCATGGTGAGGAAGGTGCTGGAA  876

Query: 497 CTCACGGGAAAGTAACAC-CACC-A-GCACCAC-GCTTGGCCTCCGT-CGTCGCTGTGGC  443
           CTCAC GGAAAGT AC C CA    A G    C C GCT GGC   C G   C T GC  T  C
Sbjct: 877 CTCACTGGAAAGTGACGCGCATGGACGGGGCCCAGCTAGGCGCCAGGACTTGGCC-T--C  933

Query: 442 ACGCTCAGCCTGTGT-GCTC-CGGTCAGC                                416
           AC CTC G CTG G  GCT  CGG C GC
Sbjct: 934 ACCCTCTGGCTGAGGAGCTGTCGG-CTGC                                961
```

Blast-X Results:
>ptnr:SWISSNEW-ACC:P30042 ES1 PROTEIN HOMOLOG, MITOCRONDRIAL PRECURSOR (PROTEIN KNP-I) (GT335 PROTEIN)—*Homo sapiens* (Human) 268 aa.
Top Previous Match Next Match
   Length=268
Minus Strand HSPs:

Score = 505 (177.8 bits), Except = 2.0e-47, P = 2.0e-47
Identities = 94/104 (90%), Positives = 99/104 (95%), Frame = -1

```
Query: 797 EFHGAKKPIGLCCIAPVLAAKVIKGVEVTVGHEQEEGGKWPYAGTAEAVKALGAKHCVKG  618 (SEQ ID NO:37)
           EFH A KPIGLCCIAPVLAAKV++GVEVTVGHEQEEGGKWPYAGTAEA+KALGAKHCVK
Sbjct: 165 EFHQAGKPIGLCCIAPVLAAKVLRGVEVTVGHEQEEGGKWPYAGTAEAIKALGAKHCVKE  224 (SEQ ID NO:38)

Query: 617 VTEAHVDQKNKVVTTPAFMCETELHHIHDGIGAMVKKVLELTGK                  486
           V EAHVDQKNKVVTTPAFMCET LH+IHDGIGAMV+KVLELTGK
Sbjct: 225 VVEAHVDQKNKVVTTPAFMCETALHYIHDGIGAMVRKVLELTGK                  268
```

Principle components analysis was used to generate three eigenvectors used to transform the original expression level data matrix, as shown in Table 4 below. Eigenvector 1 values represent NSAIDs with low risk of hepatoxicity, Eigenvector 2 values represent NSAIDs with very low risk of hepatoxicity, and Eigenvector 3 values represent NSAIDs with overdose risk of hepatoxicity.

TABLE 4

Transform Eigenvectors for Hepatoxicity Markers by Risk Classification

| Gene | Eigenvector 1 | Eigenvector 2 | Eigenvector 3 |
|---|---|---|---|
| RISKMARKER 1 | 26.9 | 6.7 | −0.9 |
| RISKMARKER 2 | 23.3 | −1.4 | 1.5 |

TABLE 4-continued

Transform Eigenvectors for Hepatoxicity Markers by Risk Classification

| Gene | Eigenvector 1 | Eigenvector 2 | Eigenvector 3 |
|---|---|---|---|
| RISKMARKER 3 | −26.0 | −1.5 | −2.3 |
| RISKMARKER 4 | 12.6 | −2.2 | −6.4 |
| RISKMARKER 5 | 18.0 | −1.3 | −3.1 |
| RISKMARKER 6 | −13.8 | 4.71 | 19.3 |
| RISKMARKER 7 | −29.7 | −7.5 | 1.3 |
| RISKMARKER 8 | 19.3 | 1.2 | −2.6 |
| % of variation explained | 99.6 | 0.4 | 0.1 |

These eigenvectors may be used to transform the expression levels of RISKMARKERS 1–8 ("RISKMARKERS") in response to a given drug, in order to determine that drug's hepatotoxicity risk. For example, expression levels of RISKMARKERS correlating with Eigenvector 1 indicates that the test drug has a low risk of hepatotoxicity. Alternatively, a drug's RISKMARKERS expression profile can be generated simultaneously with the above-described training set (or an equivalent set) run in parallel with the test drug, and expression levels associated with the test drug directly compared to those of the training set.

A second training set based on type of injury (hepatocellular damage, cholestasis, elevated transaminase level) was also constructed, utilizing the compounds indicated in Table 5, below.

TABLE 5

Training Set of NSAIDs by Injury Type

| Control | Hepatocellular | Cholestasis | Elevated transmainases |
|---|---|---|---|
| Sterile water | Acetaminophen | Benoxaprofen | Zomepirac |
| 10% ethanol | Flurbiprofen | Nabumetone | Mefenamic acid |
| Canola oil | Ketoprofen | Sulindac | Tenoxicam |

This analysis produced ten fragments that significantly ($p=8.7 \times 10-18$) discriminated among the drugs in the test set. The identities of these ten fragments (INJURYMARKER 1–10) that are included in the discriminatory set (with GenBank accession numbers) are shown below. Where appropriate, the cloned sequence from isolation is provided, and this sequence was then extended using either Genbank rat ESTs or from internally sequenced (Curagen Corporation) rat fragments. The fragments were used to extend the cloned sequence, and the extended contig sequence is provided as "consensus." Finally, the best BlastN and BlastX results are also provided. In some instances the cloned sequence is identical to a known rat gene, in those instances the name of the gene and the GenBank accession number is provided.

INJURYMARKER 1

INJURYMARKER1 is a 1025 bp rat express sequence tag (EST) [AI169175]. The nucleic acid was initially identified in a cloned fragment having the following sequence:

```
  1  CTGATTTCAAATTTTTATTAGAGAACACTTTCGGATTTCAAATTTTTATTACAGAACAAACATTTTCTGATTTCAAATTT   (SEQ ID NO:11)
 81  CTATTATAATTCTCCAGTAATCAAAGCAGTGGCGTTGGCATGAAGGCAGACAGAGGTCATGGAAGAGACCAGGCTCAGAA
161  ACAGCCCCACCATGCACAGCGGGATGTTTTCCCACCAAGGGCAACATGCAAAGCCAGGTATCCACATGGGTAGAGTAGAA
241  AGTCAGACCTTACATCTCACACACAAATGAACTCAAAATATACCAGAGAGCAAAGCTAAGAGCTAAAATCAAGTTTCCTA
321  GGGCAAGCTGTAGTAGGTCCCTTGGGTGGGTTAATGCTTTTGTGGATGTGACTACCAAAAATTCAAACCAGAGCCAACGA
401  CCCAACTATTAATGGGCAGTGGACCTAAAGAGATTTCTTCAAACGATATATAAAGAAGGCCACCAAGCATATAAAACATG
481  TGACATCAGTAGTCAGAGAGATGGGAAGCAGAAGCACTAGCAGATCTTAACACCTACTAGAACANCCACTAAAAAAGAGT
561  AAGACTCACAAGGACATGGGCACTTCTAATCTCTGTGCACTGCTGCCAGGACATACAATAGTGTGGTCACTATGGAGACT
641  ACGGCAGTGCCTACTAATAACAGCAGAGTTACCCTAAGACATACAATCTGCTGCGTGTATGCTAAGCAGGATCCGAGGGA
721  TATTTGTATATACATGTTCACAGCATAGTCAGGAGCTCCAGGGTGGGAACAACTGAGGTACC
```

The cloned sequence was assembled into a contig resulting in the following consensus sequence:

```
  1  CTGATTTCAAATTTTTATTATAGAACACTTTCTGATTTCAAATTTTTATTACAGAACAAACATTTTCTGATTTCAAATTT   (SEQ ID NO:12)
 81  CTATTATAATTCTCCAGTAATCAAAGCAGTGGCGTTGGCATGAAGGCAGACAGAGGTCATGGAAGAGACCAGGCTCAGAA
161  ACAGCCCCACCATGCACAGCGGGATGTTTTCCCACCAAGGGCAACATGCAAAGCCAGGTATCCACATGGGTAGAGTAGAA
241  AGTCAGACCTTACATCTCACACACAAATGAACTCAAAATATACCAGAGAGCAAAGCTAAGAGCTAAAATCAAGTTTCCTA
321  GGGCAAGCTGTAGTAGGCTCCCTTGGGTGGGTTAATGCTTTTGTGGATGTGACTACCAAAAATTCAACCAGAGCCAACGA
401  CCCAACTATTAATGGGCAGTGGACCTAAAGAGATTTCTTCAAACGATATATAAAGAAGGCCACCAAGCATATAAAACATG
481  TGACATCAGTAGTCAGAGAGATGGGAAGCAGAAGCACTAGCAGATCTTAACACCTACTAGAACAGCCACTAAAAAAGAGT
561  AAGACTCACAAGGACATGGGCACTTCTAATCTCTGTGCACTGCTGCCAGGACATACAATAGTGTGGTCACTATGGAGACT
```

-continued

```
641 ACGGCAGTGCCTACTAATAACAGCAGAGTTACCCTAAGACATACAATCTGCTGCGTGTATGCTAAGCAGGATCCGAGGGA

721 TATTTGTATATACATGTTCACAGCATAGTCAGGAGCTCCAGGGTGGGAACAACTGAGGTACCCACGGCTGGATGAGTAGG

801 TAACAAGAAACATACAGCATACATACAACACACACTAAAGTCTAAAGTACTATTTGTCCTTACAAAGGAAACTCATACAT

881 GATACAAGCCTTCACGGCATTCTGCTACATGAACACGCACACACACACACACACACACACACACACGCACTGAGAATC

961 TATGTATACCAGGCACTTAGGGTACTCAAATTCAGAAACAGGACAGAGAATGGTGATTGCCATGG
```

Blast-N Results:

>gb:GENBANK-ID:AI169175|acc:AI169175 EST215009 Normalized rat kidney, Bento Soares Rattus sp. CDNA clone RKIBO44 3' end, mRNA sequence—Rattus sp., 670 bp (RNA).

Top Previous Match Next Match
Length=670
Plus Strand HSPs:
Score=3305 (495.9 bits), Expect=4.3e-143, P=4.3e-143
Identities=661/661 (100%), Positives=661/661 (100%), Strand=Plus/Plus

```
Score = 3305 (495.9 bits), Except = 4.3e-143, P = 4.3e-143
Identities = 661/661 (100%), Positives = 661/661 (100%), Strand = Plus/Plus Query:    4 ATTTCAAATTTTTATTATAGAACACTTTCTGATTTCAAATTTTTATTACAGAACAAACAT  63  (SEQ ID NO:39)
            ||||||||||||||||||||||||||||||||||||||||||||||||||||||||||||
Sbjct:    1 ATTTCAAATTTTTATTATAGAACACTTTCTGATTTCAAATTTTTATTACAGAACAAACAT  60  (SEQ ID NO:40)

Query:   64 TTTCTGATTTCAAATTTCTATTATAATTCTCCAGTAATCAAAGCAGTGGCGTTGGCATGA 123
            ||||||||||||||||||||||||||||||||||||||||||||||||||||||||||||
Sbjct:   61 TTTCTGATTTCAAATTTCTATTATAATTCTCCAGTAATCAAAGCAGTGGCGTTGGCATGA 120

Query:  124 AGGCAGACAGAGGTCATGGAAGAGACCAGGCTCAGAAACAGCCCCACCATGCACAGCGGG 183
            ||||||||||||||||||||||||||||||||||||||||||||||||||||||||||||
Sbjct:  121 AGGCAGACAGAGGTCATGGAAGAGACCAGGCTCAGAAACAGCCCCACCATGCACAGCGGG 180

Query:  184 ATGTTTTCCCACCAAGGGCAACATGCAAAGCCAGGTATCCACATGGGTAGAGTAGAAAGT 243
            ||||||||||||||||||||||||||||||||||||||||||||||||||||||||||||
Sbjct:  181 ATGTTTTCCCACCAAGGGCAACATGCAAAGCCAGGTATCCACATGGGTAGAGTAGAAAGT 240

Query:  244 CAGACCTTACATCTCACACACAAATGAACTCAAAATATACCAGAGAGCAAAGCTAAGAGC 303
            ||||||||||||||||||||||||||||||||||||||||||||||||||||||||||||
Sbjct:  241 CAGACCTTACATCTCACACACAAATGAACTCAAAATATACCAGAGAGCAAAGCTAAGAGC 300

Query:  304 TAAAATCAAGTTTCCTAGGGCAAGCTGTAGTAGGCTCCCTTGGGTGGGTTAATGCTTTTG 363
            ||||||||||||||||||||||||||||||||||||||||||||||||||||||||||||
Sbjct:  301 TAAAATCAAGTTTCCTAGGGCAAGCTGTAGTAGGCTCCCTTGGGTGGGTTAATGCTTTTG 360

Query:  364 TGGATGTGACTACCAAAAATTCAACCAGAGCCAACGACCCAACTATTAATGGGCAGTGGA 423
            ||||||||||||||||||||||||||||||||||||||||||||||||||||||||||||
Sbjct:  361 TGGATGTGACTACCAAAAATTCAACCAGAGCCAACGACCCAACTATTAATGGGCAGTGGA 420

Query:  424 CCTAAAGAGATTTCTTCAAACGATATATAAAGAAGGCCACCAAGCATATAAAACATGTGA 483
            ||||||||||||||||||||||||||||||||||||||||||||||||||||||||||||
Sbjct:  421 CCTAAAGAGATTTCTTCAAACGATATATAAAGAAGGCCACCAAGCATATAAAACATGTGA 480

Query:  484 CATCAGTAGTCAGAGAGATGGGAAGCAGAAGCACTAGCAGATCTTAACACCTACTAGAAC 543
            ||||||||||||||||||||||||||||||||||||||||||||||||||||||||||||
Sbjct:  481 CATCAGTAGTCAGAGAGATGGGAAGCAGAAGCACTAGCAGATCTTAACACCTACTAGAAC 540

Query:  544 AGCCACTAAAAAAGAGTAAGACTCACAAGGACATGGGCACTTCTAATCTCTGTGCACTGC 603
            ||||||||||||||||||||||||||||||||||||||||||||||||||||||||||||
Sbjct:  541 AGCCACTAAAAAAGAGTAAGACTCACAAGGACATGGGCACTTCTAATCTCTGTGCACTGC 600

Query:  604 TGCCAGGACATACAATAGTGTGGTCACTATGGAGACTACGGCAGTGCCTACTAATAACAG 663
            ||||||||||||||||||||||||||||||||||||||||||||||||||||||||||||
Sbjct:  601 TGCCAGGACATACAATAGTGTGGTCACTATGGAGACTACGGCAGTGCCTACTAATAACAG 660

Query:  664 C                                                            664
            |
Sbjct:  661 C                                                            661
```

INJURYMARKER2

INJURYMARKER2 is a 893 nucleotide sequence encoding phosphotidylethanolamine N-methyltransferase [L14441]:

```
  1 tccccgctga gttcatcacc agggacaggt gacctgagct gcccctggag cccagctccc   (SEQ ID NO:41)
 61 atttccttct ggttctggcc gatctcttcg ttatgagctg gctgctggt tacgtggacc
121 ccacagagcc cagctttgtg gcggctgtgc tcaccattgt gttcaatcca ctcttctgga
181 atgtggtagc aaggtgggag cagagaactc gcaagctgag cagagccttc gggtcccctt
241 acctagcctg ctattccctg ggcagcatca tcctgcttct gaacatcctc cgctcccact
301 gcttcacaca ggccatgatg agccagccca agatggaggg cctggatagc cacaccatct
361 acttcctggg ccttgcactc ctgggctggg gactcgtgtt tgtgctctcc agcttctatg
421 cactggggtt cactgggacc tttctaggtg actactttgg gatcctcaag gagtccagag
481 tgaccacatt tcccttcagc gtgctggaca accccatgta ctggggaagt acagccaact
541 acctaggctg ggcacttatg cacgccagcc ctacaggcct gctgttgacg gtgctggtgg
601 cactcgtcta cgtggttgct ctcctgtttg aagagccctt cactgcggag atctaccggc
661 ggaaagccac caggttgcac aaaaggagct gacagggcca tgagggacct ttggaaagcc
721 ggattgcctc ccggctgacc caagcaacaa cccttctcgg ggagagcagc gctggccatt
781 gtacctgtgc cttggaaacc agtcatgggg gtgctcaggc attatgtcat gtgactgctg
841 agaccccat ccccaccaat ccctgacaca ataataaagg ctttgtgacc tcc
```

INJURYMARKER3

INJURYMARKER3 is a 1131 nucleotide hexokinase-encoding sequence [M86235]:

```
  1 agcaggaatc ccctccgctt gcgggtagga agcttgggga gcagcctcat ggaagagaag   (SEQ ID NO:42)
 61 cagatcctgt gcgtggggct ggtggtgctg gacatcatca atgtggtgga caaatacca
121 gaggaagaca cggatcgcag gtgcctatcc cagagatggc agcgtggagg caacgcgtcc
181 aactcctgca ctgtgctttc cttgctcgga gcccgctgtg ccttcatggg ctcgctggcc
241 catggccatg ttgccgactt cctggtggcc gacttcaggc ggaggggtgt ggatgtgtct
301 caagtggcct ggcagagcca gggagatacc ccttgctcct gctgcatcgt caacaactcc
361 aatggctccc gtaccattat tctctacgac acgaacctgc cagatgtgtc tgctaaggac
421 tttgagaagg tcgatctgac ccggttcaag tggatccaca ttgagggccg gaatgcatcg
481 gaacaggtaa agatgctaca gcggatagaa cagtacaatg ccacgcagcc tctgcagcag
541 aaggtccggg tgtccgtgga gatagagaag ccccgagagg aactcttcca gctgttcggc
601 tatggagagg tggtgtttgt cagcaaagat gtggccaagc acctggggtt ccggtcagca
661 ggggaggccc tgaagggctt gtacagtcgt gtgaagaaag gggctacgct catctgtgcc
721 tgggctgagg agggagccga tgccctgggc cccgacggcc agctgctcca ctcagatgcc
781 ttcccaccac cccgagtact agacactctc ggggctggag acaccttcaa tgcctctgtc
841 atcttcagcc tctccaaggg aaacagcatg caggaggccc tgagattcgg gtgccaggtg
901 gctggcaaga agtgtggctt gcaggggttt gatggcattg tgtgagagat gagcggtggg
961 aggtagcagc tcgacacctc agaggctggc accactgcct gccattgcct tcttcatttc
```

-continued

```
1021 atccagcctg gcgtctggct gcccagttcc ctgggccagt gtaggctgtg gaacgggtct
1081 ttctgtctct tctctgcaga cacctggagc aaataaatct tccctgagc c
```

INJURYMARKER4

INJURYMARKER4 is a 1994 nucleotide sequence encoding mitochondrial HMG-CoA Synthase [M33648]:

(SEQ ID NO:43)

```
   1 atctctccca ggggctgtgg actgctggct ttctgttgat accttagaga tgcagcggct
  61 tttggctcca gcaaggcggg tcctgcaagt gaagagagtc atgcaggaat cttcgctctc
 121 acccgctcac ctgctccccg acgcccagca gaggttttct acaatcctc ctgctcccct
 181 ggccaaaact gatacatggc caaagatgt gggcatcctt gccctggagg tatactttcc
 241 agcccaatat gtggaccaaa ctgacctgga aagttcaac aatgtggaag cagggaagta
 301 cacagtgggc ttgggccaga cccgtatggg cttctgttcg gtccaggagg acatcaactc
 361 cttgtgcctc acagtggtgc agaggctgat ggaacgcaca aagctgccat gggatgccgt
 421 aggccgcctg gaagtgggca cggaaaccat cattgacaag tccaaggctg tcaagacagt
 481 gctcatggag ctcttccagg attcaggcaa cactgacatc gagggcatag ataccaccaa
 541 cgcctgctat ggtggcactg cctccctctt caacgctgcc aactggatgg agtccagcta
 601 ctgggatggt cgctatgccc tggtggtctg tggtgatatc gcagtctacc caagtggtaa
 661 cccccgcccc acaggtggtg ccggggctgt ggcaatgctg attgggccca aggcccgct
 721 agtcctggaa caagggctga ggggaaccca catggagaac gcctatgact tctacaaacc
 781 aaacttggcc tcagagtatc cactggtgga tgggaagctg tctatccagt gctacctgcg
 841 ggccttggac cgatgctatg cagcttaccg caggaaaatc cagaatcagt ggaagcaagc
 901 tggaaacaac cagcctttca ccctcgatga cgtgcaatat atgatcttcc acacacccTT
 961 ttgcaagatg gtccagaaat ccctagctcg gctgatgttc aatgacttcc tgtcatctag
1021 cagtgacaag cagaacaact tatacaaggg tatagaggcc ttcaagggtc taaagctgga
1081 agaaacctac accaacaagg atgttgacaa ggctctgctg aaggcctccc tggacatgtt
1141 caacaagaaa accaaggcct ccctttacct ctccacaaac aatgggaaca tgtacacctc
1201 gtccctctac gggtgcctgg cctcacttct ctcccaccac tctgcccaag aattggccgg
1261 ctccaggatt ggagccttct cctacggctc aggcttagca gcaagtttct tctcatttcg
1321 agtgtccaag gacgcttccc caggttcccc tctggagaag ctggtgtcta gtgtgtcaga
1381 tctgcccaaa cgtctagact cccggagacg catgtcccct gaggaattca cagaaataat
1441 gaatcagaga gagcaatttt accacaaggt gaacttctct cccctggtg acacaagcaa
1501 cctcttccca ggcacttggt accttgaacg agtggatgag atgcaccgca gaaaatatgc
1561 ccggcgtccc gtctaaggag accaatccat acaaccattc cccggggaaa gaatgtgagc
1621 agagccgtta cccaaacggc ttccacttaa aattccaccc acagcagtga acggtaata
1681 gacacagcga ccccatagga tctgctccgc ggtgaagggc ctccctctgt ggatcctggg
1741 tgaccctccc tgaagcagtg agcaccacag gttctgctgt ggaccagagc ccctgtgg
1801 agagggagaa agaaagggga gccgctgacc tgcagggata cagaccttcc ccacagcctg
1861 gcagccgccc gtttgttgca gcttattatc agactgtggg ctatcatagt tcatgctcgt
```

-continued

```
1921 ttcttaaagt ttcccgagaa tttctaaaat tttgtatcta aacttttaat atggcgatta
1981 aaaggagaga agga
```

INJURYMARER5

INJURYMARKER5 is a 1850 nucleotide sequence encoding cathepsin C [D90404], having the following [10] nucleic acid sequence:

(SEQ ID NO:44)
```
   1 gaattccggt tctagttgtt gttttctctg ccatctgctc tccgggcgcc gtcaaccatg
  61 ggtccgtgga cccactcctt gcgcgccgcc ctgctgctgg tgcttttggg agtctgcacc
 121 gtgagctccg acactcctgc caactgcact taccctgacc tgctgggtac ctgggttttc
 181 caggtgggcc ctagacatcc ccgaagtcac attaactgct cggtaatgga accaacagaa
 241 gaaaaggtag tgatacacct gaagaagttg gatactgcct atgatgaagt gggcaattct
 301 gggtatttca ccctcattta caaccaaggc tttgagattg tgttgaatga ctacaagtgg
 361 tttgcgtttt tcaagtatga agtcaaaggc agcagagcca tcagttactg ccatgagacc
 421 atgacagggt gggtccatga tgtcctgggc cggaactggg cttgctttgt tggcaagaag
 481 atggcaaatc actctgagaa ggtttatgtg aatgtggcac accttggagg tctccaggaa
 541 aaatattctg aaaggctcta cagtcacaac cacaactttg tgaaggccat caattctgtt
 601 cagaagtctt ggactgcaac cacctatgaa gaatatgaga aactgagcat acgagatttg
 661 ataaggagaa gtggccacag cggaaggatc ctaaggccca aacctgcccc gataactgat
 721 gaaatacagc aacaaatttt aagtttgcca gaatcttggg actggagaaa cgtccgtggc
 781 atcaattttg ttagccctgt tcgaaaccaa gaatcttgtg gaagctgcta ctcatttgcc
 841 tctctgggta tgctagaagc aagaattcgt atattaacca acaattctca gaccccaatc
 901 ctgagtcctc aggaggttgt atcttgtagc ccgtatgccc aaggttgtga tggtggattc
 961 ccatacctca ttgcaggaaa gtatgcccaa gattttgggg tggtggaaga aaactgcttt
1021 ccctacacag ccacagatgc tccatgcaaa ccaaaggaaa actgcctccg ttactattct
1081 tctgagtact actatgtggg tggtttctat ggtggctgca atgaagccct gatgaagctt
1141 gagctggtca aacacggacc catggcagtt gccttttgaag tccacgatga cttcctgcac
1201 taccacagtg ggatctacca ccacactgga ctgagcgacc ctttcaaccc ctttgagctg
1261 accaatcatg ctgttctgct tgtgggctat ggaaaagatc cagtcactgg gttagactac
1321 tggattgtca agaacagctg gggctctcaa tggggtgaga gtggctactt ccggatccgc
1381 agaggaactg atgaatgtgc aattgagagt atagccatgg cagccatacc gattcctaaa
1441 ttgtaggacc tagctcccag tgtcccatac agcttttttat tattcacagg gtgatttagt
1501 cacaggctgg agactttttac aaagcaatat cagaagctta ccactaggta cccttaaaga
1561 attttgccct taagtttaaa acaatccttg atttttttct tttaatatcc tccctatcaa
1621 tcaccgaact acttttcttt ttaaagtact tggttaagta atacttttct gaggattggt
1681 tagatattgt caaatatttt tgctggtcac ctaaaatgca gccagatgtt tcattgttaa
1741 aaatctatat aaaagtgcaa gctgcctttt ttaaattaca taaatcccat gaatacatgg
1801 ccaaaatagt tatttttaa agactttaaa ataaatgatt aatcgatgct
```

INJURYMARKER6

INJURYMARKER6 is a 993 nucleotide sequence encoding hydroxysteroid sulfotransferase [D14989]:

```
  1  ggcaagggct ggaatactaa aagttattca tgatgtcaga atatacttgg tttgaaggaa    (SEQ ID NO:45)
 61  tacctttcc tgccttttgg ttttccaaag aaattctgga aaatagttgt aagaagtttg
121  tggtaaaaga agacgacttg atcatattga cttaccccaa gtcaggaacg aactggctga
181  tcgagattgt ctgcttgatt cagaccaagg gagatcccaa gtggatccaa tctatgccca
241  tctgggatcg ctcaccctgg atagagactg gttcaggata tgataaatta accaaaatgg
301  aaggaccacg actcatgacc tcccatcttc ccatgcatct tttctccaag tctctcttca
361  gttccaaggc caaggtgata tatctcatca gaaatcccag agatgttctt gtttctgctt
421  attttttctg gagtaagatc gccctggaga agaaaccaga ctcgctggga acttacgttg
481  aatggttcct caaaggaaat gttgcatatg gatcatggtt tgagcacatc cgtggctggc
541  tgtctatgag agaatgggac aacttcttgg tactgtacta tgaagacatg aaaaaggata
601  caatgggatc cataaagaag atatgtgact tcctgggaa aaaattagag ccagatgagc
661  tgaatttggt cctcaagtat agttccttcc aagtcgtgaa agaaaacaac atgtccaatt
721  atagcctcat ggagaaggaa ctgattctta ctggttttac tttcatgaga aaaggcacaa
781  ctaatgactg gaagaatcac ttcacagtag cccaagctga agcctttgat aaagtgttcc
841  aggagaaaat ggccggtttc cctccaggga tgttcccatg ggaataaatt ttcaaaagtt
901  ttaaatattt tatgaacact gatgtttatg tttatgttgt tctatgatgt ctgaataact
961  gaatgtgatc attgaataaa tcctgttgtg gat
```

INJURYMARKER7

INJURYMARKER7 is a 5001 nucleotide sequence encoding insulin-like growth factor binding protein [L22979]:

```
  1  cacaaaccca gcgagcattg aacactgcac acggccatct gcccagagag ctgtgaccac    (SEQ ID NO:46)
 61  cacttccgct actatctact cagaaagtcg tgactactga gccactgctg cctgcccaga
121  ttctcatcca ccgcctgctg cgtctggttg cgatgccgga gttcctaact gttgtttctt
181  ggccgttcct gatcctcctg tccttccagg ttcgcgtagt cgctggagcc ccccagccat
241  ggcactgtgc tccctgcact gctgagaggc tggagctctg tccacccgtg cctgcttcgt
301  gccccgagat ttctcggcct gcgggctgtg gctgctgccc gacatgtgcc ttgccactgg
361  gtgctgcctg tggtgtggcc actgcggcct gcgctcaggg actcagctgc cgtgcgctgc
421  caggggagcc tcgacctctg catgccctca cccgtggcca gggagcctgt gtactagaac
481  ctgccgcacc cgccacgagc agcttgtccg gttctcagca tgaaggtact acagccctct
541  ctgcctcttg atctcttggc taggacacac gtgctttcta ggcacgtcag aggcctatcc
601  ggaacctata gcagatagga caaaggctct ccatgcccac tttgagcttt cagcctcaaa
661  taaggccctc agttaggtcg tggcggcttg ggaaacacca gaggtgtcaa tccagtagca
721  gagtgggaa gttgggaaga atgttccaag ctcccagtgc agagtggaga gttgggaaga
781  atgttcacag actaggtagt actgatcctg cttggtcttt cagtggggag ggagctatgg
841  ggctgccagg tgggtgggt gctggcccaa acacctcttt ctgtgggtcc tgaccttggc
901  agttccaatg gctaaaaggt ccaggaaggt ttaggatggg agccctcctg ctgcccccag
```

-continued

```
 961   gaggtttgca atgtcctttg tagcatatat cctgccacac agtatgtgct tcccagatgt
1021   ttacagaaca taatgtgaaa atttaggccc aaaccttcac ttccattcat tgctatagac
1081   aaacagtgtt tgaagtgtat gttgcctgct aggagtctga caatcaggcg ctttcctgaa
1141   tttaagcact ggtttgtttg taataggaag cttgggaaat gcctcttcct ctgctccagc
1201   gggtatctcc cctgtctggg ctgcatgcac ttcctgtgtg gtaagggac  ctcatggttc
1261   catattctga cgggaagccg gactgcaggc atctgatcct tttgactaaa tggaagaact
1321   atcccaacgg tccttagaaa cgggcttccc caggagcgat gtctgataat gtcctcctct
1381   gtgagggct  gcctaagagg tgtcggtgtt caagaaagca gggctcccag aaaagaagag
1441   gatggtggtg tgaggtgggg aaggctacac tctacacctt gcttctcaac tatcccctta
1501   ctggggtctt acgagattct ttttgtggtg tggagaggag agctgagtgg tcaagtctca
1561   ccactaacgg gttcaagcct tggcctcagt ccttggcttc ttcaggatta catcctagac
1621   ccaactctct ctgccatggg gactcccttg cctaacccca aacatacca  tttccccaga
1681   aaggaattag tattgctaat tggtgataat tgttcccaaa tagcccactg gtgaaaacaa
1741   agcctgattt cacctgactg ttacagattg gtcttaaggc ggtagacgtg agtgacatag
1801   gagtgacacc tcagggctca tcgtctgtgt ctgtgggtt  cgttttcaga ggcaaaggct
1861   gctgtggcct ctgaggatga gcttgccgag agcccagaga tgacagagga acagctgctg
1921   gatagcttcc acctcatggc cccatcccgt gaggaccagc ccatcctgtg gaatgccatt
1981   agcacctaca gcagcatgcg ggcccgggag atcactgacc tcaagaaatg gaaggtgaga
2041   ccctgcactc agaccttcag gtttagctat ctacgtgaag aggtttgtct agacgatttc
2101   ttaaagggca ctgagcatgg ggctgagaac ggggatataa ctaccccat  ccctgatgta
2161   tttctgcctc cttaaaaata tggcaagtat ctcagagcat aaggtaggcc attttttcagt
2221   ctaggtttct ctgtcaccga gtacgcacgt tcagtgattg ttagccacca accagctcca
2281   cggttttgcc agcctttagc tatgcacttt agctatgcag taaacttctc tagctttact
2341   ggctgttttt caacttgacc acttgggga  gacagagaac caaggtgga  gagaaagtac
2401   ggcagaggca ttgaagaagt acacctaagg aaatgaaagg ataaacattg ttaggggcac
2461   tttagaattt catatggaaa ttgtccaaat cagtgccttg ttccgtaatc aatttgacat
2521   acaccaaatg caaggatggc tgtttgaaaa atctaggcat ttatgatgct aaattccaca
2581   cacagagact gagcctgtct ttttttattag agttcaggtg ctcaagttat tcagagatag
2641   ccagggtcag gaagcattta taccattggc caggctctta ccacaatgtc gttaagggg
2701   tctccagaaa atgccactga gggaggatga gagtggtgtc cctgtccttt atctacatag
2761   cccaagccag agaccaacct gtcctgctca cagatgggga aacatctcag ccgttgtcta
2821   aattgataat ttttgtctct tgtactcatg ctaatataaa attatccttt taggagccct
2881   gccaacggga actctataaa gtgttagaga gattagctgc cgctcaacag aaagcaggag
2941   atgagatcta caaattttat ctgccaaact gcaacaagaa tggatttttat cacagcaaac
3001   aggtaggtgg ctttgctcat ccagatcctt gtaaaacttc atgattttt  ttttttaaagt
3061   caaatgattc acaggcccaa tacacatcat gggtagcttt cttaggtgag atccagccct
3121   gcagtagttg ggagaagcta gtcctgagaa agagatagtg tgatggatga ggaacacttc
3181   agccagaagg gaggactaag cattagtgtg atgagtgagg agcacttcag ttaacaggga
3241   ggactaagca ttagtgtgat gagtgaggac cacttcaagc cagagggagg actaacattg
3301   gcagtatgat gagtgaggag cacttcagcc agtagggagg actaaccatt agtctcatca
```

-continued

```
3361 ctaggagcac ctcagccaag tagggaggac taaccattag tctcacactc acccaacatc
3421 ttcagtcagg actaagcatt agtgtgatga gtgaggagca cttcagtcag tagggaggac
3481 tacattagtg tgatgagtga ggagcacttc agccagtagg gaggactaac cgttcactca
3541 gattagcaga gatggatgtt ccatatactg atgtccaggt ttcagttcct cacaactaga
3601 ggaaagggac acagtcagtg taggagacag atgtatcgcg ttctctcttc ccacaaataa
3661 aaacaaactc tgtagtaaga cacaccaatt gtgctttgcc tagcaataaa tgagattgaa
3721 gaagtccagg cttaatttcg acgcaacttt agaactcagg gaagtgcaag ttctggaatt
3781 tcattgagga aaaacttgag gtctaggtct agccgtgtgg tagagatggt gagacctatc
3841 gttgagctcc tttggcagag ggccatggag caggtaaccg tcaaaacaat ataccactga
3901 gtaaacagat gagattgtta tcaggtgtgc cataaagcca acctctccgt tttgtgatga
3961 caaccagaag ggcattggtc tgccgagcct tagccagcag gtagctgtgc agtgcttggc
4021 ctcactgagg gacagggtgg ccagagctct tacctcctgc tgctcttgac ctcggtcctg
4081 tctttgcagt gcgagacatc tctggatgga gaagctgggc tctgctggtg tgtctaccca
4141 tggagtggga agaagatccc tggatctctg gagaccagag gggaccccaa ctgccaccag
4201 tattttaatg tgcaaaactg aaagttgttt cctccctcct tcttcacaca aaatatttaa
4261 gtatatagtg tatttatact ccggagcaca ccattttata tatgtgtata tgtatatatc
4321 caggaactag tttttatact ccacatgctg cttgatgtac aagtgggttt gtatttattc
4381 actctaagtt tatttttttc taccctgtcc ttgtgctgta ttaatttata taactgaagc
4441 ttttctcatc tccatacatg taaatactac catctcagct cttccagagt tctgctttga
4501 aagggcagcg cggtacgtgc ctagaacgag cacaagtcag tctgaggtag gggccttca
4561 gtgggttcag ggaggaaggt tagccctggc tcggggagac ttcctcatcg aatcccacag
4621 gtctgtgtct gatgcctatt ggctgggaag gttccgatgt tggttgtgta atcaaagcta
4681 aagctggaaa gctgcgtccc atgcactgtt aaacacacgt ctggaatccc acattctacc
4741 tggaaacact gctgtctctg tggaattcca gctctgtgct cattccctca gtccgttcgg
4801 cttcccgct cgcctgattc ctgggtctgt gctttgggga tagatgttgc aatacagggt
4861 gcttgtttgt ttacagaaca ccctggacaa acactctgtg actttatggt cccatttca
4921 agcagcatca ggcctctgtc tgggccagac tacagagccc ctcctccttg gtccatctcc
4981 ctttcttccc agggccctca g
```

INJURYMARKER8

INJURYMARKER8 is 579 bp rat expressed sequence tag (EST) [AA851963]. The acid was initially identified in a cloned fragment having the following sequence:

```
1   TGTACATAATTTATTAAAAATGTCTCTGACACAAATAATGACTCCACTGCATACATAGTTGGTGTTCAAAAATTTCCCCA    (SEQ ID NO:13)

81  ATGTTTGTTCTGGACACAATTGTTATTAGCCAACTCGGTGAATTCAAGACATTGTTCCACACAATGAACAATCGCACACA

161 TGAGAACTGCACCTAGAATGTCCATCCTAGAATCTCCATCCATCCAGTCAAAGTGCTGAGCTCACTGACTGAAGGAAACA

241 TGACCTGTGTTCTAGA
```

The cloned sequence was assembled into a contig resulting in the following consensus sequence:

```
  1  TGTACATAATTTATTAAAAATGTCTCTGACACAAATAATGACTCCACTGCATACATAGTTGGTGTTCAAAAATTTCCCCA   (SEQ ID NO:14)

81  ATGTTTGTTCTGGACACAATTGTTATAAGCCAACTCGGTGAATTCAAGACATTGTTCCACACAATGAACAATCGCACACA

161  TGAGAACTGCACCTACAATGTCCATCCTAGAATCTCCATCCATCCAGTCAAAGTGCTGAGCTCACTGACTGAAGGAAACA

241  TGACCTGTGTTCTAGAACGTAGCTGGCTATGAAGTTTACTCATGTGTAAATTCCTTAAAAAGATTAAATTGTTTGGCCCA

321  TTTCTATATTTCATAAAATAACTATAATTACAAACTTTCTAAAAATAATTTTACAACCATGTAATTATGACTAACCATAT

401  CATCTAAAAAGTAAGTGAAGTCATTGTCCTAGAGATTGTCTGAGATTATTCTGCTGAGAAGCTTACTTCAAACTCTTATC

481  ACTACTTCCTACTTCCAGTGTCCTTGAATTAAGAACAGAAATTGTAACTATGCTATTCTACATCAGATTGACACAACCTA

561  CTTCTAAGTACACTATTGC
```

Blast-N Results:
>gb:GENBANK-ID:AA851963|acc:AA851963 20
EST194732 Normalized rat spleen, Bento Soares Rattus sp.
cDNA clone RSPA086 3' end, mRNA sequence—Rattus sp.,
538 bp (RNA).
Top Previous Match Next MatCh
  Length=538
Plus Strand HSPs:

```
Score = 2681 (402.3 bits), Except = 8.1e-115, p = 8.1e-115
Identities = 537 538 (99%), Positives = 537/538 (99%), Strand = Plus/Plus Query:     42  CTCCACTGCATACATAGTTGGTGTTCAAAAATTTCCCCAATGTTTGTTCTGGACACAATT   101  (SEQ ID NO:47)
               ||||||||||||||||||||||||||||||||||||||||||||||||||||||||||||
Sbjct:      1  CTCCACTGCATACATAGTTGGTGTTCAAAAATTTCCCCAATGTTTGTTCTGGACACAATT    60  (SEQ ID NO:48)

Query:    102  GTTATAAGCCAACTCGGTGAATTCAAGACATTGTTCCACACAATGAACAATCGCACACAT   161
               ||||| ||||||||||||||||||||||||||||||||||||||||||||||||||||||
Sbjct:     61  GTTATTAGCCAACTCGGTGAATTCAAGACATTGTTCCACACAATGAACAATCGCACACAT   120

Query:    162  GAGAACTGCACCTAGAATGTCCATCCTAGAATCTCCATCCATCCAGTCAAAGTGCTGAGC   221
               ||||||||||||||||||||||||||||||||||||||||||||||||||||||||||||
Sbjct:    121  GAGAACTGCACCTAGAATGTCCATCCTAGAATGTCCATCCATCCAGTCAAAGTGCTGAGC   180

Query:    222  TCACTGACTGAAGGAAACATGACCTGTGTTCTAGAACGTAGCTGGCTATGAAGTTTACTC   281
               ||||||||||||||||||||||||||||||||||||||||||||||||||||||||||||
Sbjct:    181  TCACTGACTGAAGGAAACATGACCTGTGTTCTAGAACGTAGCTGGCTATGAAGTTTACTC   240

Query:    282  ATGTGTAAATTCCTTAAAAAGATTAAATTGTTTGGCCCATTTCTATATTTCATAAAATAA   341
               ||||||||||||||||||||||||||||||||||||||||||||||||||||||||||||
Sbjct:    241  ATGTGTAAATTCCTTAAAAAGATTAAATTGTTTGGCCCATTTCTATATTTCATAAAATAA   300

Query:    342  CTATAATTACAAACTTTCTAAAAATAATTTTACAACCATGTAATTATGACTAACCATATC   401
               ||||||||||||||||||||||||||||||||||||||||||||||||||||||||||||
Sbjct:    301  CTATAATTACAAACTTTCTAAAAATAATTTTACAACCATGTAATTATGACTAACCATATC   360

Query:    402  ATCTAAAAAGTAAGTGAAGTCATTGTCCTAGAGATTGTCTGAGATTATTCTGCTGAGAAG   461
               ||||||||||||||||||||||||||||||||||||||||||||||||||||||||||||
Sbjct:    361  ATCTAAAAAGTAAGTGAAGTCATTGTCCTAGAGATTGTCTGAGATTATTCTGCTGAGAAG   420

Query:    462  CTTACTTCAAACTCTTATCACTACTTCCTACTTCCAGTGTCCTTGAATTAAGAACAGAAA   521
               ||||||||||||||||||||||||||||||||||||||||||||||||||||||||||||
Sbjct:    421  CTTACTTCAAACTCTTATCACTACTTCCTACTTCCAGTGTCCTTGAATTAAGAACAGAAA   480

Query:    522  TTGTAACTATGCTATTCTACATCAGATTGACACAACCTACTTCTAAGTACACTATTGC    579
               ||||||||||||||||||||||||||||||||||||||||||||||||||||||||||
Sbjct:    481  TTGTAACTATGCTATTCTACATCAGATTGACACAACCTACTTCTAAGTACACTATTGC    538
```

INJURYMARIKER9

INJURYMARKER9 is a 2495 nucleotide catalese-encoding sequence[M11670], having the following nucleic acid sequence:

```
   1   attgcctacc ccgggtggag accgtgctcg tccggccctc ttgcctcacg ttctgcagct     (SEQ ID NO:49)
  61   ctgcagctcc gcaatcctac accatggcgg acagccggga cccagccagc gaccagatga
 121   agcagtggaa ggagcagcgg cccctcaga aacccgatgt cctgaccacc ggaggcggga
 181   acccaatagg agataaactt aatatcatga ctgcggggcc ccgagggccc ctcctcgttc
 241   aagatgtggt tttcaccgac gagatggcac actttgacag agagcggatt cctgagagag
 301   tggtacatgc aaagggagca ggtgcttttg gatactttga ggtcacccac gatattacca
 361   gatactccaa ggcaaaggtg tttgagcata ttgggaagag gactcctatt gccgtccgat
 421   tctccacagt cgctggagag tcaggctcag ctgacacagt tcgtgaccct cgtgggtttg
 481   cagtgaaatt ctacactgaa gatggtaact gggacctcgt gggaaacaac acccctattt
 541   tcttcatcag ggatgccatg ttgtttccat cctttatcca tagccagaag agaaacccac
 601   aaactcacct gaaggaccct gacatggtct gggacttctg gagtctttgt ccagagtctc
 661   tccatcaggt tactttcttg ttcagcgacc gagggattcc agatggacat cggcacatga
 721   atggctatgg ctcacacacc ttcaagctgg ttaatgcgaa tggagaggca gtgtactgca
 781   agttccatta caagactgac cagggcatca aaaacttgcc tgttgaagag gcaggaagac
 841   ttgcacagga agacccggat tatggcctcc gagatctttt caatgccatc gccagtggca
 901   attacccatc ctggactttt tacatccagg tcatgacttt caaggaggca gaaaccttcc
 961   catttaatcc atttgacctg accaaggttt ggcctcacaa ggactaccct cttataccag
1021   ttggcaaact ggtcttaaac agaaatcctg ctaattattt tgctgaagtt gaacagatgg
1081   cttttgaccc aagcaacatg ccccctggca ttgagcccag cccggacaag atgctccagg
1141   gccgcctttt tgcttaccca gacactcacc gccaccgcct gggaccaaac tatctgcaga
1201   tacctgtgaa ctgtccctac cgtgctcgcg tggccaacta ccagcgcgat ggccccatgt
1261   gcatgcatga caaccagggt ggtgctccca actactaccc caacagcttc agcgcaccag
1321   agcagcaggg ctcggccctg gagcaccata gccagtgctc tgcagatgtg aagcgcttca
1381   acagtgctaa tgaagacaac gtcactcagg tgcggacatt ctatacgaag gtgttgaatg
1441   aggaggagag gaaacgcctg tctgagaaca ttgccaacca cctgaaagat gctcagcttt
1501   tcattcgaga gaaagcggtc aagaatttca ctgacgtcca ccctgactac ggggcccgag
1561   tccaggctct tctggaccag tacaactccc agaagcctaa gaatgcaatt cacacctacg
1621   tacaggccgg ctctcacata gctgccaagg gaaaagctaa cctgtaaagc acgggtgctc
1681   agcctcctca gcctgcactg aggagatccc tcatgaagca gggcacaagc ctcaccagta
1741   atcatcgctg gatggagtct cccctgctga agcgcagact cacgctgacg tctttaaaac
1801   gataatccaa gcttctagag tgaatgatag ccatgctttt gatgacattt cccgagggg
1861   aaattaaaga ttagggctta gcaatcactt aacagaaaca tggatctgct taggacttct
1921   gtttggatta ttcatttaaa atgattacaa gaaaggtttt ctagccagaa acatgatttg
1981   attagatatg atatatgata aaatcttggt gattttacta tagtcttatg ttacctcaca
2041   gaatggtata tatacaacac acacacacac acacacacac acaccaaa acacacatac
2101   actatacaca acacacacac acacacataa aacacacata cacaacacac acatacacta
2161   cacacacaga acacacaaca caaacataca cacataggca cacacacaca cacacacaca
```

-continued

```
2221  cacacacaca cacacacaca cacacatgaa tgaagggatt ataaagatgg cccacccaga
2281  attttttttt atttttctaa gatccttata agaaaaacca tacttggatc atgtcttcca
2341  aaaataactt tagcactgtt gaaacttaat gtttattcct gtgtagttga ttggattcct
2401  tttcccttg  aaattatgtt tatgctgata cacagtgatt tcacataggg tgatttgtat
2461  ttgcttacat ttttacaata aaatgatctt catgg
```

INJURYMARKER10

INJURYMARKER10 is a 1884 nucleotide betaine homocysteine methyl transferase-encoding sequence [AF038870]:

```
   1  caagcctttg ctggagaccg ctcctgtcca gtccgcagct ggcttcagcg ccactcagga    (SEQ ID NO:50)
  61  caccggaaag atggcaccga ttgccggcaa gaaggccaag agggggaatct tagaacgctt
 121  aaatgctggc gaagtcgtga tcggagatgg gggatttgtc tttgcactgg aaaagagggg
 181  ctacgtaaag gctggaccct ggaccccaga ggctgcggtg agcacccccg aggcagttcg
 241  gcagcttcat cgggagttcc tcagagctgg atcgaacgtc atgcagacct tcactttcta
 301  tgcaagtgag acaagctgga aaaccgagg  gaactacgtg cagagaaga  tatctgggca
 361  gaaggtcaat gaagctgctt gtgacattgc acggcaagtt gctgacgaag gggatgcatt
 421  ggttgcagga ggtgtgagtc agacaccttc ctacctcagc tgcaagagtg agacggaagt
 481  taaaaagata tttcaccaac agcttgaggt cttcatgaag aagaatgtgg acttcctcat
 541  tgcagagtat tttgaacatg ttgaagaagc cgtgtgggca gtcgaggcct taaaaacatc
 601  cgggaagctt atagcggcta ccatgtgcat cggacctgaa ggagatctac atggcgtgtc
 661  tcctggagag tgcgcagtgc gtttggtaaa agcaggtgcc gccattgtcg gtgtgaactg
 721  ccacttcgac cccagcacca gcttgcagac aataaagctc atgaaggagg gtctggaagc
 781  agctcggctg aaggcttact tgatgagcca cgccctggcc taccacaccc ctgactgtgg
 841  caaacaggga tttattgatc tcccagaatt ccccttt gga ttggaaccca gagttgccac
 901  cagatgggat attcaaaaat acgccagaga ggcctacaac ctgggggtca gtacattgg
 961  cggctgctgc ggatttgagc cctaccacat cagggccatt gcagaggagc tcgccccaga
1021  aaggggattt ttaccaccag cttcagaaaa acatggcagc tggggaagtg gtttggacat
1081  gcacaccaaa ccctggatca gggcaagggc caggaaagaa tactggcaga atcttcgaat
1141  agcttcgggc agaccgtaca atccttcgat gtccaagccg gatgcttggg gagtgacgaa
1201  aggggcagca gagctgatgc agcagaagga agccaccact gagcagcagc tgagagcgct
1261  cttcgaaaaa caaaaattca aatccgcaca gtagccacag gccagcggtt cggggcgaat
1321  tcctccaggt ccgggccaca gtgtgcaccc ggaaggagaa ggcatctcta aaccagcgtt
1381  tgtgttgatg ccggcttaca cctgtgattg gtgctagtta gacaaaatgg agtcacagat
1441  agcatttcac agttacaaaa ctacgcttta gaattttacc tagaaggaag aaaggagaag
1501  tccacagtaa atcctgaaca catttcctac gtgcctgtcg cattacaggc gcacaggagt
1561  cactgcagcg aagagaaagt cacccgacgt caatctcatt tcagataggg ggataggaca
1621  ccacctccac gagtgacata gaaccattca gggaccgtat cataagtgac acagcaacca
1681  tctatatcta agatgcttcc caagtggatt ccaagatctt tgagcagga cccttaggca
1741  gaaacaacac acaccagccc tgtaaaactt aacagataac tgatccattc tgtaattctg
```

```
1801  taatctctgt tctgactgct tccattccat ttcattaata aaaacatgcc ggttgaaaac
1861  cttcaaaaaa aaaaaaaaaa aaa
```

Principle components analysis was used to generate three eigenvectors used to transform the original expression level data matrix, as shown in Table 6 below. Eigenvector 1 values represent NSAIDs associated with hepatoxicity involving hepatocellular damage, Eigenvector 2 values represent NSAIDs associated with hepatoxicity involving cholestasis, and Eigenvector 3 values represent NSAIDs associated with hepatoxicity involving elevated transaminase level.

TABLE 6

Transform Eigenvectors for Hepatoxicity by Injury Type

| Gene | Eigenvector 1 | Eigenvector 2 | Eigenvector 3 |
| --- | --- | --- | --- |
| INJURYMARKER 1 | 58.7 | 0.325 | −15.2 |
| INJURYMARKER 2 | 205 | −3.23 | 3.01 |
| INJURYMARKER 3 | −16.9 | −6.52 | −2.09 |
| INJURYMARKER 4 | −10.3 | 0.351 | −1.45 |
| INJURYMARKER 5 | −7.59 | −0.152 | −0.310 |
| INJURYMARKER 6 | 11.4 | −2.69 | 2.49 |
| INJURYMARKER 7 | −16.0 | −1.57 | 8.71 |
| INJURYMARKER 8 | −11.6 | 1.13 | 5.36 |
| INJURYMARKER 9 | −11.0 | −0.351 | 0.078 |
| INJURYMARKER 10 | 7.55 | 0.618 | 4.65 |
| % of variation explained | 99.0 | 0.7 | 0.3 |

These eigenvectors may be used to transform the expression levels of INJURYMARKERS 1–10 ("INJURYMARKERS") in response to a given drug, in order to predict that drug's hepatotoxicity injury type. For example, expression levels of INJURYMARKERS correlating with Eigenvector 1 indicates that the test drug has a risk of hepatotoxicity involving hepatocellular damage. Alternatively, a drug's INJURYMARKERS expression profile can be generated simultaneously with the above-described training set (or an equivalent set) run in parallel with the test drug, and expression levels associated with the test drug directly compared to those of the training set.

General Methods

The RISKMARKER (i. e. RISKMARKERS 1–8) and INJURYMARKER (i e. INJURYMARKERS 1–10) nucleic acids and encoded polypeptides can be identified using the information provided above. In some embodiments, the RISKMARKER or INJURYMARKER nucleic acids and polypeptide correspond to nucleic acids or polypeptides which include the various sequences (referenced by SEQ ID NOs) disclosed for each RISKMARKER or INJURYMARKER polypeptide.

In its various aspects and embodiments, the invention includes providing a test cell population which includes at least one cell that is capable of expressing one or more of the sequences RISKMARKER 1–8 or INJURYMARKER 1–10. By "capable of expressing" is meant that the gene is present in an intact form in the cell and can be expressed. Expression of one, some, or all of the RISKMARKER or INJURYMARKER sequences is then detected, if present, and, preferably, measured. Using sequence information provided by the database entries for the known sequences, or the sequence information for the newly described sequences, expression of the RISKMARKER or INJURYMARKER sequences can be detected (if present) and measured using techniques well known to one of ordinary skill in the art. For example, sequences within the sequence database entries corresponding to RISKMARKER or INJURYMARKER sequences, or within the sequences disclosed herein, can be used to construct probes for detecting RISKMARKER or INJURYMARKER RNA sequences in, e.g., northern blot hybridization analyses or methods which specifically, and, preferably, quantitatively amplify specific nucleic acid sequences. As another example, the sequences can be used to construct primers for specifically amplifying the RISKMARKER or INJURYMARKER sequences in, e.g., amplification-based detection methods such as reverse-transcription based polymerase chain reaction. When alterations in gene expression are associated with gene amplification or deletion, sequence comparisons in test and reference populations can be made by comparing relative amounts of the examined DNA sequences in the test and reference cell populations.

Expression can be also measured at the protein level, i.e., by measuring the levels of polypeptides encoded by the gene products described herein. Such methods are well known in the art and include, e.g., immunoassays based on antibodies to proteins encoded by the genes.

Expression level of one or more of the RISKMARKER or INJURYMARKER sequences in the test cell population, e.g. rat hepatocytes, is then compared to expression levels of the sequences in one or more cells from a reference cell population. Expression of sequences in test and control populations of cells can be compared using any art-recognized method for comparing expression of nucleic acid sequences. For example, expression can be compared using GENECALLING® methods as described in U.S. Pat. No. 5,871,697 and in Shimkets et al., Nat. Biotechnol. 17:798–803.

In various embodiments, the expression of one or more sequences which are markers of hepatoxicity risk, i.e. RISKMARKERS 1–8, is compared. In other embodiments, the expression of one or more sequences which are markers of hepatoxicity injury type, ie. INJURYMARKERS, is compared. In further embodiments, expression of one or more RISKMARKERS and INJURYMARKERS may be compared to predict both hepatoxicity risk and type of hepatoxicity injury.

In various embodiments, the expression of 2, 3, 4, 5, 6, 7, 8, 9, 10, 15, or all of the sequences represented by RISKMARKER 1–8 and INJURYMARKER 1–10 are measured. If desired, expression of these sequences can be measured along with other sequences whose expression is known to be altered according to one of the herein described parameters or conditions.

The reference cell population includes one or more cells for which the compared parameter is known. The compared parameter can be, e.g., hepatotoxic agent expression status. By "hepatotoxic agent expression status" is meant that it is known whether the reference cell has had contact with a hepatotoxic agent. An example of a hepatotoxic agent is, e.g., a thiazolidinedione such as troglitazone. Whether or not comparison of the gene expression profile in the test cell population to the reference cell population reveals the presence, or degree, of the measured parameter depends on the composition of the reference cell population. For example, if the reference cell population is composed of cells that have not been treated with a known hepatotoxic agent, a similar gene expression level in the test cell population and a reference cell population indicates the test agent is not a hepatotoxic agent. Conversely, if the reference cell population is made up of cells that have been treated with a hepatotoxic agent, a similar gene expression profile between the test cell population and the reference cell population indicates the test agent is a hepatotoxic agent.

In various embodiments, a RISKMARKER or INJURYMARKER sequence in a test cell population is considered comparable in expression level to the expression level of the RISKMARKER or INJURYMARKER sequence if its expression level varies within a factor of 2.0, 1.5, or 1.0 fold to the level of the RISKMARKER or INJURYMARKER transcript in the reference cell population. In various embodiments, a RISKMARKER or INJURYMARKER sequence in a test cell population can be considered altered in levels of expression if its expression level varies from the reference cell population by more than 1.0, 1.5, 2.0 or more fold from the expression level of the corresponding RISKMARKER or INJURYMARKER sequence in the reference cell population.

Alternatively, the absolute expression level matrix of the 8 RISKMARKER and/or 10 INJURYMARKER fragments in a test cell can be transformed using the principal component eigenvectors described above, or similar eigenvalues generated from parallel dosed members of the training set as internal controls. The expression eigenvalues for the test cell can then be compared to the training set eigenvalues described herein, or a parallel-run training set, if any.

The RISKMARKER expression level combination is considered similar to Low Risk idiosyncratic NSAIDS (several of which have been withdrawn), if the test drug's expression profile is within the 95% confidence interval (CI) of the centroid of that risk class. See Table 4. The test drug is considered Very Low Risk idiosyncratic if the transformed expression profile falls within the 95% CI of the centroid of that class. The test drug is considered Overdose Risk if the expression profile falls within the 95% CI of the centroid of that class. If the compound fails to associate with any of these compounds it will be categorized as unclassifiable.

Similarly, the INJURYMARKER expression level combination is considered indicative of hepatocellular damage induced by idiosyncratic NSAIDS, if the test drug's expression profile is within the 95% confidence interval (CI) of the centroid of that injury type. See Table 6. The test drug is considered to induce idiosyncratic cholestasis if the transformed expression profile falls within the 95% CI of the centroid of that injury type. The test drug is considered to induce elevated transaminase level if the expression profile falls within the 95% CI of the centroid of that class. If the compound fails to associate with any of these compounds it will be categorized as unclassifiable.

If desired, comparison of differentially expressed sequences between a test cell population and a reference cell population can be done with respect to a control nucleic acid whose expression is independent of the parameter or condition being measured. Expression levels of the control nucleic acid in the test and reference nucleic acid can be used to normalize signal levels in the compared populations.

In some embodiments, the test cell population is compared to multiple reference cell populations. Each of the multiple reference populations may differ in the known parameter. Thus, a test cell population may be compared to a first reference cell population known to have been exposed to a hepatotoxic agent, as well as a second reference population known have not been exposed to a hepatotoxic agent.

The test cell population that is exposed to, i.e., contacted with, the test hepatotoxic agent can be any number of cells, i.e., one or more cells, and can be provided in vitro, in vivo, or ex vivo.

In other embodiments, the test cell population can be divided into two or more subpopulations. The subpopulations can be created by dividing the first population of cells to create as identical a subpopulation as possible. This will be suitable, in, for example, in vitro or ex vivo screening methods. In some embodiments, various sub populations can be exposed to a control agent, and/or a test agent, multiple test agents, or, e.g., varying dosages of one or multiple test agents administered together, or in various combinations.

Preferably, cells in the reference cell population are derived from a tissue type as similar as possible to test cell, e.g., liver tissue. In some embodiments, the control cell is derived from the same subject as the test cell, e.g., from a region proximal to the region of origin of the test cell. In other embodiments, the reference cell population is derived from a plurality of cells. For example, the reference cell population can be a database of expression patterns from previously tested cells for which one of the herein-described parameters or conditions (hepatotoxic agent expression status is known.

The test agent can be a compound not previously described or can be a previously known compound but which is not known to be a hepatotoxic agent.

The subject is preferably a mammal. The mammal can be, e.g., a human, non-human primate, mouse, rat, dog, cat, horse, or cow.

Screening for Toxic Agents

In one aspect, the invention provides a method of identifying toxic agents, e.g., hepatotoxic agents. The hepatotoxic agent can be identified by providing a cell population that includes cells capable of expressing one or more nucleic acid sequences homologous to those of RISKMARKER 1–8 or INJURYMARKER 1–10. The sequences need not be identical to sequences including RISKMARKER or INJURYMARKER nucleic acid sequences, as long as the sequence is sufficiently similar that specific hybridization can be detected. Preferably, the cell includes sequences that are identical, or nearly identical to those identifying the RISKMARKER or INJURYMARKER nucleic acids described herein.

Expression of the nucleic acid sequences in the test cell population is then compared to is the expression of the nucleic acid sequences in a reference cell population, which is a cell population that has not been exposed to the test agent, or, in some embodiments, a cell population exposed the test agent. Comparison can be performed on test and reference samples measured concurrently or at temporally distinct times. An example of the latter is the use of compiled expression information, e.g., a sequence database, which assembles information about expression levels of known sequences following administration of various agents. For example, alteration of expression levels following administration of test agent can be compared to the expression changes observed in the nucleic acid sequences following administration of a control agent, e.g. a NSAID such as ketoprofen.

An alteration in expression of the nucleic acid sequence in the test cell population compared to the expression of the nucleic acid sequence in the reference cell population that has not been exposed to the test agent indicates the test agent is a hepatotoxic agent.

The invention also includes a hepatotoxic agent identified according to this screening method.

In some embodiments of the method of the invention, the test agent is an idiosyncratic hepatotoxic agent, e.g. a NSAID, and the reference agent is also a NSAID. As described above, RISKMARKER (e.g. RISKMARKERS 1–8) expression level patterns can be used to predict the level of hepatoxicity risk (i.e. low, very low, or overdose) associated with a given test agent, e.g. a NSAID. In one embodiment, the reference NSAID (ie. used with the reference cell population) is a NSAID classified as having a low risk of hepatoxicity. The test agent is then identified as having a low risk of hepatoxicity if no qualitative difference in expression levels is identified in comparison to expression levels in the reference population exposed to a low risk NSAID. In certain embodiments, the low risk NSAID is Benoxaprofen, Bromfenac, Diclofenac, Phenylbutazone, or Sulindac. In another embodiment, the reference NSAID is a NSAID classified as having a very low risk of hepatoxicity. The test agent is then identified as having a very low risk of hepatoxicity if no qualitative difference in expression levels is identified in comparison to expression levels in the reference population exposed to a very low risk NSAID. In certain embodiments, the very low risk NSAID is Etodolac, Fenoprofen, Flurbiprofen, Ibuprofen, Indomethacin, Ketoprofen, Meclofenamate, Mefenamic Acid, Nabumetone, Naproxen, Oxaprozin, Piroxicam, Suprofen, Tenoxicam, Tolmentin, or Zomepirac. In still another embodiment, the reference NSAID is a NSAID classified as having an overdose risk of hepatoxicity. The test agent is then identified as having an overdose risk of hepatoxicity if no qualitative difference in expression levels is identified in comparison to expression levels in the reference population exposed to an overdose risk NSAID. In certain embodiments, the overdose risk NSAID is Acetaminophen, Acetylsalicylic acid, or Phenacetin. In some embodiments, the difference in expression levels is determined by comparing expression transformation eigenvectors (for risk class) for the test cell and reference cell populations, as described above.

As also described above, INJURYMARKER (e.g. INJURYMARKERS 1–10) expression level patterns can be used to predict the type of hepatoxicity injury (i.e. hepatocellular damage, cholestasis, or elevated transaminase level) associated with a given test agent, e.g. a NSAID. In some embodiments, the reference NSAID is a NSAID classified as inducing hepatocellular damage. The test agent is then identified as likely to induce hepatocellular damage if no qualitative difference in expression levels is identified in comparison to expression levels in the reference population exposed to a NSAID:) which induces hepatocellular damage. In certain embodiments, the hepatocellular damage inducing NSAID is Acetaminophen, Flurbiprofen, or Ketoprofen. In another embodiment, the reference NSAID is a NSAID classified as inducing cholestasis. The test agent is then identified as likely to induce cholestasis if no qualitative difference in expression levels is identified in comparison to expression levels in the reference population exposed to a NSAID which induces cholestasis. In certain embodiments, the cholestatis-inducing NSAID is Benoxaprofen, Nabumetone, or Sulindac. In yet another embodiment, the reference NSAID is a NSAID classified as inducing elevated transaminase level. The test agent is then identified as likely to induce elevated transaminase level if no qualitative difference in expression levels is identified as compared to expression levels in the reference population exposed to a NSAID which induces elevated transaminase levels. In certain embodiments, the elevated transaminase level inducing NSAID is Zomepirac, Mefenamic acid, or Tenoxicam. In some embodiments, the difference in expression levels is determined by comparing expression transformation eigenvectors for said test cell and reference cell populations, as described above.

Assessing Toxicity of a Toxic Agent in a Subject

The differentially expressed RISKMARKER or INJURYMARKER sequences identified herein also allow for the hepatotoxicity of a hepatotoxic agent to be determined or monitored. In this method, a test cell population from a subject is exposed to a test agent, ie. a. hepatotoxic agent. If desired, test cell populations can be taken from the subject at various time points before, during, or after exposure to the test agent. Expression of one or more of the RISKMARKER or INJURYMARKER sequences in the cell population is then measured and compared to a reference cell population which includes cells whose hepatotoxic agent expression status is known. Preferably, the reference cells not been exposed to the test agent.

If the reference cell population contains no cells exposed to the treatment, a similarity in expression between RISKMARKER or INJURYMARKER sequences in the test cell population and the reference cell population indicates that the treatment is non-hepatotoxic. However, a difference in expression between RISKMARKER or INJURYMARKER sequences in the test population and this reference cell population indicates the treatment is hepatotoxic.

By "hepatotoxicity" is meant that the agent is damaging or destructive to liver when administered to a subject leads to liver damage.

As described in detail above, RISKMARKER expression patterns can be used to predict the level of hepatotoxicity risk (e.g. low risk, very low risk, overdose risk) associated with a test agent or drug, by comparison to RISKMARKER expression levels for reference drugs, e.g. NSAIDs, with a given classification of risk (e.g. very low risk). Similarly, INJURYMARKER expression patterns can be used to predict the type of hepatotoxicity damage (e.g. hepatocellular damage, cholestasis, elevated transaminase level) associated with a test agent or drug, by comparison to INJURYMARKER expression levels for reference drugs, e.g. NSAIDs, which induce a given type of hepatotoxic damage (e.g. cholestasis).

Riskmarker Nucleic Acids

Also provided in the invention are novel nucleic acid comprising a nucleic acid sequence selected from the group consisting of RISKMARKER 1, and RISKMARKERS 6–8, or their complements, as well as vectors and cells including these nucleic acids.

Thus, one aspect of the invention pertains to isolated RISKMARKER nucleic acid molecules that encode RISKMARKER proteins or biologically active portions thereof. Also included are nucleic acid fragments sufficient for use as hybridization probes to identify RISKMARKER-encoding nucleic acids (e.g., RISKMARKER mRNA) and fragments for use as polymerase chain reaction (PCR) primers for the amplification or mutation of RISKMARKER nucleic acid molecules. As used herein, the term "nucleic acid molecule"

is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt) or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules which are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (ie., sequences located at the 5' and 3' ends of the nucleic acid) in the genomic DNA of the organism from which the nucleic acid is derived. For example, in various embodiments, the isolated RISK-MARKER nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of any of RISKMARKER 1, or RISKMARKER 6–8, or a complement of any of these nucleotide sequences, can be isolated using standard molecular biology techniques and the sequence information provided herein. Using all or a portion of these nucleic acid sequences as a hybridization probe, RISKMARKER or INJURYMARKER nucleic acid sequences can be isolated using standard hybridization and cloning techniques (e.g., as described in Sambrook et al., eds., Molecular Cloning: A Laboratory Manual $2^{nd}$ Ed., Cold Spring Harbor Laboratory Press, Cold Spring Harbor, N.Y., 1989; and Ausubel, et al., eds., Current Protocols in Molecular Biology, John Wiley & Sons, New York, NY, 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotide corresponding to RISKMARKER nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having at least about 10 nt and as many as 50 nt, preferably about 15 nt to 30 nt. They may be chemically synthesized and may be used as probes.

In another embodiment, an isolated nucleic acid molecule of the invention comprises a nucleic acid molecule that is a complement of the nucleotide sequence shown in RISK-MARKER 1, or RISKMARKER 6–8. In another embodiment, an isolated nucleic acid molecule of the invention comprises a nucleic acid molecule that is a complement of the nucleotide sequence shown in any of these sequences, or a portion of any of these nucleotide sequences. A nucleic acid molecule that is complementary to the nucleotide sequence shown in RISKMARKER 1, or RISKMARKER 6–8 is one that is sufficiently complementary to the nucleotide sequence shown, such that it can hydrogen bond with little or no mismatches to the nucleotide sequences shown, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of RISKMARKER 1, or RISKMARKER 6–8, e.g., a fragment that can be used as a probe or primer or a fragment encoding a biologically active portion of RISKMARKER. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 45%, 50%, 70%, 80%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., Current Protocols in Molecular Biology, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482–489, which in incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a RISKMARKER polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a RISKMARKER polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding a human RISKMARKER protein. Homologous nucleic acid sequences include those nucleic acid sequences that encode conservative amino acid substitutions (see below) in a RISKMARKER polypeptide, as well as a polypeptide having a RISKMARKER activity. A homologous amino acid sequence does not encode the amino acid sequence of a human RISKMARKER polypeptide.

The nucleotide sequence determined from the cloning of human RISKMARKER genes allows for the generation of probes and primers designed for use in identifying and/or cloning RISKMARKER homologues in other cell types, e.g., from other tissues, as well as RISKMARKER homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of a nucleic acid comprising a RISKMARKER sequence, or an antisense strand nucleotide sequence of a nucleic acid comprising a RISKMARKER sequence, or of a naturally occurring mutant of these sequences.

Probes based on human RISKMARKER nucleotide sequences can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a RISKMARKER protein, such as by measuring a level of a RISKMARKER-encoding nucleic acid in a sample of cells from a subject e.g., detecting RISKMARKER mRNA levels or determining whether a genomic RISKMARKER gene has been mutated or deleted.

"A polypeptide having a biologically active portion of RISKMARKER" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of RISKMARKER" can be prepared by isolating a portion of RISKMARKER 1, or RISKMARKER 6–8, that encodes a polypeptide having a RISKMARKER biological activity, expressing the encoded portion of RISKMARKER protein (e.g., by recombinant expression in vitro) and assessing the activity of the encoded portion of RISKMARKER. For example, a nucleic acid fragment encoding a biologically active portion of a RISKMARKER polypeptide can optionally include an ATP-binding domain. In another embodiment, a nucleic acid fragment encoding a biologically active portion of RISKMARKER includes one or more regions.

Riskmarker and Injurymarker Variants

The invention further encompasses nucleic acid molecules that differ from the disclosed or referenced RISKMARKER or INJURYMARKER nucleotide sequences due to degeneracy of the genetic code. These nucleic acids thus encode the same RISKMARKER or INJURYMARKER protein as that encoded by nucleotide sequence comprising a RISKMARKER or INJURYMARKER nucleic acid as shown in, e.g., RISKMARKER 1–8 INJURYMARKER 1–10.

In addition to the rat RISKMARKER or INJURYMARKER nucleotide sequence shown in RISKMARKER or INJURYMARKER 1, and RISKMARKER or INJURYMARKER 6–8, it will be appreciated by those skilled in the art that DNA sequence polymorphisms that lead to changes in the amino acid sequences of a RISKMARKER or INJURYMARKER polypeptide may exist within a population (e.g., the human population). Such genetic polymorphism in the RISKMARKER or INJURYMARKER gene may exist among individuals within a population due to natural allelic variation. As used herein, the terms "gene" and "recombinant gene" refer to nucleic acid molecules comprising an open reading frame encoding a RISKMARKER or INJURYMARKER protein, preferably a mammalian RISKMARKER or INJURYMARKER protein. Such natural allelic variations can typically result in 1–5% variance in the nucleotide sequence of the RISKMARKER or INJURYMARKER gene. Any and all such nucleotide variations and resulting amino acid polymorphisms in RISKMARKER or INJURYMARKER that are the result of natural allelic variation and that do not alter the functional activity of RISKMARKER or INJURYMARKER are intended to be within the scope of the invention.

Moreover, nucleic acid molecules encoding RISKMARKER or INJURYMARKER proteins from other species, and thus that have a nucleotide sequence that differs from the human sequence of RISKMARKER OR INJURYMARKER, are intended to be within the scope of the invention. Nucleic acid molecules corresponding to natural allelic variants and homologues of the RISKMARKER or INJURYMARKER DNAs of the invention can be isolated based on their homology to the human RISKMARKER or INJURYMARKER nucleic acids disclosed herein using the human cDNAs, or a portion thereof, as a hybridization probe according to standard hybridization techniques under stringent hybridization conditions. For example, a soluble human RISKMARKER or INJURYMARKER DNA can be isolated based on its homology to human membrane-bound RISKMARKER or INJURYMARKER. Likewise, a membrane-bound human RISK- MARKER or INJURYMARKER DNA can be isolated based on its homology to soluble human RISKMARKER or INJURYMARKER.

Accordingly, in another embodiment, an isolated nucleic acid molecule of the invention is at least 6 nucleotides in length and hybridizes under stringent conditions to the nucleic acid molecule comprising the nucleotide sequence of RISKMARKER 1, or RISKMARKER 6–8. In another embodiment, the nucleic acid is at least 10, 25, 50, 100, 250 or 500 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding RISKMARKER or INJURYMARKER proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formarmide.

Stringent conditions are known to those skilled in the art and can be found in Current Protocols in Molecular Biology, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of RISKMARKER 1, or RISKMARKER 6–8 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of RISKMARKER 1, or RISKMARKER 6–8, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, Current Protocols in Molecular Biology, John Wiley & Sons, NY, and Kriegler, 1990, Gene Transfer and Expression, A Laboratory Manual, Stockton Press, NY.

In a third embodiment, a nucleic acid that is hybridizable to the nucleic acid molecule comprising the nucleotide sequence of RISKMARKER 1, or RISKMARKER 6–8, or fragments, analogs or derivatives thereof, under conditions of low stringency, is provided. A non-limiting example of low stringency hybridization conditions are hybridization in 35% formarmide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al (eds.), 1993, Current Protocols in Molecular Biology, John Wiley & Sons, NY, and Kriegler, 1990, Gene Transfer and Expression, A Laboratory Manual, Stockton Press, NY; Shilo et al., 1981, *Proc Natl Acad Sci USA* 78: 6789–6792.

Conservative Mutations

In addition to naturally-occurring allelic variants of the RISKMARKER sequence that may exist in the population, the skilled artisan will further appreciate that changes can be introduced into an RISKMARKER nucleic acid or directly into an RISKMARKER polypeptide sequence without altering the functional ability of the RISKMARKER protein. In some embodiments, the nucleotide sequence of RISKMARKER 1, or RISKMARKER 6–8 will be altered, thereby leading to changes in the amino acid sequence of the encoded RISKMARKER protein. For example, nucleotide substitutions that result in amino acid substitutions at various "non-essential" amino acid residues can be made in the sequence of RISKMARKER 1, or RISKMARKER 6–8. A "non-essential" amino acid residue is a residue that can be altered from the wild-type sequence of RISKMARKER without altering the biological activity, whereas an "essential" amino acid residue is required for biological activity. For example, amino acid residues that are conserved among the RISKMARKER proteins of the present invention, are predicted to be particularly unamenable to alteration.

In addition, amino acid residues that are conserved among family members of the RISKMARKER proteins of the present invention, are also predicted to be particularly unamenable to alteration. As such, these conserved domains are not likely to be amenable to mutation. Other amino acid residues, however, (e.g., those that are not conserved or only semi-conserved among members of the RISKMARKER proteins) may not be essential for activity and thus are likely to be amenable to alteration.

Another aspect of the invention pertains to nucleic acid molecules encoding RISKMARKER proteins that contain changes in amino acid residues that are not essential for activity. Such RISKMARKER proteins differ in amino acid sequence from the amino acid sequences of polypeptides encoded by nucleic acids containing RISKMARKER 1, or RISKMARKER 6–8, yet retain biological activity. In one embodiment, the isolated nucleic acid molecule comprises a nucleotide sequence encoding a protein, wherein the protein comprises an amino acid sequence at least about 45% homologous, more preferably 60%, and still more preferably at least about 70%, 80%, 90%, 95%, 98%, and most preferably at least about 99% homologous to the amino acid sequence of the amino acid sequences of polypeptides encoded by nucleic acids comprising RISKMARKER 1, or RISKMARKER 6–8.

An isolated nucleic acid molecule encoding a RISKMARKER protein homologous to can be created by introducing one or more nucleotide substitutions, additions or deletions into the nucleotide sequence of a nucleic acid comprising RISKMARKER 1, or RISKMARKER 6–8, such that one or more amino acid substitutions, additions or deletions are introduced into the encoded protein.

Mutations can be introduced into a nucleic acid comprising RISKMARKER 1, or RISKMARKER 6–8 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in RISKMARKER is replaced with another amino acid residue from the same side chain family. Alternatively, in another embodiment, mutations can be introduced randomly along all or part of a RISKMARKER coding sequence, such as by saturation mutagenesis, and the resultant mutants can be screened for RISKMARKER biological activity to identify mutants that retain activity. Following mutagenesis of the nucleic acid, the encoded protein can be expressed by any recombinant technology known in the art and the activity of the protein can be determined.

In one embodiment, a mutant RISKMARKER protein can be assayed for (1) the ability to form protein:protein interactions with other RISKMARKER proteins, other cell-surface proteins, or biologically active portions thereof, (2) complex formation between a mutant RISKMARKER protein and a RISKMARKER ligand; (3) the ability of a mutant RISKMARKER protein to bind to an intracellular target protein or biologically active portion thereof; (e.g., avidin proteins); (4) the ability to bind ATP; or (5) the ability to specifically bind a RISKMARKER protein antibody.

In other embodiment, the fragment of the complementary polynucleotide sequence described in claim 1 wherein the fragment of the complementary polynucleotide sequence hybridizes to the first sequence.

In other specific embodiments, the nucleic acid is RNA or DNA. The fragment or the fragment of the complementary polynucleotide sequence described in claim 38, wherein the fragment is between about 10 and about 100 nucleotides in length, e.g., between about 10 and about 90 nucleotides in length, or about 10 and about 75 nucleotides in length, about 10 and about 50 bases in length, about 10 and about 40 bases in length, or about 15 and about 30 bases in length.

Anti-sense

Another aspect of the invention pertains to isolated antisense nucleic acid molecules that are hybridizable to or complementary to the nucleic acid molecule comprising the nucleotide sequence of a RISKMARKER or INJURYMARKER sequence or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire RISKMARKER or INJURYMARKER coding strand, or to only a portion thereof. Nucleic acid molecules encoding fragments, homologs, derivatives and analogs of a RISKMARKER or INJURYMARKER protein, or antisense nucleic acids complementary to a nucleic acid comprising a RISKMARKER or INJURYMARKER nucleic acid sequence are additionally provided.

In one embodiment, an antisense nucleic acid molecule is antisense to a "coding region" of the coding strand of a nucleotide sequence encoding RISKMARKER or INJURYMARKER. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding RISKMARKER. The term "noncoding region" refers to 5' and 3' sequences which flank the coding region that are not translated into amino acids (i.e., also referred to as 5' and 3' untranslated regions).

Given the coding strand sequences encoding RISKMARKER or INJURYMARKER disclosed herein, antisense nucleic acids of the invention can be designed according to the rules of Watson and Crick or Hoogsteen base pairing. The antisense nucleic acid molecule can be complementary to the entire coding region of RISKMARKER or INJURYMARKER mRNA, but more preferably is an oligonucleotide that is antisense to only a portion of the coding or noncoding region of RISKMARKER or INJURYMARKER mRNA. For example, the antisense oligonucleotide can be complementary to the region surrounding the translation start site of RISKMARKER or INJURYMARKER mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a RISKMARKER or INJURYMARKER protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual α-units, the strands run parallel to each other (Gaultier et al. (1987) Nucleic Acids Res 15: 6625–6641). The antisense nucleic acid molecule can also comprise a 2'-o-methylribonucleotide (Inoue et al. (1987) Nucleic Acids Res 15: 6131–6148) or a chimeric RNA-DNA analogue (Inoue et al. (1987) FEBS Lett 215: 327–330).

Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave RISKMARKER or INJURYMARKER mRNA transcripts to thereby inhibit translation of RISKMARKER or INJURYMARKER mRNA. A ribozyme having specificity for a RISKMARKER or INJURYMARKER -encoding nucleic acid can be designed based upon the nucleotide sequence of a RISKMARKER or INJURYMARKER DNA disclosed herein. For example, a derivative of a Tetrahymena L-19 IVS RNA can be constructed in which the nucleotide sequence of the active site is complementary to the nucleotide sequence to be cleaved in a RISKMARKER or INJURYMARKER-encoding mRNA. See, e.g., Cech et al. U.S. Pat. No. 4,987,071; and Cech et al. U.S. Pat. No. 5,116,742. Alternatively, RISKMARKER or INJURYMARKER mRNA can be used to select a catalytic RNA having a specific ribonuclease activity from a pool of RNA molecules. See, e.g., Bartel et al., (1993) Science 261:1411–1418.

Alternatively, RISKMARKER or INJURYMARKER gene expression can be inhibited by targeting nucleotide sequences complementary to the regulatory region of a RISKMARKER or INJURYMARKER nucleic acid (e.g., the RISKMARKER or INJURYMARKER promoter and/or enhancers) to form triple helical structures that prevent transcription of the RISKMARKER or INJURYMARKER gene in target cells. See generally, Helene. (1991) Anticancer Drug Des. 6: 569–84; Helene. et al. (1992) Ann. N.Y. Acad Sci. 660:27–36; and Maher (1992) Bioassays 14: 807–15.

In various embodiments, the nucleic acids of RISKMARKER or INJURYMARKER can be modified at the base moiety, sugar moiety or phosphate backbone to improve, e g., the stability, hybridization, or solubility of the molecule. For example, the deoxyribose phosphate backbone of the nucleic acids can be modified to generate peptide nucleic acids (see Hyrup et al. (1996) Bioorg Med Chem 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) PNAS 93: 14670–675.

PNAs of RISKMARKER or INJURYMARKER can be used in therapeutic and diagnostic applications. For example, PNAs can be used as antisense or antigene agents for sequence-specific modulation of gene expression by, e.g., inducing transcription or translation arrest or inhibiting replication. PNAs of RISKMARKER or INJURYMARKER can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al (1996), above; Perry-O'Keefe (1996), above).

In another embodiment, PNAs of RISKMARKER or INJURYMARKER can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of RISKMARKER or INJURYMARKER can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A*. 86:6553–6556; Lemaitre et al., 1987, Proc. Natl. Acad. Sci. 84:648–652; PCT Publication No. W088/09810) or the blood-brain barrier (see, e.g., PCT Publication No. W089/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res*. 5: 539–549). To this end, the oligonucleotide may be conjugated to another molecule, e.g., a peptide, a hybridization triggered cross-linking agent, a transport agent, a hybridization-triggered cleavage agent, etc.

Riskmarker and Injurymarker Polypeptides

One aspect of the invention pertains to isolated RISKMARKER or INJURYMARKER proteins, and biologically active portions thereof, or derivatives, fragments, analogs or homologs thereof. Also provided are polypeptide fragments suitable for use as immunogens to raise anti-RISKMARKER or INJURYMARKER antibodies, e.g. antibodies against RISKMARKER 1, or RISKMARKER 6–8. In one embodiment, native RISKMARKER or INJURYMARKER proteins can be isolated from cells or tissue sources by an appropriate purification scheme using standard protein purification techniques. In another embodiment, RISKMARKER or INJURYMARKER proteins are produced by recombinant DNA techniques. Alternative to recombinant expression, a RISKMARKER or INJURYMARKER protein or polypeptide can be synthesized chemically using standard peptide synthesis techniques.

An "isolated" or "purified" protein or biologically active portion thereof is substantially free of cellular material or other contaminating proteins from the cell or tissue source from which the RISKMARKER or INJURYMARKER protein is derived, or substantially free from chemical precursors or other chemicals when chemically synthesized. The language "substantially free of cellular material" includes preparations of RISKMARKER or INJURYMARKER protein in which the protein is separated from cellular components of the cells from which it is isolated or recombinantly produced. In one embodiment, the language "substantially free of cellular material" includes preparations of RISKMARKER or INJURYMARKER protein having less than about 30% (by dry weight) of non-RISKMARKER or INJURYMARKER protein (also referred to herein as a "contaminating protein"), more preferably less than about 20% of non-RISKMARKER or INJURYMARKER protein, still more preferably less than about 10% of non-RISKMARKER or INJURYMARKER protein, and most preferably less than about 5% non-RISKMARKER or INJURYMARKER protein. When the RISKMARKER or INJURYMARKER protein or biologically active portion thereof is recombinantly produced, it is also preferably substantially free of culture medium, ie., culture medium represents less than about 20%, more preferably less than about 10%, and most preferably less than about 5% of the volume of the protein preparation.

The language "substantially free of chemical precursors or other chemicals" includes preparations of RISKMARKER or INJURYMARKER protein in which the protein is separated from chemical precursors or other chemicals that are involved in the synthesis of the protein. In one embodiment, the language "substantially free of chemical precursors or other chemicals" includes preparations of RISKMARKER or INJURYMARKER protein having less than about 30% (by dry weight) of chemical precursors or non-RISKMARKER or INJURYMARKER chemicals, more preferably less than about 20% chemical precursors or non-RISKMARKER or INJURYMARKER chemicals, still more preferably less than about 10% chemical precursors or non-RISKMARKER or INJURYMARKER chemicals, and most preferably less than about 5% chemical precursors or non-RISKMARKER or INJURYMARKER chemicals.

Biologically active portions of a RISKMARKER or INJURYMARKER protein include peptides comprising amino acid sequences sufficiently homologous to or derived from the amino acid sequence of the RISKMARKER or INJURYMARKER protein, e.g., the amino acid sequence encoded by a nucleic acid comprising RISKMARKER or INJURYMARKER 1–20 that include fewer amino acids than the full length RISKMARKER or INJURYMARKER proteins, and exhibit at least one activity of a RISKMARKER or INJURYMARKER protein. Typically, biologically active portions comprise a domain or motif with at least one activity of the RISKMARKER or INJURYMARKER protein. A biologically active portion of a RISKMARKER or INJURYMARKER protein can be a polypeptide which is, for example, 10, 25, 50, 100 or more amino acids in length.

A biologically active portion of a RISKMARKER or INJURYMARKER protein of the present invention may contain at least one of the above-identified domains conserved between the RISKMARKER or INJURYMARKER proteins. An alternative biologically active portion of a RISKMARKER or INJURYMARKER protein may contain at least two of the above-identified domains. Another biologically active portion of a RISKMARKER or INJURYMARKER protein may contain at least three of the above-identified domains. Yet another biologically active portion of a RISKMARKER or INJURYMARKER protein of the present invention may contain at least four of the above-identified domains.

Moreover, other biologically active portions, in which other regions of the protein are deleted, can be prepared by recombinant techniques and evaluated for one or more of the functional activities of a native RISKMARKER or INJURYMARKER protein.

In some embodiments, the RISKMARKER or INJURYMARKER protein is substantially homologous to one of these RISKMARKER or INJURYMARKER proteins and retains its the functional activity, yet differs in amino acid sequence due to natural allelic variation or mutagenesis, as described in detail below.

In specific embodiments, the invention includes an isolated polypeptide comprising an amino acid sequence that is 80% or more identical to the sequence of a polypeptide whose expression is modulated in a mammal to which hepatotoxic agent is administered.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of a DNA sequence comprising RISKMARKER 1, or RISKMARKER 6–8.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides RISKMARKER chimeric or fusion proteins. As used herein, an RISKMARKER "chimeric protein" or "fusion protein" comprises an RISKMARKER polypeptide operatively linked to a non-RISKMARKER polypeptide. A "RISKMARKER polypeptide" refers to a polypeptide having an amino acid sequence corresponding to RISKMARKER, whereas a "non-RISKMARKER polypeptide" refers to a polypeptide having an amino acid sequence corresponding to a protein that is not substantially homologous to the RISKMARKER protein, e.g., a protein that is different from the RISKMARKER protein and that is derived from the same or a different organism. Within an RISKMARKER fusion protein the RISKMARKER polypeptide can correspond to all or a portion of an RISKMARKER protein. In one embodiment, an RISKMARKER fusion protein comprises at least one biologically active portion of an RISKMARKER protein. In another embodiment, an RISKMARKER fusion protein comprises at least two biologically active portions of an RISKMARKER protein. In yet another embodiment, an RISKMARKER fusion protein comprises at least three biologically active portions of an RISKMARKER protein. Within the fusion protein, the term "operatively linked" is intended to indicate that the RISKMARKER polypeptide and the non-RISKMARKER polypeptide are fused in-frame to each other. The non-RISKMARKER polypeptide can be fused to the N-terminus or C-terminus of the RISKMARKER polypeptide.

For example, in one embodiment an RISKMARKER fusion protein comprises an RISKMARKER domain operably linked to the extracellular domain of a second protein. Such fusion proteins can be further utilized in screening assays for compounds which modulate RISKMARKER activity (such assays are described in detail below).

In yet another embodiment, the fusion protein is a GST-RISKMARKER fusion protein in which the RISKMARKER sequences are fused to the C-terminus of the GST (i.e., glutathione S-transferase) sequences. Such fusion proteins can facilitate the purification of recombinant RISKMARKER, e.g. RISKMARKER 1, or RISKMARKER 6–8.

In another embodiment, the fusion protein is an RISKMARKER protein containing a heterologous signal sequence at its N-terminus. For example, a native RISKMARKER signal sequence can be removed and replaced with a signal sequence from another protein. In certain host cells (e.g., mammalian host cells), expression and/or secretion of RISKMARKER can be increased through use of a heterologous signal sequence.

In yet another embodiment, the fusion protein is a RISKMARKER-immunoglobulin fusion protein in which the RISKMARKER sequences comprising one or more domains are fused to sequences derived from a member of the immunoglobulin protein family. The RISKMARKER-immunoglobulin fusion proteins of the invention can be incorporated into pharmaceutical compositions and administered to a subject to inhibit an interaction between a RISKMARKER ligand and a RISKMARKER protein on the surface of a cell, to thereby suppress RISKMARKER-mediated signal transduction in vivo. The RISKMARKER-immunoglobulin fusion proteins can be used to affect the bioavailability of an RISKMARKER cognate ligand. Inhibition of the RISKMARKER ligand/RISKMARKER interaction may be useful therapeutically for both the treatments of proliferative and differentiative disorders, as well as modulating (e.g. promoting or inhibiting) cell survival. Moreover, the RISKMARKER-immunoglobulin fusion proteins of the invention can be used as immunogens to produce anti-RISKMARKER antibodies in a subject, to purify RISKMARKER ligands, and in screening assays to identify molecules that inhibit the interaction of RISKMARKER with a RISKMARKER ligand.

An RISKMARKER chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) Current Protocols in Molecular Biology, John Wiley & Sons, 1992). Moreover, many expression vectors are commercially available that already encode a fusion moiety (e.g., a GST polypeptide). A RISKMARKER -encoding nucleic acid can be cloned into such an expression vector such that the fusion moiety is linked in-frame to the RISKMARKER protein.

Riskmarker and Injurymarker Agonists and Antagonists

The present invention also pertains to variants of the RISKMARKER or INJURYMARKER proteins that function as either RISKMARKER or INJURYMARKER agonists (mimetics) or as RISKMARKER or INJURYMARKER antagonists. Variants of the RISKMARKER or INJURYMARKER protein can be generated by mutagenesis, e.g., discrete point mutation or truncation of the RISKMARKER or INJURYMARKER protein. An agonist of the RISKMARKER or INJURYMARKER protein can retain substantially the same, or a subset of, the biological activities of the naturally occurring form of the RISKMARKER or INJURYMARKER protein. An antagonist of the RISKMARKER or INJURYMARKER protein can inhibit one or more of the activities of the naturally occurring form of the RISKMARKER or INJURYMARKER protein by, for example, competitively binding to a downstream or upstream member of a cellular signaling cascade which includes the RISKMARKER or INJURYMARKER protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the RISKMARKER or INJURYMARKER proteins.

Variants of the RISKMARKER or INJURYMARKER protein that function as either RISKMARKER or INJURYMARKER agonists (mimetics) or as RISKMARKER or INJURYMARKER antagonists can be identified by screening combinatorial libraries of mutants, e.g., truncation mutants, of the RISKMARKER or INJURYMARKER protein for RISKMARKER or INJURYMARKER protein agonist or antagonist activity. In one embodiment, a variegated library of RISKMARKER or INJURYMARKER variants is generated by combinatorial mutagenesis at the nucleic acid level and is encoded by a variegated gene library. A variegated library of RISKMARKER or INJURYMARKER variants can be produced by, for example, enzymatically ligating a mixture of synthetic oligonucleotides into gene sequences such that a degenerate set of potential RISKMARKER or INJURYMARKER sequences is expressible as individual polypeptides, or alternatively, as a set of larger fusion proteins (e.g., for phage display) containing the set of RISKMARKER or INJURYMARKER sequences therein. There are a variety of methods which can be used to produce libraries of potential RISKMARKER or INJURYMARKER variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential RISKMARKER or INJURYMARKER sequences. Methods for synthesizing degenerate oligonucleotides are known in the art (see, e.g., Narang (1983) Tetrahedron 39:3; Itakura et al. (1984) *Annu Rev Biochem* 53:323; Itakura et al. (1984) Science 198:1056; Ike et al. (1983) *Nucl Acid Res* 11:477.

Polypeptide Libraries

In addition, libraries of fragments of the RISKMARKER or INJURYMARKER protein coding sequence can be used to generate a variegated population of RISKMARKER or INJURYMARKER fragments for screening and subsequent selection of variants of an RISKMARKER or INJURYMARKER protein. In one embodiment, a library of coding sequence fragments can be generated by treating a double stranded PCR fragment of a RISKMARKER or INJURYMARKER coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the RISKMARKER or INJURYMARKER protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of RISKMARKER or INJURYMARKER proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify RISKMARKER or INJURYMARKER variants (Arkin and Yourvan (1992) PNAS 89:7811–7815; Delgrave et al. (1993) Protein Engineering 6:327–331).

Anti-Riskmarker and Anti-Injurymarker Antibodies

An isolated RISKMARKER or INJURYMARKER protein, or a portion or fragment thereof, can be used as an immunogen to generate antibodies that bind RISKMARKER or INJURYMARKER using standard techniques for polyclonal and monoclonal antibody preparation. The full-length RISKMARKER or INJURYMARKER protein can be used or, alternatively, the invention provides antigenic peptide fragments of RISKMARKER or INJURYMARKER for use as immunogens. The antigenic peptide of RISKMARKER or INJURYMARKER comprises at least 8 amino acid residues of the amino acid sequence encoded by a nucleic acid comprising the nucleic acid sequence shown in RISKMARKER 1–8 and INJURYMARKER 1–10 and encompasses an epitope of RISKMARKER or INJURYMARKER such that an antibody raised against the peptide forms a specific immune complex with RISKMARKER or INJURYMARKER. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of RISKMARKER or INJURYMARKER that are located on the surface of the protein, e.g., hydrophilic regions. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824–3828; Kyte and Doolittle 1982, J. Mol. Biol. 157: 105–142, each incorporated herein by reference in their entirety.

RISKMARKER or INJURYMARKER polypeptides or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen. Such antibodies include, but are not limited to, polyclonal, monoclonal, chimeric, single chain, $F_{ab}$ and $F_{(ab')2}$ fragments, and an $F_{ab}$ expression library. Various procedures known within the art may be used for the production of polyclonal or monoclonal antibodies to an RISKMARKER or INJURYMARKER protein sequence, e.g. RISKMARKER 1 or RISKMARKER 6–8, or derivatives, fragments, analogs or homologs thereof. Some of these proteins are discussed below.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed RISKMARKER or INJURYMARKER protein or a chemically synthesized RISKMARKER or INJURYMARKER polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as *Bacille Calmette-Guerin* and *Corynebacterium parvum*, or similar immunostimulatory agents. If desired, the antibody molecules directed against RISKMARKER or INJURYMARKER can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of RISKMARKER or INJURYMARKER. A monoclonal antibody composition thus typically displays a single binding affinity for a particular RISKMARKER or INJURYMARKER protein with which it immunoreacts. For preparation of monoclonal antibodies directed towards a particular RISKMARKER or INJURYMARKER protein, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 Nature 256: 495–497); the trioma technique; the human B-cell hybridoma technique (see Kozbor, et al., 1983 Immunol Today 4: 72) and the EBV hybridoma technique to produce human monoclonal antibodies (see Cole, et al., 1985 In: Monoclonal Antibodies and Cancer Therapy, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al, 1985 In: Monoclonal Antibodies and Cancer Therapy, Alan R. Liss, Inc., pp. 77–96).

According to the invention, techniques can be adapted for the production of single-chain antibodies specific to a RISKMARKER or INJURYMARKER protein (see e.g., U.S. Pat. No. 4,946,778). In addition, methods can be adapted for the construction of $F_{ab}$ expression libraries (see e.g., Huse, et al, 1989 Science 246: 1275–1281) to allow rapid and effective identification of monoclonal $F_{ab}$ fragments with the desired specificity for a RISKMARKER or INJURYMARKER protein or derivatives, fragments, analogs or homologs thereof. Non-human antibodies can be "humanized" by techniques well known in the art. See e.g., U.S. Pat. No. 5,225,539. Antibody fragments that contain the idiotypes to a RISKMARKER or INJURYMARKER protein may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-RISKMARKER or INJURYMARKER antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al.(1988) Science 240:1041–1043; Liu et al. (1987) PNAS 84:3439–3443; Liu et al. (1987) J Immunol. 139:3521–3526; Sun et al. (1987) PNAS 84:214–218; Nishimura et al. (1987) Cancer Res 47:999–1005; Wood et al. (1985) Nature 314:446449; Shaw et al. (1988) J Natl Cancer Inst. 80:1553–1559); Morrison(1985) Science 229:1202–1207; Oi et al. (1986) BioTechniques 4:214; U.S. Pat. No. 5,225,539; Jones et al. (1986) Nature 321:552–525; Verhoeyan et al. (1988) Science 239:1534; and Beidler et al. (1988) J Immunol 141:4053–4060.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a RISKMARKER or INJURYMARKER protein is facilitated by generation of hybridomas that bind to the fragment of a RISKMARKER or INJURYMARKER protein possessing such a domain. Antibodies that are specific for one or more domains within a RISKMARKER or INJURYMARKER protein, e.g., domains spanning the above-identified conserved regions of RISKMARKER or INJURYMARKER family proteins, or derivatives, fragments, analogs or homologs thereof, are also provided herein.

Anti-RISKMARKER or anti-INJURYMARKER antibodies may be used in methods known within the art relating to the localization and/or quantitation of a RISKMARKER or INJURYMARKER protein (e.g., for use in measuring levels of the RISKMARKER or INJURYMARKER protein within appropriate physiological samples, for use in diagnostic methods, for use in imaging the protein, and the like). In a given embodiment, antibodies for RISKMARKER or INJURYMARKER proteins, or derivatives, fragments, analogs or homologs thereof, that contain the antibody derived binding domain, are utilized as pharmacologically-active compounds [hereinafter "Therapeutics"].

An anti-RISKMARKER or INJURYMARKER antibody (e.g., monoclonal antibody) can be used to isolate RISKMARKER or INJURYMARKER by standard techniques, such as affinity chromatography or immunoprecipitation. An anti-RISKMARKER or INJURYMARKER antibody can facilitate the purification of natural RISKMARKER or INJURYMARKER from cells and of recombinantly produced RISKMARKER or INJURYMARKER expressed in host cells. Moreover, an anti-RISKMARKER or INJURYMARKER antibody can be used to detect RISKMARKER or INJURYMARKER protein (e.g., in a cellular lysate or cell supernatant) in order to evaluate the abundance and pattern of expression of the RISKMARKER or INJURYMARKER protein. Anti-RISKMARKER or INJURYMARKER antibodies can be used diagnostically to monitor protein levels in tissue as part of a clinical testing procedure, e.g., to, for example, determine the efficacy of a given treatment regimen. Detection can be facilitated by coupling (ie., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Riskmarker Recombinant Vectors and Host Cells

Another aspect of the invention pertains to vectors, preferably expression vectors, containing a nucleic acid encoding RISKMARKER protein, e.g. RISKMARKER 1, or RISKMARKER 6–8, or derivatives, fragments, analogs or homologs thereof. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., RISKMARKER proteins, mutant forms, fusion proteins, etc.).

The recombinant expression vectors of the invention can be designed for expression of RISKMARKER in prokaryotic or eukaryotic cells. For example, RISKMARKER can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion E. coli expression vectors include pTrc (Amrann et al., (1988) Gene 69:301–315) and pET 11d (Studier et al., Gene Expression Technology: Methods in Enzymology 185, Academic Press, San Diego, Calif. (1990) 60–89).

One strategy to maximize recombinant protein expression in E. coli is to express the protein in a host bacteria with an impaired capacity to proteolytically cleave the recombinant protein. See, Gottesman, Gene Expression Technology: Methods in Enzymology 185, Academic Press, San Diego, Calif. (1990) 119–128. Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111–2118). Such alteration of nucleic acid sequences of the invention can be carried out by standard DNA synthesis techniques.

In another embodiment, the RISKMARKER expression vector is a yeast expression vector. Examples of vectors for expression in yeast S. cerevisiae include pYepSec 1 (Baldari, et al., (1987) EMBO J 6:229–234), pMFa (Kurjan and Herskowitz, (1982) Cell 30:933–943), pJRY88 (Schultz et al, (1987) Gene 54:113–123), pYES2 (Invitrogen Corporation, San Diego, Calif.), and picZ (InVitrogen Corp, San Diego, Calif).

Alternatively, RISKMARKER can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufmnan et al. (1987) EMBO J 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev 1:268–277), lymphoid-specific promoters (Calame and Eaton (1988) Adv Immunol 43:235–275), in particular promoters of T cell receptors (Winoto and Baltimore (1989) EMBO J 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) PNAS 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264;, 66). Developmentally-regulated promoters are also encompassed, e.g., the murine hox promoters (Kessel and Gruss (1990) Science 249:374–379) and the □-fetoprotein promoter (Campes and Tilghman (1989) Genes Dev 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to RISKMARKER mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al, "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, RISKMARKER protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding RISK-MARKER or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an RISKMARKER protein, e.g. RISKMARKER 1, or RISKMARKER 6–8. Accordingly, the invention further provides methods for producing RISKMARKER protein using the host cells of the invention. In one embodiment, the method comprises culturing the host cell of invention (into which a recombinant expression vector encoding RISK-MARKER has been introduced) in a suitable medium such that RISKMARKER protein is produced. In another embodiment, the method further comprises isolating RISK-MARKER from the medium or the host cell.

Pharmaceutical Compositions

The RISKMARKER nucleic acid molecules, RISK-MARKER proteins, and anti-RISKMARKER or anti-INJURYMARKER antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a RISKMARKER protein or anti-RISKMARKER or INJURYMARKER antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Kits and Nucelic Acid Collections for Identifying Riskmarker and Injurymarker Nucleic Acids In another aspect, the invention provides a kit useful for examining hepatotoxicity of agents. The kit can include nucleic acids that detect two or more RISKMARKER or INJURYMARKER sequences. In preferred embodiments, the kit includes reagents which detect 3, 4, 5, 6, 8, 10, 12, 15, or all of the RISKMARKER or INJURYMARKER nucleic acid sequences.

The invention also includes an isolated plurality of sequences which can identify one or more RISKMARKER or INJURYMARKER responsive nucleic acid sequences. The kit or plurality may include, e.g., sequence homologous to RISKMARKER or INJURYMARKER nucleic acid sequences, or sequences which can specifically identify one or more RISKMARKER or INJURYMARKER nucleic acid sequences.

Other Embodiments

It is to be understood that while the invention has been described in conjunction with the detailed description thereof, the foregoing description is intended to illustrate and not limit the scope to the invention, which is defined by the scope of the appended claims. Other aspects, advantages, and modifications are within the scope of the following claims.

We claim:

1. An isolated nucleic acid consisting of the nucleic acid sequence of SEQ ID NO: 1, or its complement.
2. An isolated nucleic acid consisting of the nucleic acid sequence of SEQ ID NO: 2, or its complement.
3. An isolated nucleic acid consisting of the nucleic acid sequence of SEQ ID NO: 15, or its complement.
4. An isolated nucleic acid consisting of the nucleic acid sequence of SEQ ID NO: 17, or its complement.
5. A composition comprising the nucleic acid of claim 1.
6. A vector comprising the nucleic acid of claim 2.
7. A cell comprising the vector of claim 6.
8. A composition comprising the nucleic acid of claim 2.
9. A vector comprising the nucleic acid of claim 3.
10. A cell comprising the vector of claim 9.
11. A composition comprising the nucleic acid of claim 3.
12. A vector comprising the nucleic acid of claim 4.
13. A cell comprising the vector of claim 12.
14. A composition comprising the nucleic acid of claim 4.

* * * * *

SEQUENCE LISTING

<160> NUMBER OF SEQ ID NOS: 50

<210> SEQ ID NO 1
<211> LENGTH: 123
<212> TYPE: DNA
<213> ORGANISM: Rattus norvegicus

<400> SEQUENCE: 1

```
caattgaaaa aagtttgttc tagtggtcga aaggcccaac actgtgttct tgccagtgag      60
ttaggttgta cagaacggcg ttagcactag cgcttgacag aacctcacag acccaaaggt    120
acc                                                                  123

<210> SEQ ID NO 2
<211> LENGTH: 1266
<212> TYPE: DNA
<213> ORGANISM: Rattus norvegicus

<400> SEQUENCE: 2
tttttttttt tttttttcaa gttccaaaga catttttttt tttttttta tgattcaagg      60 atttattaag tcatacatgc aaaacatact gctaactgca ttagcaaaag atcaatgtaa    120
aaacactcca caattctgca actgtcaatt gaaaaaagtt tgttctagtg gtcgaaaggc    180
ccaacactgt gttcttgcca gtgagttagg ttgtacagaa cggcgttagc actagcgctt    240
gacagaacct cacagaccca aaggtaccgg aagcatgtgt ccgcgtgggt gaggtctaga    300
gggggcggca tcaatcacat gacagtgttg gtactctggc aagacagtga tgtttcagaa    360
tatctaaaat agtttaaaaa ctgtaaagcc gcagcacgtg atttctacac ccagttacta    420
gaaaacgaag ggaagcacta gtcagctgag taaggaagg tgaaaacagg aacgcacttc     480
tactatctac caaaaaaatc tccgaatgca ttatcgaaaa gatcttatag tacaggtcag    540
acatattgct cgttaagaag ggggtcctaa agaaaagcac ttgctaagtt agcaactgtg    600
aggatggcca gttaaatat ggactcaacg ccccatctgg ggagggacag caggggaag     660 gggggctcaa gagagacact gataagatcg gccatttgtc atctactgtt tgacagaaat    720
taaccgttaa aaagctttac ccgtgacact tttattcagt tgaattactc catgtacaat    780
gtagtgtaaa ttaatctcta cttcatatta gtcaaaatac tgtctgtctc ctttgatgac    840
gtcgtgtttc acacactcca cccagcacac ccacgactag gaacagaata cttcgttaga    900
ggcaacacag gagccagagt tctgttcaaa gcctgcagaa gccggtcagc tggtatttta    960
gagaactcac tatgaaatca aagagcagag ctgttacacc catcgtgacg tacagtacaa   1020
agttacgtaa tgagcatggg ctgataagtt acaggtgcgt tacatggcag cgtgtcatta   1080
aggaggctgt gctgtgtcac acggtctggg agctacggga gggtctgcac ccctgagccc   1140
agaagctgca gtcttcttaa ggacaaagtc tctcaacagc ttagtgctta cgtgttctca   1200
gcacaacgca acttagttca caaggtatt tggcaattct taatctgagc aagaataggg    1260
gattt                                                               1266

<210> SEQ ID NO 3
<211> LENGTH: 484
<212> TYPE: DNA
<213> ORGANISM: Rattus norvegicus
<220> FEATURE:
<221> NAME/KEY: misc_feature
<222> LOCATION: (455)
<223> OTHER INFORMATION: Wherein n is g or a or t or c

<400> SEQUENCE: 3
tttttttttt ttttttttggc agaattctga tgtttactgg gacccatagt agtcaaggtg     60
acagcaaggg tagggagga aactcagcag aggcggatcc caggtctgga gggaagctga    120
cagcagccca gtaagctgtg ccagaaggct gtaacagtag cggagccagt gacagcgcca    180
ggctgggctg ggttctctct gtgggtgtgc acggcaaagc tgcggcctgt gggccctggg    240
gggcctgtca gctccacatc caccacatgc atgtcggtga ggctaaggtc agccacaagc    300
```

-continued

```
acccccaatga cacgatcaaa gcctagactg ggagcggcca gggcagcggc tgccatggtg      360
ttggagtttc ggggggccaa ggggcagagc ccacgcacag ggccctcata gagcactgtg      420
cggggcccac tactatgtgc ggcagccagg ggtcnctcca gccggaagcc atcaggatgt      480
gtgg                                                                  484
```

<210> SEQ ID NO 4
<211> LENGTH: 650
<212> TYPE: DNA
<213> ORGANISM: Rattus norvegicus

<400> SEQUENCE: 4

```
tttttttttt ttttttggc agaattctga tgtttactgg gacccatagt agtcaaggtg       60
acagcaaggg taggggagga aactcagcag aggcggatcc caggtctgga gggaagctga      120
cagcagccca gtaagctgtg ccagaaggct gtaacagtag cggagccagt gacagcgcca      180
ggctgggctg ggttctctct gtgggtgtgc acggcaaagc tgcggcctgt gggccctggg      240
gggcctgtca gctccacatc caccacatgc atgtcggtga ggctaaggtc agccacaagc      300
accccaatga cacgatcaaa gcctagactg ggagcggcca gggcagcggc tgccatggtg      360
ttggagtttc ggggggccaa ggggcagagc ccacgcacag ggccctcata gagcactgtg      420
cggggcccac tactatgtgc ggcagccagg ggtccctcca gccggaagcc atcaggatgt      480
gtggccatgg tgactcgaag gctctggagg cctccggctg catccaatct gctgatgtct      540
tcacaacccc acagggcccc tcgggccaca aacaccgtgt ggcccagtg gtttgaagcc       600 tccaggagct gccgctctgt ggtctggtca gcgagagctg aggggggatcc                650
```

<210> SEQ ID NO 5
<211> LENGTH: 256
<212> TYPE: DNA
<213> ORGANISM: Rattus norvegicus

<400> SEQUENCE: 5

```
ccatggatga aatcttccag catctgaatg cctaccgcca ggaggctcac aactgcatct       60
ccagccacat tccattgatc atccagtatt tcatcttgaa gatgtttgct gagaagctgc      120
agaagggcat gctccagctc ctgcaggaca aggattcctg cagctggctc ctgaaggaaa      180
agagtgacac cagtgagaag aggagattcc tgaaggagcg gttggcaagg ctggcccaag      240
ctcagcgcag gctagc                                                     256
```

<210> SEQ ID NO 6
<211> LENGTH: 369
<212> TYPE: DNA
<213> ORGANISM: Rattus norvegicus

<400> SEQUENCE: 6

```
tctagaaagt caccttggaa gaagtgtacg cagggaactt tgtggaagta gttagaaaca       60
agcccgtagc caggcaggct cctggcaaac ggaaatgcaa ctgtcggcag agatgcgaa      120 ccacacagct gggaccaggg cgcttccaaa tgacccagga agtggtttgt gacgagtgcc      180
ctaatgtcaa actagtgaat gaagaacgaa cactagaagt ggaaatagag cctggggtga      240
gagatggcat ggagtacccc tttattggag aaggtgagcc tcatgtggat ggggaacccg      300
gagacttacg gttccgaatc aaagttgtca agcaccggat atttgagagg agaggggatg      360
acctgtaca                                                             369
```

<210> SEQ ID NO 7
<211> LENGTH: 167
<212> TYPE: DNA
<213> ORGANISM: Rattus norvegicus

<400> SEQUENCE: 7

```
gggcccccact aaaacataca caaaagaata aaaatgttca ttttaaactt aaactgcttc    60
ctggttttac aaggcataaa tatatagcat ctccaacagc tacctgtaga ttctgttagt   120
gcaaaaccct agaaaccctc ctggagctca aaggcatccg gactagt               167
```

<210> SEQ ID NO 8
<211> LENGTH: 594
<212> TYPE: DNA
<213> ORGANISM: Rattus norvegicus

<400> SEQUENCE: 8

```
tttttttttt ttttttaaa aaagattata aaattgaatt tattgagttt cacacaagat    60
gcacttataa aattagtact gaatgccatt atgacagaag tgagcatcat ccacactccc   120
aagagcatct gcaaaggaaa tcaatcttca gagaatagca cagaaacaga aaatccaagc   180
gaacaaaaag atacatctag gccgtgttct tgttctgacc agggccgcat ttggcaaagc   240
tttctctgca cctccctgg ttgccaagga tactttcttt tgttaaaaaa aaagtttag    300
aagtggggcc ccactaaaac atacacaaaa gaataaaaat gttcatttta aacttaaact   360
gcttcctggt tttacaaggc ataaatatat agcatctcca acagctacct gtagattctg   420
ttagtgcaaa accttagaaa ccctcctgga gctcaaaggc atccggacta gttttgtact   480
taaacaggat acgggtaaac cacttaaaat ttgccatctc tgcccaaagt gtttgcatga   540
gaactgagtt tcagaagaca gcataggaaa gagtcagaaa cggtcaactt tttt         594
```

<210> SEQ ID NO 9
<211> LENGTH: 340
<212> TYPE: DNA
<213> ORGANISM: Rattus norvegicus

<400> SEQUENCE: 9

```
cctaggactg cacaacgtga gtccttgaac caggctctgg aaaaggtgcc cagaccaccc    60
aatggggaca cacagtgagg ccagccccca gtgaaattcc tgctgctacc tggggcccctt  120
ggtgagactc tggcttccgg ctggtagaag ccaaggttgg acgcatagtt gcaaagctcc   180
tccttcaggc acaaagtgtc tatgcttcta atagaacagc agctcccgtg tcctggctga   240
ccggagcaca caggctgagc gtgccacagc gacgacggag gccaagcgtg gtgctggtgg   300
tgttactttc ccgtgagttc cagcaccttc ttcaccatgg                         340
```

<210> SEQ ID NO 10
<211> LENGTH: 797
<212> TYPE: DNA
<213> ORGANISM: Rattus Norvegicus

<400> SEQUENCE: 10

```
tttttttttt tttttttttt ttgagttttcc actgtggaaa agagtttatt gtatggctgc    60
agggatctac tacagaatcc ccctggctgc agttagctgt gcttactctg gacatatctc   120
cgaagacttg gagcctaaat ggttttcttc tttttagagct ttagtacccg atccatcaga   180
cctaggactg cacaacgtga gtccttgaac caggctctgg aaaaggtgcc cagaccaccc   240
aatggggaca cacagtgagg ccagccccca gtgaaattcc tgctgctacc tggggcccctt  300
```

| | |
|---|---|
| ggtgagactc tggcttccgg ctggtagaag ccaaggttgg acgcatagtt gcaaagctcc | 360 |
| tccttcaggc acaaagtgtc tatgcttcta atagaacagc agctcccgtg tcctggctga | 420 |
| ccggagcaca caggctgagc gtgccacagc gacgacggag gccaagcgtg gtgctggtgg | 480 |
| tgttactttc ccgtgagttc cagcaccttc ttcaccatgg ccccaatccc gtcgtggatg | 540 |
| tggtggagtt cggtctcaca catgaaggcc ggggtggtga ccaccttgtt tttctggtcg | 600 |
| acgtgagctt cggtcacacc cttcacacag tgcttggcac ccagggcttt gacggcttcc | 660 |
| gcggttccag catatggcca cttgccccccc tcctcttgct catggcccac ggtgacctcc | 720 |
| acacctttga tcactttggc tgcgaggaca ggagcgatgc agcataggcc aatgggcttc | 780 |
| ttggctccgt ggaattc | 797 |

<210> SEQ ID NO 11
<211> LENGTH: 782
<212> TYPE: DNA
<213> ORGANISM: Rattus norvegicus
<220> FEATURE:
<221> NAME/KEY: misc_feature
<222> LOCATION: (545)
<223> OTHER INFORMATION: Wherein n is g or a or t or c

<400> SEQUENCE: 11

| | |
|---|---|
| ctgatttcaa atttttatta gagaacactt tcggatttca aatttttatt acagaacaaa | 60 |
| cattttctga tttcaaattt ctattataat tctccagtaa tcaaagcagt ggcgttggca | 120 |
| tgaaggcaga cagaggtcat ggaagagacc aggctcagaa acagccccac catgcacagc | 180 |
| gggatgtttt cccaccaagg gcaacatgca aagccaggta tccacatggg tagagtagaa | 240 |
| agtcagacct tacatctcac acacaaatga actcaaaata taccagagag caaagctaag | 300 |
| agctaaaatc aagtttccta gggcaagctg tagtaggctc ccttgggtgg gttaatgctt | 360 |
| ttgtggatgt gactaccaaa aattcaacca gagccaacga cccaactatt aatgggcagt | 420 |
| ggacctaaag agatttcttc aaacgatata taagaaggc caccaagcat ataaaacatg | 480 |
| tgacatcagt agtcagagag atgggaagca gaagcactag cagatcttaa cacctactag | 540 |
| aacanccact aaaaaagagt aagactcaca aggacatggg cacttctaat ctctgtgcac | 600 |
| tgctgccagg acatacaata gtgtggtcac tatggagact acggcagtgc ctactaataa | 660 |
| cagcagagtt accctaagac atacaatctg ctgcgtgtat gctaagcagg atccgaggga | 720 |
| tatttgtata tacatgttca cagcatagtc aggagctcca gggtgggaac aactgaggta | 780 |
| cc | 782 |

<210> SEQ ID NO 12
<211> LENGTH: 1025
<212> TYPE: DNA
<213> ORGANISM: Rattus norvegicus

<400> SEQUENCE: 12

| | |
|---|---|
| ctgatttcaa atttttatta tagaacactt tctgatttca aatttttatt acagaacaaa | 60 |
| cattttctga tttcaaattt ctattataat tctccagtaa tcaaagcagt ggcgttggca | 120 |
| tgaaggcaga cagaggtcat ggaagagacc aggctcagaa acagccccac catgcacagc | 180 |
| gggatgtttt cccaccaagg gcaacatgca aagccaggta tccacatggg tagagtagaa | 240 |
| agtcagacct tacatctcac acacaaatga actcaaaata taccagagag caaagctaag | 300 |
| agctaaaatc aagtttccta gggcaagctg tagtaggctc ccttgggtgg gttaatgctt | 360 |

```
ttgtggatgt gactaccaaa aattcaacca gagccaacga cccaactatt aatgggcagt      420
ggacctaaag agatttcttc aaacgatata taaagaaggc caccaagcat ataaaacatg      480
tgacatcagt agtcagagag atgggaagca gaagcactag cagatcttaa caccctactag     540 aacagccact aaaaagagt aagactcaca aggacatggg cacttctaat ctctgtgcac      600
tgctgccagg acatacaata gtgtggtcac tatggagact acggcagtgc ctactaataa      660
cagcagagtt accctaagac atacaatctg ctgcgtgtat gctaagcagg atccgaggga      720
tatttgtata tacatgttca cagcatagtc aggagctcca gggtgggaac aactgaggta      780
cccacggctg gatgagtagg taacaagaaa catacagcat acatcaaca cacactaaag      840 tctaaagtac tatttgtcct tacaaggaa actcatacat gatacaagcc ttcacggcat      900
tctgctacat gaacacgcac acacacacac acacacacgc actgagaatc      960
tatgtatacc aggcacttag ggtactcaaa ttcagaaaca ggacagagaa tggtgattgc     1020
catgg                                                                  1025

<210> SEQ ID NO 13
<211> LENGTH: 256
<212> TYPE: DNA
<213> ORGANISM: Rattus norvegicus

<400> SEQUENCE: 13
tgtacataat ttattaaaaa tgtctctgac acaaataatg actccactgc atacatagtt       60
ggtgttcaaa aatttcccca atgtttgttc tggacacaat tgttattagc caactcggtg      120
aattcaagac attgttccac acaatgaaca atcgcacaca tgagaactgc acctagaatg     180
tccatcctag aatctccatc catccagtca agtgctgag ctcactgact gaaggaaaca      240
tgacctgtgt tctaga                                                      256

<210> SEQ ID NO 14
<211> LENGTH: 579
<212> TYPE: DNA
<213> ORGANISM: Rattus norvegicus

<400> SEQUENCE: 14
tgtacataat ttattaaaaa tgtctctgac acaaataatg actccactgc atacatagtt       60
ggtgttcaaa aatttcccca atgtttgttc tggacacaat tgttataagc caactcggtg      120
aattcaagac attgttccac acaatgaaca atcgcacaca tgagaactgc acctagaatg     180
tccatcctag aatctccatc catccagtca agtgctgag ctcactgact gaaggaaaca      240
tgacctgtgt tctagaacgt agctggctat gaagtttact catgtgtaaa ttccttaaaa      300
agattaaatt gtttggccca tttctatatt tcataaaata actataatta caaactttct      360
aaaaataatt ttacaaccat gtaattatga ctaaccatat catctaaaaa gtaagtgaag      420
tcattgtcct agagattgtc tgagattatt ctgctgagaa gcttacttca aactcttatc      480
actacttcct acttccagtg tccttgaatt aagaacagaa attgtaacta tgctattcta      540
catcagattg acacaaccta cttctaagta cactattgc                            579

<210> SEQ ID NO 15
<211> LENGTH: 1017
<212> TYPE: DNA
<213> ORGANISM: Rattus norvegicus

<400> SEQUENCE: 15
cccctattct tgctcagatt aagaattgcc aaaataccttt gtgaactaag ttgcgttgtg      60
```

-continued

```
ctgagaacac gtaagcacta agctgttgag agactttgtc cttaagaaga ctgcagcttc      120
tgggctcagg ggtgcagacc ctcccgtagc tcccagaccg tgtgacacag cacagcctcc      180
ttaatgacac gctgccatgt aacgcacctg taacttatca gcccatgctc attacgtaac      240
tttgtactgt acgtcacgat gggtgtaaca gctctgctct ttgatttcat agtgagttct      300
ctaaaatacc agctgaccgg cttctgcagg ctttgaacag aactctggct cctgtgttgc      360
ctctaacgaa gtattctgtt cctagtcgtg ggtgtgctgg gtggagtgtg tgaaacacga      420
cgtcatcaaa ggagacagac agtattttga ctaatatgaa gtagagatta atttacacta      480
cattgtacat ggagtaattc aactgaataa aagtgtcacg ggtaaagctt tttaacggtt      540
aatttctgtc aaacagtaga tgacaaatgg ccgatcttat cagtgtctct cttgagcccc      600
ccttcccct gctgtccctc cccagatggg gcgttgagtc catatttaaa ctggccatcc       660
tcacagttgc taacttagca agtgcttttc tttaggaccc ccttcttaac gagcaatatg      720
tctgacctgt actataagat ctttctgata atgcattcgg agatttttt ggtagatagt       780
agaagtgcgt tcctgttttc accttccttt actcagctga ctagtgcttc ccttcgtttt      840
ctagtaactg ggtgtagaaa tcacgtgctg cggctttaca gtttttaaac tattttagat      900
attctgaaac atcactgtct tgccagagta ccaacactgt catgtgattg atgccgcccc      960
ctctagacct cacccacgcg gacacatgct tccggtacct ttgggtctgt gaggttc        1017
```

<210> SEQ ID NO 16
<211> LENGTH: 1022
<212> TYPE: DNA
<213> ORGANISM: Homo sapiens

<400> SEQUENCE: 16

```
cccccattct tgttcagatt aagagttgcc aaaataccttt ctgaactaca ctgcattgtt     60
gtgccgagaa caccgagcac tgaactttgc aaagaccttc gtctttgaga agacggtagc      120
ttctgcagtt aggaggtgca gacacttgct ctcctatgta gttctcagat gcgtaaagca      180
gaacagcctc ccgaatgaag cgttgccatt gaactcacca gtgagttagc agcacgtgtt      240
cccgacataa cattgtactg taatggagtg agcgtagcag ctcagctctt tggatcagtc      300
tttgtgattt catagcgagt tttctgacca gcttttgcgg agattttgaa cagaactgct      360
atttcctcta atgaagaatt ctgtttagct gtgggtgtgc cgggtggggt gtgtgtgatc      420
aaaggacaaa gacagtattt tgacaaaata cgaagtggag atttacacta cattgtacaa      480
ggaatgaaag tgtcacgggt aaaaactcta aaaggttaat ttctgtcaaa tgcagtagat      540
gatgaaagaa aggttggtat tatcaggaaa tgttttctta agcttttcct ttctcttaca      600
cctgccatgc ctccccaaat tgggcattta attcatcttt aaactggttg ttctgttagt      660
cgctaactta gtaagtgctt ttcttataga accccttctg actgagcaat atgcctcctt      720
gtattataaa atctttctga taatgcatta gaaggttttt ttgtcgatta gtaaaagtgc      780
tttccatgtt actttattca gagctaataa gtgcttttcct tagttttcta gtaactaggt      840
gtaaaaatca tgtgttgcag ctttatagtt tttaaaatat tttagataat tcttaaacta      900
tgaaccttct taacatcact gtcttgccag attaccgaca ctgtcacttg accaatactg      960
accctcttta cctcgcccac gcggacacac gcctcctgta gtcgctttgc ctattgatgt     1020
tc                                                                    1022
```

<210> SEQ ID NO 17

```
<211> LENGTH: 348
<212> TYPE: DNA
<213> ORGANISM: Rattus norvegicus

<400> SEQUENCE: 17
tgaaacatca ctgtcttgcc agagtaccaa cactgtcatg tgattgatgc cgccccctct      60
agacctcacc cacgcggaca catgcttccg gtacctttgg gtctgtgagg ttctgtcaag     120
cgctagtgct aacgccgttc tgtacaacct aactcactgg caagaacaca gtgttgggcc     180
tttcgaccac tagaacaaac ttttttcaat tgacagttgc agaattgtgg agtgttttta     240
cattgatctt ttgctaatgc agttagcagt atgttttgca tgtatgactt aataaatcct     300
tgaatcataa aaaaaaaaa aaaaatgtct ttggaacttg aaaaaaaa                    348

<210> SEQ ID NO 18
<211> LENGTH: 352
<212> TYPE: DNA
<213> ORGANISM: Homo sapiens

<400> SEQUENCE: 18
tgccagatta ccgacactgt cacttgacca atactgaccc tctttacctc gcccacgcgg      60
acaccgcctc ctgtgtcgct ttgcctattg atgttccttt gggtctgtga ggttctgtaa     120
actgtgctag tgctgacgat gttctgtaca acttaactca ctggcgagaa tacagcgtgg     180
gaccccttcag ccactacaac agaattttt aaattgacag ttgcagaatt gtggagtgtt     240
tttacattga tcttttgcta atgcaattag cattatgttt tgcatgtatg acttaataaa     300
tccttgaatc atacgactgg taatactggt gttttgaga cttgatgaac aa              352

<210> SEQ ID NO 19
<211> LENGTH: 484
<212> TYPE: DNA
<213> ORGANISM: Rattus norvegicus

<400> SEQUENCE: 19
tttttttttt ttttttggc agaattctga tgtttactgg gacccatagt agtcaaggtg       60
acagcaaggg taggggagga aactcagcag aggcggatcc caggtctgga gggaagctga     120
cagcagccca gtaagctgtg ccagaaggct gtaacagtag cggagccagt gacagcgcca     180
ggctgggctg ggttctctct gtgggtgtgc acggcaaagc tgcggcctgt gggccctggg     240
gggcctgtca gctccacatc caccacatgc atgtcggtga ggctaaggtc agccacaagc     300
accccaatga cacgatcaaa gcctagactg ggagcggcca gggcagcggc tgccatggtg     360
ttggagtttc gggggggccaa ggggcagagc ccacgcacag ggccctcata gagcactgtg     420
cggggcccac tactatgtgc ggcagccagg ggtccctcca gccggaagcc atcaggatgt     480
gtgg                                                                  484

<210> SEQ ID NO 20
<211> LENGTH: 161
<212> TYPE: PRT
<213> ORGANISM: Rattus norvegicus

<400> SEQUENCE: 20

Gly Ser Pro Ser Ala Leu Ala Asp Gln Thr Thr Glu Arg Gln Leu Leu
  1               5                  10                  15

Glu Ala Ser Asn His Trp Gly His Thr Val Phe Val Ala Arg Gly Ala
             20                  25                  30

Leu Trp Gly Cys Glu Asp Ile Ser Arg Leu Asp Ala Ala Gly Gly Leu
```

```
                     35                  40                  45
Gln Ser Leu Arg Val Thr Met Ala Thr His Pro Asp Gly Phe Arg Leu
         50                  55                  60

Glu Gly Pro Leu Ala Ala Ala His Ser Ser Gly Pro Arg Thr Val Leu
 65                  70                  75                  80

Tyr Glu Gly Pro Val Arg Gly Leu Cys Pro Leu Ala Pro Arg Asn Ser
                 85                  90                  95

Asn Thr Met Ala Ala Ala Ala Leu Ala Ala Pro Ser Leu Gly Phe Asp
            100                 105                 110

Arg Val Ile Gly Val Leu Val Ala Asp Leu Ser Leu Thr Asp Met His
        115                 120                 125

Val Val Asp Val Glu Leu Thr Gly Pro Pro Gly Pro Thr Gly Arg Ser
130                 135                 140

Phe Ala Val His Thr His Arg Glu Asn Pro Ala Gln Pro Gly Ala Val
145                 150                 155                 160

Thr

<210> SEQ ID NO 21
<211> LENGTH: 161
<212> TYPE: PRT
<213> ORGANISM: Caenorhabditis elegans

<400> SEQUENCE: 21

Gly Ser Pro Thr Cys Phe Ala Asn Gln Glu Leu Leu Glu Lys Leu Thr
  1               5                  10                  15

Lys Leu Ser Leu Ser His Gly Lys Lys Leu Leu Ile Pro Ala Gly Ala
             20                  25                  30

Leu Trp Gly Ala Asn Asp Ile Gln Lys Met Ala Asp Val Gly Ser Leu
         35                  40                  45

Lys Gly Leu Thr Val Thr Met Ile Lys His Pro Thr Ser Phe Lys Leu
     50                  55                  60

Gly Ser Pro Leu Phe Glu Ile Asn Glu Lys Ala Lys Leu Glu Glu Thr
 65                  70                  75                  80

Asn Glu Thr Val Leu Tyr Glu Gly Ser Val Arg Gly Leu Cys Pro Leu
                 85                  90                  95

Ala Pro Asn Asn Val Asn Thr Met Ala Gly Gly Ala Leu Ala Ala Ser
            100                 105                 110

Asn Leu Gly Phe Asp Glu Val Lys Ala Lys Leu Ile Ser Asp Pro Lys
        115                 120                 125

Met Thr Asp Trp His Val Val Glu Val Arg Val Glu Gly Asp Asp Gly
130                 135                 140

Phe Glu Val Ile Thr Arg Arg Asn Asn Pro Ala Lys Pro Gly Ala Val
145                 150                 155                 160

Thr

<210> SEQ ID NO 22
<211> LENGTH: 1019
<212> TYPE: DNA
<213> ORGANISM: Rattus norvegicus

<400> SEQUENCE: 22
ggtctctgga ccctaccggt tgtgtggccc aagcgggtga ctgcagccag gatggcttcg      60
aagtcggggg acggtggaac tatgtgtgcg ttggagttta cagtacagat gagttgtcag     120
agctgcgtgg acgctgtgca caagaccctg aaaggggcgg cgggtgtcca gaatgtggaa     180
```

```
gttcagttgg agaaccagat ggtgttggtg cagaccactt tgcccagcca ggaggtgcaa      240
gcgctcctgg aaagcacagg gaggcaggct gtactcaagg gcatgggcag cagccaacta      300
aagaatctgg gagcagcagt ggccattatg gagggcagtg gcaccgtaca gggggtggtc      360
cgcttcctac agctgtcctc tgagctctgc ctgattgagg aaccatcga cggcctggag      420 cctgggctgc atgggcttca tgtccatcag tatggggacc ttaccaagga ctgcagcagc      480 tgtgggacc attttaaccc tgatggagca tctcatgggg gtcctcagga cactgatcgg       540
caccggggag atctgggcaa tgttcacgct gaagctagtg gccgagctac cttccggata      600
gaggataaac agctgaaggt gtgggatgtg attggccgca gtctggttgt tgatgaggga      660
gaagatgacc tgggccgggg aggccatccc ttatccaagg tcacagggaa ttctgggaag      720
aggttggcct gtggcatcat tgcacgctct gctggccttt tccagaatcc caagcagatc      780
tgctcctgtg atgggctcac tatctgggag gagcgaggcc ggcccattgc tggccaaggc      840
cgaaaggact cagcccaacc ccctgctcac ctctgaacag agcctcctgt caggttattc      900
agtcctccta gctgaacatc ttcctgcaga gggagcctca agcccttgct tgtataggcc      960
taaagggcag ataggcattg ttgtatcctg agcaaattaa attgttactc tcatatggc     1019

<210> SEQ ID NO 23
<211> LENGTH: 878
<212> TYPE: DNA
<213> ORGANISM: Rattus norvegicus

<400> SEQUENCE: 23
ggcacgagca gagagattgt cccaacagag aggcaattct attccctacc aacatgaagc       60
tgttgctgct gctgctgtgt ctgggcctga cactggtctg tggccatgca gaagaagcta      120
gttccacaag agggaacctc gatgtggcta agctcaatgg ggattggttt tctattgtcg      180
tggcctctaa caaagagaa aagatagaag agaatggcag catgagagtt tttatgcagc       240
acatcgatgt cttggagaat tccttaggct tcaagttccg tattaaggaa atggagagt       300 gcagggaact atatttggtt gcctacaaaa cgccagagga tggcgaatat tttgttgagt      360
atgacggagg gaatacattt actatactta agacagacta tgacagatat gtcatgtttc      420
atctcattaa tttcaagaac gggggaaacct tccagctgat ggtgctctac ggcagaacaa      480
aggatctgag ttcagacatc aaggaaaagt ttgcaaaact atgtgaggcg catggaatca      540
ctagggacaa tatcattgat ctaaccaaga ctgatcgctg tctccaggcc cgaggatgaa      600
gaaaggcctg agcctccagt gctgagtgga gacttctcac caggactcta gcatcaccat      660
ttcctgtcca tggagcatcc tgagacaaat tctgcgatct gatttccatc ctctgtcaca      720
gaaaagtgca atcctggtct ctccagcatc ttccctaggt tacccaggac aacacatcga      780
gaattaaaag ctttcttaaa tttctcttgg ccccacccat gatcattccg cacaaatatc      840
ttgctcttgc agttcaataa atgattaccc ttgcactt                             878

<210> SEQ ID NO 24
<211> LENGTH: 256
<212> TYPE: DNA
<213> ORGANISM: Rattus norvegicus

<400> SEQUENCE: 24
ccatggatga atcttccag catctgaatg cctaccgcca ggaggctcac aactgcatct        60
ccagccacat tccattgatc atccagtatt tcatcttgaa gatgtttgct gagaagctgc      120
agaagggcat gctccagctc ctgcaggaca aggattcctg cagctggctc ctgaaggaaa      180
```

```
agagtgacac cagtgagaag aggagattcc tgaaggagcg gttggcaagg ctggcccaag      240
ctcagcgcag gctagc                                                      256

<210> SEQ ID NO 25
<211> LENGTH: 84
<212> TYPE: PRT
<213> ORGANISM: Rattus norvegicus

<400> SEQUENCE: 25

Met Asp Glu Ile Phe Gln His Leu Asn Ala Tyr Arg Gln Glu Ala His
1               5                   10                  15

Asn Cys Ile Ser Ser His Ile Pro Leu Ile Ile Gln Tyr Phe Ile Leu
            20                  25                  30

Lys Met Phe Ala Glu Lys Leu Gln Lys Gly Met Leu Gln Leu Leu Gln
        35                  40                  45

Asp Lys Asp Ser Cys Ser Trp Leu Leu Lys Glu Lys Ser Asp Thr Ser
    50                  55                  60

Glu Lys Arg Arg Phe Leu Lys Glu Arg Leu Ala Arg Leu Ala Gln Ala
65                  70                  75                  80

Gln Arg Arg Leu

<210> SEQ ID NO 26
<211> LENGTH: 84
<212> TYPE: PRT
<213> ORGANISM: Rattus norvegicus

<400> SEQUENCE: 26

Met Asp Glu Ile Phe Gln His Leu Asn Ala Tyr Arg Gln Glu Ala His
1               5                   10                  15

Asn Cys Ile Ser Ser His Ile Pro Leu Ile Ile Gln Tyr Phe Ile Leu
            20                  25                  30

Lys Met Phe Ala Glu Lys Leu Gln Lys Gly Met Leu Gln Leu Leu Gln
        35                  40                  45

Asp Lys Asp Ser Cys Ser Trp Leu Leu Lys Glu Lys Ser Asp Thr Ser
    50                  55                  60

Glu Lys Arg Arg Phe Leu Lys Glu Arg Leu Ala Arg Leu Ala Gln Ala
65                  70                  75                  80

Gln Arg Arg Leu

<210> SEQ ID NO 27
<211> LENGTH: 368
<212> TYPE: DNA
<213> ORGANISM: Homo sapiens

<400> SEQUENCE: 27
tctagaagtc actttggaag aagtatatgc aggaaatttt gtggaagtag ttagaaacaa      60
acctgtggca aggcaggctc ctggcaaacg gaagtgcaat tgtcggcaag agatgcggac     120
cacccagctg ggccctgggc gcttccaaat gacccaggag gtggtctgcg acgaatgccc     180
taatgtcaaa ctagtgaatg aagaacgaac gctggaagta gaaatagagc tgggggtgag     240
agacggcatg gagtacccct ttattggaga aggtgagcct cacgtggatg ggagcctgg      300 agatttacgg ttccgaatca agttgtcaa gcacccaata tttgaaagga gaggagatga      360
tttgtaca                                                              368

<210> SEQ ID NO 28
```

```
<211> LENGTH: 121
<212> TYPE: PRT
<213> ORGANISM: Rattus norvegicus

<400> SEQUENCE: 28

Lys Val Thr Leu Glu Glu Val Tyr Ala Gly Asn Phe Val Glu Val Val
 1               5                  10                  15

Arg Asn Lys Pro Val Ala Arg Gln Ala Pro Gly Lys Arg Lys Cys Asn
             20                  25                  30

Cys Arg Gln Glu Met Arg Thr Thr Gln Leu Gly Pro Gly Arg Phe Gln
         35                  40                  45

Met Thr Gln Glu Val Val Cys Asp Glu Cys Pro Asn Val Lys Leu Val
     50                  55                  60

Asn Glu Glu Arg Thr Leu Glu Val Glu Ile Glu Pro Gly Val Arg Asp
 65                  70                  75                  80

Gly Met Glu Tyr Pro Phe Ile Gly Glu Gly Glu Pro His Val Asp Gly
             85                  90                  95

Glu Pro Gly Asp Leu Arg Phe Arg Ile Lys Val Val Lys His Arg Ile
            100                 105                 110

Phe Glu Arg Arg Gly Asp Asp Leu Tyr
            115                 120

<210> SEQ ID NO 29
<211> LENGTH: 121
<212> TYPE: PRT
<213> ORGANISM: Homo sapiens

<400> SEQUENCE: 29

Glu Val Thr Leu Glu Glu Val Tyr Ala Gly Asn Phe Val Glu Val Val
 1               5                  10                  15

Arg Asn Lys Pro Val Ala Arg Gln Ala Pro Gly Lys Arg Lys Cys Asn
             20                  25                  30

Cys Arg Gln Glu Met Arg Thr Thr Gln Leu Gly Pro Gly Arg Phe Gln
         35                  40                  45

Met Thr Gln Glu Val Val Cys Asp Glu Cys Pro Asn Val Lys Leu Val
     50                  55                  60

Asn Glu Glu Arg Thr Leu Glu Val Glu Ile Glu Pro Gly Val Arg Asp
 65                  70                  75                  80

Gly Met Glu Tyr Pro Phe Ile Gly Glu Gly Glu Pro His Val Asp Gly
             85                  90                  95

Glu Pro Gly Asp Leu Arg Phe Arg Ile Lys Val Val Lys His Pro Ile
            100                 105                 110

Phe Glu Arg Arg Gly Asp Asp Leu Tyr
            115                 120

<210> SEQ ID NO 30
<211> LENGTH: 184
<212> TYPE: DNA
<213> ORGANISM: Rattus norvegicus

<400> SEQUENCE: 30
gttcgcttgg attttctgtt tctgtgctat tctctgaaga ttgatttcct ttgcagatgc      60
tcttgggagt gtggatgatg ctcacttctg tcataatggc attcagtact aatttttataa   120 gtgcatcttg tgtgaaactc aataaattca attttataat cttttttaaa aaaaaaaaa     180 aaaa                                                                  184
```

<210> SEQ ID NO 31
<211> LENGTH: 183
<212> TYPE: DNA
<213> ORGANISM: Mus musculus

<400> SEQUENCE: 31
gctctctctg ctaatgctgc tttgtgtgat cttcagtgaa cctttgactc atctcatatc     60
cctgggcact cggtctagtg agcgttttgt catcatgtac agtagagaac tagttgaatt    120
aaccatgtga tgttaactat tattaataaa ttttaacttt ttttttcaaa aaaaaaaaa     180 aaa                                                                  183

<210> SEQ ID NO 32
<211> LENGTH: 184
<212> TYPE: DNA
<213> ORGANISM: Mus musculus

<400> SEQUENCE: 32
gctctctctg ctaatgctgc tttgtgtgat cttcagtgaa cctttgactc atctcatatc     60
cctgggcact cggtctagtg agcgttttgt catcatgtac agtagagaac tagttgaatt    120
aaccatgtga tgttaactat tattaataaa ttttaacttt ttttttcaaa aaaaaaaaa     180 aaaa                                                                 184

<210> SEQ ID NO 33
<211> LENGTH: 42
<212> TYPE: PRT
<213> ORGANISM: Rattus norvegicus
<220> FEATURE:
<221> NAME/KEY: VARIANT
<222> LOCATION: (31)
<223> OTHER INFORMATION: Wherein Xaa is any amino acid as described in
      the specification

<400> SEQUENCE: 33

Tyr Lys Ile Ser Thr Glu Cys His Tyr Asp Arg Ser Glu His His Pro
 1               5                  10                  15

His Ser Gln Glu His Leu Gln Arg Lys Ser Ile Phe Arg Glu Xaa His
            20                  25                  30

Arg Asn Arg Lys Ser Lys Arg Thr Lys Arg
        35                  40

<210> SEQ ID NO 34
<211> LENGTH: 48
<212> TYPE: PRT
<213> ORGANISM: Drosophila melanogaster

<400> SEQUENCE: 34

Tyr Lys Val His Ser Lys Val His Lys Ala Arg Met Asp His Ser Pro
 1               5                  10                  15

Arg Ser Lys Asp Arg Lys Asp Arg Lys Gly Arg Lys Ala His Ser Lys
            20                  25                  30

Ile His Lys Asp Tyr Ser Arg Asn Arg Lys Asp His Arg Val Arg Lys
        35                  40                  45

<210> SEQ ID NO 35
<211> LENGTH: 382
<212> TYPE: DNA
<213> ORGANISM: Rattus norvegicus

<400> SEQUENCE: 35
gaattccacg gagccaagaa gcccattggc ctatgctgca tcgctcctgt cctcgcagcc     60

```
aaagtgatca aaggtgtgga ggtcaccgtg ggccatgagc aagaggaggg gggcaagtgg    120
ccatatgctg gaaccgcgga agccgtcaaa gccctgggtg ccaagcactg tgtgaagggt    180
gtgaccgaag ctcacgtcga ccagaaaaac aaggtggtca ccaccccggc cttcatgtgt    240
gagaccgaac tccaccacat ccacgacggg attggggcca tggtgaagaa ggtgctggaa    300
ctcacgggaa agtaacacca ccagcaccac gcttggcctc cgtcgtcgct gtggcacgct    360
cagcctgtgt gctccggtca gc                                            382

<210> SEQ ID NO 36
<211> LENGTH: 385
<212> TYPE: DNA
<213> ORGANISM: Homo sapiens

<400> SEQUENCE: 36
gagttccacc aggccgggaa gcccatcggc ttgtgctgca ttgcacctgt cctcgcggcc     60
aaggtgctca gaggcgtcga ggtgactgtg ggccacgagc aggaggaagg tggcaagtgg    120
ccttatgccg ggaccgcaga ggccatcaag gccctgggtg ccaagcactg cgtgaaggaa    180
gtggtcgaag ctcacgtgga ccagaaaaac aaggtggtca cgaccccagc cttcatgtgc    240
gagacggcac tccactacat ccatgatggg atcggagcca tggtgaggaa ggtgctggaa    300
ctcactggaa agtgacgcgc atggacgggg cccagctagg cgccaggact tggcctcacc    360
ctctggctga ggagctgtcg gctgc                                          385

<210> SEQ ID NO 37
<211> LENGTH: 104
<212> TYPE: PRT
<213> ORGANISM: Rattus norvegicus

<400> SEQUENCE: 37

Glu Phe His Gly Ala Lys Lys Pro Ile Gly Leu Cys Cys Ile Ala Pro
  1               5                  10                  15

Val Leu Ala Ala Lys Val Ile Lys Gly Val Glu Val Thr Val Gly His
             20                  25                  30

Glu Gln Glu Glu Gly Gly Lys Trp Pro Tyr Ala Gly Thr Ala Glu Ala
         35                  40                  45

Val Lys Ala Leu Gly Ala Lys His Cys Val Lys Gly Val Thr Glu Ala
     50                  55                  60

His Val Asp Gln Lys Asn Lys Val Val Thr Thr Pro Ala Phe Met Cys
 65                  70                  75                  80

Glu Thr Glu Leu His His Ile His Asp Gly Ile Gly Ala Met Val Lys
                 85                  90                  95

Lys Val Leu Glu Leu Thr Gly Lys
            100

<210> SEQ ID NO 38
<211> LENGTH: 104
<212> TYPE: PRT
<213> ORGANISM: Rattus norvegicus

<400> SEQUENCE: 38

Glu Phe His Gln Ala Gly Lys Pro Ile Gly Leu Cys Cys Ile Ala Pro
  1               5                  10                  15

Val Leu Ala Ala Lys Val Leu Arg Gly Val Glu Val Thr Val Gly His
             20                  25                  30

Glu Gln Glu Glu Gly Gly Lys Trp Pro Tyr Ala Gly Thr Ala Glu Ala
```

```
                35                  40                  45
Ile Lys Ala Leu Gly Ala Lys His Cys Val Lys Glu Val Val Glu Ala
         50                  55                  60

His Val Asp Gln Lys Asn Lys Val Val Thr Thr Pro Ala Phe Met Cys
 65                  70                  75                  80

Glu Thr Ala Leu His Tyr Ile His Asp Gly Ile Gly Ala Met Val Arg
                 85                  90                  95

Lys Val Leu Glu Leu Thr Gly Lys
            100

<210> SEQ ID NO 39
<211> LENGTH: 661
<212> TYPE: DNA
<213> ORGANISM: Rattus norvegicus

<400> SEQUENCE: 39
atttcaaatt tttattatag aacactttct gatttcaaat ttttattaca gaacaaacat      60
tttctgattt caaatttcta ttataattct ccagtaatca aagcagtggc gttggcatga     120
aggcagacag aggtcatgga agagaccagg ctcagaaaca gccccaccat gcacagcggg     180
atgttttccc accaagggca acatgcaaag ccaggtatcc acatgggtag agtagaaagt     240
cagaccttac atctcacaca caaatgaact caaaatatac cagagagcaa agctaagagc     300
taaaatcaag tttcctaggg caagctgtag taggctccct tgggtgggtt aatgcttttg     360
tggatgtgac taccaaaaat tcaaccagag ccaacgaccc aactattaat gggcagtgga     420
cctaaagaga tttcttcaaa cgatatataa agaaggccac caagcatata aaacatgtga     480
catcagtagt cagagagatg ggaagcagaa gcactagcag atcttaacac ctactagaac     540
agccactaaa aaagagtaag actcacaagg acatgggcac ttctaatctc tgtgcactgc     600
tgccaggaca tacaatagtg tggtcactat ggagactacg gcagtgccta ctaataacag     660
c                                                                    661

<210> SEQ ID NO 40
<211> LENGTH: 661
<212> TYPE: DNA
<213> ORGANISM: Rattus norvegicus

<400> SEQUENCE: 40
atttcaaatt tttattatag aacactttct gatttcaaat ttttattaca gaacaaacat      60
tttctgattt caaatttcta ttataattct ccagtaatca aagcagtggc gttggcatga     120
aggcagacag aggtcatgga agagaccagg ctcagaaaca gccccaccat gcacagcggg     180
atgttttccc accaagggca acatgcaaag ccaggtatcc acatgggtag agtagaaagt     240
cagaccttac atctcacaca caaatgaact caaaatatac cagagagcaa agctaagagc     300
taaaatcaag tttcctaggg caagctgtag taggctccct tgggtgggtt aatgcttttg     360
tggatgtgac taccaaaaat tcaaccagag ccaacgaccc aactattaat gggcagtgga     420
cctaaagaga tttcttcaaa cgatatataa agaaggccac caagcatata aaacatgtga     480
catcagtagt cagagagatg ggaagcagaa gcactagcag atcttaacac ctactagaac     540
agccactaaa aaagagtaag actcacaagg acatgggcac ttctaatctc tgtgcactgc     600
tgccaggaca tacaatagtg tggtcactat ggagactacg gcagtgccta ctaataacag     660
c                                                                    661
```

<210> SEQ ID NO 41
<211> LENGTH: 893
<212> TYPE: DNA
<213> ORGANISM: Rattus norvegicus

<400> SEQUENCE: 41

| | | | | | |
|---|---|---|---|---|---|
| tccccgctga | gttcatcacc | agggacaggt | gacctgagct | gcccctggag | cccagctccc | 60 |
| atttccttct | ggttctggcc | gatctcttcg | ttatgagctg | gctgctgggt | tacgtggacc | 120 |
| ccacagagcc | cagctttgtg | gcggctgtgc | tcaccattgt | gttcaatcca | ctcttctgga | 180 |
| atgtggtagc | aaggtgggag | cagagaactc | gcaagctgag | cagagccttc | gggtcccctt | 240 |
| acctagcctg | ctattccctg | gcagcatca | tcctgcttct | gaacatcctc | cgctcccact | 300 |
| gcttcacaca | ggccatgatg | agccagccca | agatggaggg | cctggatagc | cacaccatct | 360 |
| acttcctggg | ccttgcactc | ctgggctggg | gactcgtgtt | tgtgctctcc | agcttctatg | 420 |
| cactgggggtt | cactgggacc | tttctaggtg | actactttgg | gatcctcaag | gagtccagag | 480 |
| tgaccacatt | tcccttcagc | gtgctggaca | accccatgta | ctggggaagt | acagccaact | 540 |
| acctaggctg | ggcacttatg | cacgccagcc | ctacaggcct | gctgttgacg | gtgctggtgg | 600 |
| cactcgtcta | cgtggttgct | ctcctgtttg | aagagccctt | cactgcggag | atctaccggc | 660 |
| ggaaagccac | caggttgcac | aaaaggagct | gacaggggcca | tgaggggacct | ttggaaagcc | 720 |
| ggattgcctc | ccggctgacc | caagcaacaa | cccttctcgg | ggagagcagc | gctggccatt | 780 |
| gtacctgtgc | cttggaaacc | agtcatgggg | gtgctcaggc | attatgtcat | gtgactgctg | 840 |
| agaccccat | ccccaccaat | ccctgacaca | ctaataaagg | ctttgtgacc | tcc | 893 |

<210> SEQ ID NO 42
<211> LENGTH: 1131
<212> TYPE: DNA
<213> ORGANISM: Rattus norvegicus

<400> SEQUENCE: 42

| | | | | | |
|---|---|---|---|---|---|
| agcaggaatc | ccctccgctt | gcgggtagga | agcttgggga | gcagcctcat | ggaagagaag | 60 |
| cagatcctgt | gcgtggggct | ggtggtgctg | gacatcatca | atgtggtgga | caaatacccca | 120 |
| gaggaagaca | cggatcgcag | gtgcctatcc | cagagatggc | agcgtggagg | caacgcgtcc | 180 |
| aactcctgca | ctgtgctttc | cttgctcgga | gcccgctgtg | ccttcatggg | ctcgctggcc | 240 |
| catggccatg | ttgccgactt | cctggtggcc | gacttcaggc | ggagggggtgt | ggatgtgtct | 300 |
| caagtggcct | ggcagagcca | gggagatacc | ccttgctcct | gctgcatcgt | caacaactcc | 360 |
| aatggctccc | gtaccattat | tctctacgac | acgaacctgc | cagatgtgtc | tgctaaggac | 420 |
| tttgagaagg | tcgatctgac | ccggttcaag | tggatccaca | ttgagggccg | gaatgcatcg | 480 |
| gaacaggtaa | agatgctaca | gcggatagaa | cagtacaatg | ccacgcagcc | tctgcagcag | 540 |
| aaggtccggg | tgtccgtgga | gatagagaag | ccccgagagg | aactcttcca | gctgttcggc | 600 |
| tatgagagg | tggtgtttgt | cagcaaagat | gtggccaagc | acctggggtt | ccggtcagca | 660 |
| ggggaggccc | tgaagggctt | gtacagtcgt | gtgaagaaag | gggctacgct | catctgtgcc | 720 |
| tgggctgagg | agggagccga | tgccctgggc | cccgacggcc | agctgctcca | ctcagatgcc | 780 |
| ttccccaccac | cccgagtagt | agacactctc | ggggctggag | acaccttcaa | tgcctctgtc | 840 |
| atcttcagcc | tctccaaggg | aaacagcatg | caggaggccc | tgagattcgg | gtgccaggtg | 900 |
| gctggcaaga | agtgtggctt | gcaggggttt | gatggcattg | tgtgagagat | gagcggtggg | 960 |
| aggtagcagc | tcgacacctc | agaggctggc | accactgcct | gccattgcct | tcttcatttc | 1020 |

-continued

| | |
|---|---|
| atccagcctg gcgtctggct gcccagttcc ctgggccagt gtaggctgtg gaacgggtct | 1080 |
| ttctgtctct tctctgcaga cacctggagc aaataaatct tcccctgagc c | 1131 |

<210> SEQ ID NO 43
<211> LENGTH: 1994
<212> TYPE: DNA
<213> ORGANISM: Rattus norvegicus

<400> SEQUENCE: 43

| | |
|---|---|
| atctctccca ggggctgtgg actgctggct ttctgttgat accttagaga tgcagcggct | 60 |
| tttggctcca gcaaggcggg tcctgcaagt gaagagagtc atgcaggaat cttcgctctc | 120 |
| acccgctcac ctgctccccg cagcccagca gaggttttct acaatccctc ctgctcccct | 180 |
| ggccaaaact gatacatggc caaagatgt gggcatcctt gccctggagg tctactttcc | 240 |
| agcccaatat gtggaccaaa ctgacctgga gaagttcaac aatgtggaag cagggaagta | 300 |
| cacagtgggc ttgggccaga cccgtatggg cttctgttcg gtccaggagg acatcaactc | 360 |
| cttgtgcctc acagtggtgc agaggctgat ggaacgcaca aagctgccat gggatgccgt | 420 |
| aggccgcctg gaagtgggca cggaaaccat cattgacaag tccaaggctg tcaagacagt | 480 |
| gctcatggag ctcttccagg attcaggcaa cactgacatc gagggcatag ataccaccaa | 540 |
| cgcctgctat ggtggcactg cctccctctt caacgctgcc aactgatgg agtccagcta | 600 |
| ctgggatggt cgctatgccc tggtggtctg tggtgatatc gcagtctacc caagtggtaa | 660 |
| cccccgcccc acaggtggtg ccgggggctgt ggcaatgctg attgggccca aggcccgct | 720 |
| agtcctggaa caagggctga ggggaaccca catggagaac gcctatgact tctacaaacc | 780 |
| aaacttggcc tcagagtatc cactggtgga tgggaagctg tctatccagt gctacctgcg | 840 |
| ggccttggac cgatgctatg cagcttaccg caggaaaatc cagaatcagt ggaagcaagc | 900 |
| tggaaacaac cagcctttca ccctcgatga cgtgcaatat atgatcttcc acacacctt | 960 |
| ttgcaagatg gtccagaaat ccctagctcg gctgatgttc aatgacttcc tgtcatctag | 1020 |
| cagtgacaag cagaacaact tatacaaggg tctagaggcc ttcaagggtc taaagctgga | 1080 |
| agaaacctac accaacaagg atgttgacaa ggctctgctg aaggcctccc tggacatgtt | 1140 |
| caacaagaaa accaaggcct ccctttacct ctccacaaac aatgggaaca tgtacacctc | 1200 |
| gtccctctac gggtgcctgg cctcacttct ctcccaccac tctgcccaag aattggccgg | 1260 |
| ctccaggatt ggagccttct cctacggctc aggcttagca gcaagtttct tctcatttcg | 1320 |
| agtgtccaag gacgcttccc caggttcccc tctggagaag ctggtgtcta gtgtgtcaga | 1380 |
| tctgcccaaa cgtctagact cccggagacg catgtcccct gaggaattca cagaaataat | 1440 |
| gaatcagaga gagcaattt accacaaggt gaacttctct cccctggtg acacaagcaa | 1500 |
| cctcttccca ggcacttggt accttgaacg agtggatgag atgcaccgca gaaaatatgc | 1560 |
| ccggcgtccc gtctaaggag accaatccat acaaccattc cccgggggaa gaatgtgagc | 1620 |
| agagccgtta cccaaacggc ttccacttaa aattccaccc acagcagtga acggtgaata | 1680 |
| gacacagcga cccatagga tctgctccgc ggtgaagggc ctccctctgt ggatcctggg | 1740 |
| tgaccctccc tgaagcagtg agcaccacag gttctgctgt ggaccagagc cccctgtgg | 1800 |
| agagggagaa agaaggga gccgctgacc tgcagggata cagaccttcc ccacagcctg | 1860 |
| gcagccgccc gtttgttgca gcttattatc agactgtggg ctatcatagt tcatgctcgt | 1920 |
| ttcttaaagt ttcccgagaa tttctaaaat tttgtatcta aacttttaat atggcgatta | 1980 |
| aaaggagaga agga | 1994 |

<210> SEQ ID NO 44
<211> LENGTH: 1850
<212> TYPE: DNA
<213> ORGANISM: Rattus norvegicus

<400> SEQUENCE: 44

```
gaattccggt tctagttgtt gttttctctg ccatctgctc tccgggcgcc gtcaaccatg        60
ggtccgtgga cccactcctt gcgcgccgcc ctgctgctgg tgcttttggg agtctgcacc       120
gtgagctccg acactcctgc caactgcact taccctgacc tgctgggtac ctgggttttc       180
caggtgggcc ctagacatcc ccgaagtcac attaactgct cggtaatgga accaacagaa       240
gaaaaggtag tgatacacct gaagaagttg gatactgcct atgatgaagt gggcaattct       300
gggtatttca ccctcattta caaccaaggc tttgagattg tgttgaatga ctacaagtgg       360
tttgcgtttt tcaagtatga agtcaaaggc agcagagcca tcagttactg ccatgagacc       420
atgacagggt gggtccatga tgtcctgggc cggaactggg cttgctttgt tggcaagaag       480
atggcaaatc actctgagaa ggtttatgtg aatgtggcac accttggagg tctccaggaa       540
aaatattctg aaaggctcta cagtcacaac cacaactttg tgaaggccat caattctgtt       600
cagaagtctt ggactgcaac cacctatgaa gaatatgaga actgagcat acgagatttg       660
ataaggagaa gtggccacag cggaaggatc ctaaggccca acctgcccc gataactgat       720
gaaatacagc aacaaatttt aagtttgcca gaatctgggg actggagaaa cgtccgtggc       780
atcaatttg ttagccctgt tcgaaaccaa gaatcttgtg gaagctgcta ctcatttgcc       840
tctctgggta tgctagaagc aagaattcgt atattaacca acaattctca gaccccaatc       900
ctgagtcctc aggaggttgt atcttgtagc ccgtatgccc aaggttgtga tggtggattc       960
ccataccca ttgcaggaaa gtatgcccaa gattttgggg tggtggaaga aaactgcttt      1020
ccctacacag ccacagatgc tccatgcaaa ccaaaggaaa actgcctccg ttactattct      1080
tctgagtact actatgtggg tggttttctat ggtggctgca atgaagccct gatgaagctt      1140
gagctggtca aacacggacc catggcagtt gcctttgaag tccacgatga cttcctgcac      1200
taccacagtg ggatctacca ccacactgga ctgagcgacc ctttcaaccc ctttgagctg      1260
accaatcatg ctgttctgct tgtgggctat ggaaaagatc cagtcactgg gttagactac      1320
tggattgtca gaacagctg ggctctcaa tggggtgaga gtggctactt ccggatccgc      1380
agaggaactg atgaatgtgc aattgagagt atagccatgg cagccatacc gattcctaaa      1440
ttgtaggacc tagctcccag tgtcccatac agcttttat tattcacagg gtgatttagt      1500
cacaggctgg agacttttac aaagcaatat cagaagctta ccactaggta cccttaaaga      1560
atttgccct taagtttaaa acaatccttg attttttct tttaatatcc tccctatcaa      1620
tcaccgaact acttttcttt ttaaagtact tggttaagta atactttct gaggattggt      1680
tagatattgt caaatatttt tgctggtcac ctaaaatgca gccagatgtt tcattgttaa      1740
aaatctatat aaaagtgcaa gctgcctttt ttaaattaca taaatcccat gaatacatgg      1800
ccaaaatagt tattttttaa agactttaaa ataaatgatt aatcgatgct                1850
```

<210> SEQ ID NO 45
<211> LENGTH: 993
<212> TYPE: DNA
<213> ORGANISM: Rattus norvegicus

<400> SEQUENCE: 45

```
ggcaagggct ggaatactaa aagttattca tgatgtcaga ctatacttgg tttgaaggaa      60
taccttttcc tgccttttgg ttttccaaag aaattctgga aaatagttgt aagaagtttg     120
tggtaaaaga agacgacttg atcatattga cttaccccaa gtcaggaacg aactggctga     180
tcgagattgt ctgcttgatt cagaccaagg gagatcccaa gtggatccaa tctatgccca     240
tctgggatcg ctcaccctgg atagagactg gttcaggata tgataaatta accaaaatgg     300
aaggaccacg actcatgacc tcccatcttc ccatgcatct tttctccaag tctctcttca     360
gttccaaggc caaggtgata tatctcatca gaaatcccag agatgttctt gtttctgctt     420
attttttctg gagtaagatc gccctggaga agaaaccaga ctcgctggga acttacgttg     480
aatggttcct caaaggaaat gttgcatatg gatcatggtt tgagcacatc cgtggctggc     540
tgtctatgag agaatgggac aacttcttgg tactgtacta tgaagacatg aaaaaggata     600
caatgggatc cataaagaag atatgtgact cctggggaa aaaattagag ccagatgagc      660
tgaatttggt cctcaagtat agttccttcc aagtcgtgaa agaaaacaac atgtccaatt     720
atagcctcat ggagaaggaa ctgattctta ctggttttac tttcatgaga aaaggcacaa     780
ctaatgactg gaagaatcac ttcacagtag cccaagctga agcctttgat aaagtgttcc     840
aggagaaaat ggccggtttc cctccaggga tgttcccatg ggaataaatt ttcaaaagtt     900
ttaaatattt tatgaacact gatgtttatg tttatgttgt tctatgatgt ctgaataact     960
gaatgtgatc attgaataaa tcctgttgtg gat                                  993

<210> SEQ ID NO 46
<211> LENGTH: 5001
<212> TYPE: DNA
<213> ORGANISM: Rattus norvegicus

<400> SEQUENCE: 46
cacaaaccca gcgagcattg aacactgcac acggccatct gcccagagag ctgtgaccac      60
cacttccgct actatctact cagaaagtcg tgactactga gccactgctg cctgcccaga     120
ttctcatcca ccgcctgctg cgtctggttg cgatgccgga gttcctaact gttgtttctt     180
ggccgttcct gatcctcctg tccttccagg ttcgcgtagt cgctggagcc cccagccat      240 ggcactgtgc tccctgcact gctgagaggc tggagtctg tccacccgtg cctgcttcgt      300
gccccgagat ttctcggcct gcgggctgtg gctgctgccc gacatgtgcc ttgccactgg     360
gtgctgcctg tggtgtggcc actgcggcct gcgctcaggg actcagctgc cgtgcgctgc     420 cagggagcc tcgacctctg catgcccta cccgtggcca gggagcctgt gtactagaac      480
ctgccgcacc cgccacgagc agcttgtccg gttctcagca tgaaggtact acagccctct     540
ctgcctcttg atctcttggc taggacacac gtgctttcta ggcacgtcag aggcctatcc     600
ggaacctata gcagatagga caaaggctct ccatgcccac tttgagcttt cagcctcaaa     660
taaggccctc agttaggtcg tggcggcttg ggaaacacca gaggtgtcaa tccagtagca     720
gagtggagaa gttgggaaga atgttccaag ctcccagtgc agagtggaga gttgggaaga     780
atgttcacag actaggtagt actgatcctg cttggtcttt cagtggggag ggagctatgg     840
ggctgccagg tgggtggggt gctggcccaa acacctcttt ctgtgggtcc tgaccttggc     900
agttccaatg ctaaaaggt ccaggaaggt ttaggatggg agccctcctg ctgccccag       960 gaggtttgca atgtcctttg tagcatatat cctgccacac agtatgtgct tcccagatgt    1020
ttacagaaca taatgtgaaa atttaggccc aaaccttcac ttccattcat tgctatagac    1080
aaacagtgtt tgaagtgtat gttgcctgct aggagtctga caatcaggcg cttttcctgaa    1140
```

```
tttaagcact ggtttgtttg taataggaag cttgggaaat gcctcttcct ctgctccagc   1200
ccctatctcc cctgtctggg ctgcatgcac ttcctgtgtg ggtaagggac ctcatggttc   1260
catattctga cgggaagccg gactgcaggc atctgatcct tttgactaaa tggaagaact   1320
atcccaacgg tccttagaaa cgggcttccc caggagcgat gtctgataat gtcctcctct   1380
gtgaggggct gcctaagagg tgtcggtgtt caagaaagca gggctcccag aaaagaagag   1440
gatggtggtg tgaggtgggg aaggctacac tctacacctt gcttctcaac tatcccctta   1500
ctggggtctt acgagattct ttttgtggtg tggagaggag agctgagtgg tcaagtctca   1560
ccactaacgg gttcaagcct tggcctcagt ccttggcttc ttcaggatta catcctagac   1620
ccaactctct ctgccatggg gactcccttg cctaaccccca aaacatacca tttccccaga   1680
aaggaattag tattgctaat tggtgataat tgttcccaaa tagcccactg gtgaaaacaa   1740
agcctgattt cacctgactg ttacagattg tcttaaggc ggtagacgtg agtgacatag    1800
gagtgacacc tcagggctca tcgtctgtgt ctgtggggtt cgttttcaga ggcaaaggct   1860
gctgtggcct ctgaggatga gcttgccgag agcccagaga tgacagagga acagctgctg   1920
gatagcttcc acctcatggc cccatcccgt gaggaccagc ccatcctgtg gaatgccatt   1980
agcacctaca gcagcatgcg ggcccgggag atcactgacc tcaagaaatg gaaggtgaga   2040
ccctgcactc agaccttcag gtttagctat ctacgtgaag aggtttgtct agacgatttc   2100
ttaaagggca ctgagcatgg ggctgagaac ggggatataa ctaccccccat ccctgatgta   2160
tttctgcctc cttaaaaata tggcaagtat ctcagagcat aaggtaggcc atttttcagt   2220
ctaggtttct ctgtcaccga gtacgcacgt tcagtgattg ttagccacca accagctcca   2280
cggttttgcc agcctttagc tatgcacttt agctatgcag taaacttctc tagctttact   2340
ggctgttttt caacttgacc acttgggga gacagagaac caaggtgga gagaaagtac     2400
ggcagaggca ttgaagaagt acacctaagg aaatgaaagg ataaacattg ttaggggcac   2460
tttagaattt catatggaaa ttgtccaaat cagtgccttg ttccgtaatc aatttgacat   2520
acaccaaatg caaggatggc tgtttgaaaa atctaggcat ttatgatgct aaattccaca   2580
cacagagact gagcctgtct ttttttattag agttcaggtg ctcaagttat tcagagatag   2640
ccagggtcag gaagcattta taccattggc caggctctta ccacaatgtc gttaagggg    2700
tctccagaaa atgccactga gggaggatga gagtggtgtc cctgtccttt atctacatag   2760
cccaagccaa agaccaacct gtcctgctca cagatgggga aacatctcag ccgttgtcta   2820
aattgataat ttttgtctct tgtactcatg ctaatataaa attatccttt taggagccct   2880
gccaacggga actctataaa gtgttagaga gattagctgc cgctcaacag aaagcaggag   2940
atgagatcta caaattttat ctgccaaact gcaacaagaa tggatttat cacagcaaac    3000
aggtaggtgg ctttgctcat ccagatcctt gtaaaacttc atgattttt ttttaaagt     3060
caaatgattc acaggcccaa tacacatcat gggtagcttt cttaggtgag atccagccct   3120
gcagtagttg ggagaagcta gtcctgagaa agagatagtg tgatggatga ggaacacttc   3180
agccagaagg gaggactaag cattagtgtg atgagtgagg agcacttcag ttaacaggga   3240
ggactaagca ttagtgtgat gagtgaggac cacttcaagc cagagggagg actaacattg   3300
gcagtatgat gagtgaggag cacttcagcc agtagggagg actaaccatt agtctcatca   3360
ctaggagcac ctcagccaag tagggaggac taaccattag tctcacactc acccaacatc   3420
ttcagtcagg actaagcatt agtgtgatga gtgaggagca cttcagtcag tagggaggac   3480
```

-continued

```
tacattagtg tgatgagtga ggagcacttc agccagtagg gaggactaac cgttcactca       3540
gattagcaga gatggatgtt ccatatactg atgtccaggt ttcagttcct cacaactaga       3600
ggaaagggac acagtcagtg taggagacag atgtctcgcg ttctctcttc ccacaaataa       3660
aaacaaactc tgtagtaaga cacaccaatt gtgctttgcc tagcaataaa tgagattgaa       3720
gaagtccagg cttaatttcg acgcaacttt agaactcagg gaagtgcaag ttctggaatt       3780
tcattgagga aaaacttgag gtctaggtct agccgtgtgg tagagatggt gagacctatc       3840
gttgagctcc tttggcagag ggccatggag caggtaaccg tcaaaacaat ataccactga       3900
gtaaacagat gagattgtta tcaggtgtgc cataaagcca acctctccgt tttgtgatga       3960
caaccagaag ggcattggtc tgccgagcct tagccagcag gtagctgtgc agtgcttggc       4020
ctcactgagg gacaggtggg ccagagctct tacctcctgc tgctcttgac ctcggtcctg       4080
tctttgcagt gcgagacatc tctggatgga gaagctgggc tctgctggtg tgtctaccca       4140
tggagtggga agaagatccc tggatctctg gagaccagag gggaccccaa ctgccaccag       4200
tattttaatg tgcaaaactg aaagttgttt cctccctcct tcttcacaca aaatatttaa       4260
gtatatagtg tatttatact ccggagcaca ccatttttata tatgtgtata tgtatatatc       4320
caggaactag ttttttatact ccacatgctg cttgatgtac aagtgggttt gtatttattc      4380
actctaagtt tatttttttc taccctgtcc ttgtgctgta ttaatttata taactgaagc       4440
ttttctcatc tccatacatg taaatactac catctcagct cttccagagt tctgctttga       4500
aagggcagcg cggtacgtgc ctagaacgag cacaagtcag tctgaggtag gggcctttca      4560
gtgggttcag ggaggaaggt tagccctggc tcggggagac ttcctcatcg aatcccacag       4620
gtctgtgtct gatgcctatt ggctgggaag gttccgatgt tggttgtgta atcaaagcta       4680
aacgtggaaa gctgcgtccc atgcactgtt aaacacacgt ctggaataaa acattctacc       4740
tggaaacact gctgtctctg tggaattcca gctctgtgct cattccctca gtccgttcgg       4800 cttttcccgct cgcctgattc ctgggtctgt gctttgggga tagatgttgc aatacagggt       4860
gcttgtttgt ttacagaaca ccctggacaa acactctgtg actttatggt cccattttca      4920
agcagcatca ggcctctgtc tgggccagac tacagagccc ctcctccttg gtccatctcc       4980
ctttcttccc agggccctca g                                                 5001
```

<210> SEQ ID NO 47
<211> LENGTH: 538
<212> TYPE: DNA
<213> ORGANISM: Rattus norvegicus

<400> SEQUENCE: 47

```
ctccactgca tacatagttg gtgttcaaaa atttccccaa tgtttgttct ggacacaatt        60
gttataagcc aactcggtga attcaagaca ttgttccaca caatgaacaa tcgcacacat       120
gagaactgca cctagaatgt ccatcctaga atctccatcc atccagtcaa agtgctgagc       180
tcactgactg aaggaaacat gacctgtgtt ctagaacgta gctggctatg aagtttactc       240
atgtgtaaat tccttaaaaa gattaaattg tttggcccat ttctatattt cataaaataa       300
ctataattac aaactttcta aaaataattt tacaaccatg taattatgac taaccatatc       360
atctaaaaag taagtgaagt cattgtccta gagattgtct gagattattc tgctgagaag       420
cttacttcaa actcttatca ctacttccta cttccagtgt ccttgaatta agaacagaaa       480
ttgtaactat gctattctac atcagattga cacaacctac ttctaagtac actattgc        538
```

<210> SEQ ID NO 48
<211> LENGTH: 538
<212> TYPE: DNA
<213> ORGANISM: Rattus norvegicus

<400> SEQUENCE: 48

| | | |
|---|---|---|
| ctccactgca tacatagttg gtgttcaaaa atttccccaa tgtttgttct ggacacaatt | 60 |
| gttattagcc aactcggtga attcaagaca ttgttccaca caatgaacaa tcgcacacat | 120 |
| gagaactgca cctagaatgt ccatcctaga atctccatcc atccagtcaa agtgctgagc | 180 |
| tcactgactg aaggaaacat gacctgtgtt ctagaacgta gctggctatg aagtttactc | 240 |
| atgtgtaaat tccttaaaaa gattaaattg tttggcccat ttctatattt cataaaataa | 300 |
| ctataattac aaactttcta aaataatttt tacaaccatg taattatgac taaccatatc | 360 |
| atctaaaaag taagtgaagt cattgtccta gagattgtct gagattattc tgctgagaag | 420 |
| cttacttcaa actcttatca ctacttccta cttccagtgt ccttgaatta agaacagaaa | 480 |
| ttgtaactat gctattctac atcagattga cacaacctac ttctaagtac actattgc | 538 |

<SEQ ID NO 49
<211> LENGTH: 2495
<212> TYPE: DNA
<213> ORGANISM: Rattus norvegicus

<400> SEQUENCE: 49

| | | |
|---|---|---|
| attgcctacc ccgggtggag accgtgctcg tccggccctc ttgcctcacg ttctgcagct | 60 |
| ctgcagctcc gcaatcctac accatggcgg acagccggga cccagccagc gaccagatga | 120 |
| agcagtggaa ggagcagcgg gcccctcaga acccgatgt cctgaccacc ggaggcggga | 180 |
| acccaatagg agataaactt aatatcatga ctgcggggcc ccgagggccc ctcctcgttc | 240 |
| aagatgtggt tttcaccgac gagatggcac actttgacag agagcggatt cctgagagag | 300 |
| tggtacatgc aaagggagca ggtgcttttg gatactttga ggtcacccac gatattacca | 360 |
| gatactccaa ggcaaaggtg tttgagcata ttgggaagag gactcctatt gccgtccgat | 420 |
| tctccacagt cgctggagag tcaggctcag ctgacacagt tcgtgaccct cgtgggtttg | 480 |
| cagtgaaatt ctacactgaa gatggtaact gggacctcgt gggaaacaac acccctattt | 540 |
| tcttcatcag ggatgccatg ttgtttccat cctttatcca tagccagaag agaaacccac | 600 |
| aaactcacct gaaggaccct gacatggtct gggacttctg gagtctttgt ccagagtctc | 660 |
| tccatcaggt tactttcttg ttcagcgacc gagggattcc agatggacat cggcacatga | 720 |
| atggctatgg ctcacacacc ttcaagctgg ttaatgcgaa tggagaggca gtgtactgca | 780 |
| agttccatta caagactgac cagggcatca aaaacttgcc tgttgaagag gcaggaagac | 840 |
| ttgcacagga agacccggat tatggcctcc gagatctttt caatgccatc gccagtggca | 900 |
| attacccatc ctggacttttt tacatccagg tcatgactttt caaggaggca gaaaccttcc | 960 |
| catttaatcc atttgacctg accaaggttt ggcctcacaa ggactaccct cttataccag | 1020 |
| ttggcaaact ggtcttaaac agaaatcctg ctaattattt tgctgaagtt gaacagatgg | 1080 |
| cttttgaccc aagcaacatg ccccctggca ttgagcccag cccggacaag atgctccagg | 1140 |
| ccgccttttt tgcttaccca gacactcacc gccaccgcct gggaccaaac tatctgcaga | 1200 |
| tacctgtgaa ctgtccctac cgtgctcgcg tggccaacta ccagcgcgat ggccccatgt | 1260 |
| gcatgcatga caaccagggt ggtgctccca actactaccc caacagcttc agcgcaccag | 1320 |
| agcagcaggg ctcggccctg gagcaccata gccagtgctc tgcagatgtg aagcgcttca | 1380 |

-continued

| | | |
|---|---|---|
| acagtgctaa tgaagacaac gtcactcagg tgcggacatt ctatacgaag gtgttgaatg | 1440 |
| aggaggagag gaaacgcctg tgtgagaaca ttgccaacca cctgaaagat gctcagcttt | 1500 |
| tcattcagag gaaagcggtc aagaatttca ctgacgtcca ccctgactac ggggcccgag | 1560 |
| tccaggctct tctggaccag tacaactccc agaagcctaa gaatgcaatt cacacctacg | 1620 |
| tacaggccgg ctctcacata gctgccaagg gaaaagctaa cctgtaaagc acgggtgctc | 1680 |
| agcctcctca gcctgcactg aggagatccc tcatgaagca gggcacaagc ctcaccagta | 1740 |
| atcatcgctg gatggagtct cccctgctga agcgcagact cacgctgacg tctttaaaac | 1800 |
| gataatccaa gcttctagag tgaatgatag ccatgctttt gatgacattt cccgaggggg | 1860 |
| aaattaaaga ttagggctta gcaatcactt aacagaaaca tggatctgct taggacttct | 1920 |
| gtttggatta ttcatttaaa atgattacaa gaaaggtttt ctagccagaa acatgatttg | 1980 |
| attagatatg atatatgata aaatcttggt gatttactta tagtcttatg ttacctcaca | 2040 |
| gcctggtata tatacaacac acacacacac acacacacac acacaccaaa acacacatac | 2100 |
| actatacaca cacacacaca cacacactaa aacacacata cacaacacac acatacacta | 2160 |
| cacacacaga acacacaaca caaacataca catataggca cacacacaca cacacacaca | 2220 |
| cacacacaca cacacacaca cacacatgaa tgaagggatt ataaagatgg cccacccaga | 2280 |
| atttttttt attttctaa ggtccttata agaaaaacca tacttggatc atgtcttcca | 2340 |
| aaaataactt tagcactgtt gaaacttaat gtttattcct gtgtagttga ttggattcct | 2400 |
| tttccccttg aaattatgtt tatgctgata cacagtgatt tcacataggg tgatttgtat | 2460 |
| ttgcttacat ttttacaata aaatgatctt catgg | 2495 |

<210> SEQ ID NO 50
<211> LENGTH: 1884
<212> TYPE: DNA
<213> ORGANISM: Rattus norvegicus

<400> SEQUENCE: 50

| | | |
|---|---|---|
| caagcctttg ctggagaccg ctcctgtcca gtccgcagct ggcttcagcg ccactcagga | 60 |
| caccggaaag atggcaccga ttgccggcaa gaaggccaag agggggaatct tagaacgctt | 120 |
| aaatgctggc gaagtcgtga tcggagatgg gggatttgtc tttgcactgg aaaagagggg | 180 |
| ctacgtaaag gctggaccct ggaccccaga ggctgcggtg gagcaccccg aggcagttcg | 240 |
| gcagcttcat cgggagttcc tcagagctgg atcgaacgtc atgcagacct tcactttcta | 300 |
| tgcaagtgag gacaagctgg aaaaccgagg gaactacgtg gcagagaaga tatctgggca | 360 |
| gaaggtcaat gaagctgctt gtgacattgc acggcaagtt gctgacgaag gggatgcatt | 420 |
| ggttgcagga ggtgtgagtc agacaccttc ctacctcagc tgcaagagtg agacggaagt | 480 |
| taaaaagata tttcaccaac agcttgaggt cttcatgaag aagaatgtgg acttcctcat | 540 |
| tgcagagtat tttgaacatg ttgaagaagc cgtgtgggca gtcgaggcct taaaaacatc | 600 |
| cgggaagcct atagcggcta ccatgtgcat cggacctgaa ggagatctac atggcgtgtc | 660 |
| tcctggagag tgcgcagtgc gttttggtaa agcaggtgcc gccattgtcg gtgtgaactg | 720 |
| ccacttcgac cccagcacca gcttgcagac aataaagctc atgaaggagg gtctggaagc | 780 |
| agctcggctg aaggcttact tgatgagcca cgccctggcc taccacaccc ctgactgtgg | 840 |
| caaacaggga tttattgatc tcccagaatt ccccttggga ttggaaccca gagttgccac | 900 |
| cagatgggat attcaaaaat acgccagaga ggcctacaac ctgggggtca ggtacattgg | 960 |
| cggctgctgc ggatttgagc cctaccacat cagggccatt gcagaggagc tcgccccaga | 1020 |

```
aagggggattt ttaccaccag cttcagaaaa acatggcagc tggggaagtg gtttggacat    1080
gcacaccaaa ccctggatca gggcaagggc caggaaagaa tactggcaga atcttcgaat    1140
agcttcgggc agaccgtaca atccttcgat gtccaagccg gatgcttggg gagtgacgaa    1200
aggggcagca gagctgatgc agcagaagga agccaccact gagcagcagc tgagagcgct    1260
cttcgaaaaa caaaaattca aatccgcaca gtagccacag gccagcggtt cggggcgaat    1320
tcctccaggt ccgggccaca gtgtgcaccc ggaaggagaa ggcatctcta aaccagcgtt    1380
tgtgttgatg ccggcttaca cctgtgattg gtgctagtta gacaaaatgg agtcacagat    1440
agcatttcac agttacaaaa ctacgcttta gaattttacc tagaaggaag aaaggagaag    1500
tccacagtaa atcctgaaca catttcctac gtgcctgtcg cattacaggc gcacaggagt    1560
cactgcagcg aagagaaagt cacccgacgt caatctcatt tcagataggg ggataggaca    1620
ccacctccac gagtgacata gaaccattca gggaccgtat cataagtgac acagcaacca    1680
tctatatcta agatgcttcc caagtggatt ccaagatctt ttgagcagga cccttaggca    1740
gaaacaacac acaccagccc tgtaaaactt aacagataac tgatccattc tgtaattctg    1800
taatctctgt tctgactgct tccattccat ttcattaata aaaacatgcc ggttgaaaac    1860
cttcaaaaaa aaaaaaaaaa aaaa                                          1884
```